(12) United States Patent
Yeoh et al.

(10) Patent No.: US 10,349,818 B2
(45) Date of Patent: *Jul. 16, 2019

(54) ADAPTIVE CONTROL OF A FIBER SCANNER WITH PIEZOELECTRIC SENSING

(71) Applicant: University of Washington through its Center for Commercialization, Seattle, WA (US)

(72) Inventors: Ivan L. Yeoh, Fort Lauderdale, FL (US); Per G. Reinhall, Seattle, WA (US); Eric J. Seibel, Seattle, WA (US); Matthew J. Kundrat, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/835,287

(22) Filed: Dec. 7, 2017

(65) Prior Publication Data
US 2018/0103834 A1 Apr. 19, 2018

Related U.S. Application Data

(63) Continuation of application No. 15/107,894, filed as application No. PCT/US2014/072372 on Dec. 24, 2014, now Pat. No. 9,872,606.
(Continued)

(51) Int. Cl.
*G02B 26/08* (2006.01)
*A61B 1/00* (2006.01)
(Continued)

(52) U.S. Cl.
CPC ...... *A61B 1/00172* (2013.01); *A61B 1/00006* (2013.01); *A61B 1/00165* (2013.01);
(Continued)

(58) Field of Classification Search
CPC .............. A61B 1/00172; A61B 1/0006; A61B 1/00165; A61B 1/042; A61B 1/07;
(Continued)

(56) References Cited

U.S. PATENT DOCUMENTS

| 3,964,315 A | 6/1976 | Engelhardt |
| 5,414,940 A | 5/1995 | Sturdevant |

(Continued)

FOREIGN PATENT DOCUMENTS

| JP | 2006-256151 A | 9/2006 |
| JP | 2007-093644 A | 4/2007 |

(Continued)

OTHER PUBLICATIONS

T. Ando et al. (2008; retrieved Sep. 2017), "High-speed AFM and nano-visualization of biomolecular processes," Pflügers Archiv—European Journal of Physiology, 456(1):211-225.
(Continued)

*Primary Examiner* — Euncha P Cherry
(74) *Attorney, Agent, or Firm* — Christensen O'Connor Johnson Kindness PLLC

(57) ABSTRACT

Improved systems, methods, and devices relating to optical fiber scanners are provided. In one aspect, a scanning apparatus includes an optical fiber and a piezoelectric actuator coupled to the optical fiber to deflect a distal end of the optical fiber in a scanning pattern. The apparatus can include drive circuitry coupled to the piezoelectric actuator, sense circuitry electrically coupled to the piezoelectric actuator and the drive circuitry to determine displacement of the piezoelectric actuator, and a processor coupled to the drive circuitry and the sense circuitry to drive the piezoelectric actuator in response to the displacement.

10 Claims, 32 Drawing Sheets

Related U.S. Application Data

(60) Provisional application No. 61/921,151, filed on Dec. 27, 2013, provisional application No. 61/988,110, filed on May 2, 2014.

(51) Int. Cl.

| | | |
|---|---|---|
| *A61B 1/04* | (2006.01) | |
| *A61B 1/07* | (2006.01) | |
| *G02B 26/10* | (2006.01) | |
| *H01L 41/04* | (2006.01) | |
| *H01L 41/09* | (2006.01) | |
| *A61N 5/06* | (2006.01) | |

(52) U.S. Cl.
CPC ............... *A61B 1/042* (2013.01); *A61B 1/07* (2013.01); *G02B 26/103* (2013.01); *H01L 41/042* (2013.01); *H01L 41/0926* (2013.01); *A61N 2005/063* (2013.01)

(58) Field of Classification Search
CPC . H01L 41/042; H01L 41/0926; G02B 26/103; A61N 2005/063
USPC ........................................................ 359/200.8
See application file for complete search history.

(56) References Cited

U.S. PATENT DOCUMENTS

| | | | |
|---|---|---|---|
| 5,651,366 | A | 7/1997 | Liang et al. |
| 5,907,146 | A | 5/1999 | Bridgelall et al. |
| 6,233,495 | B1 | 5/2001 | Chen |
| 6,845,190 | B1 | 1/2005 | Smithwick et al. |
| 2002/0074512 | A1 | 6/2002 | Montagu et al. |
| 2003/0025687 | A1 | 2/2003 | Shino et al. |
| 2004/0095297 | A1 | 5/2004 | Libsch |
| 2005/0009197 | A1 | 1/2005 | Adams et al. |
| 2007/0019906 | A1 | 1/2007 | Melville |
| 2007/0015959 | A1 | 7/2007 | Yamada |
| 2008/0058629 | A1 | 3/2008 | Seibel et al. |
| 2009/0026888 | A1 | 1/2009 | Melville |
| 2009/0092364 | A1 | 4/2009 | Johnston et al. |
| 2009/0316116 | A1 | 12/2009 | Melville et al. |
| 2013/0018487 | A1 | 1/2013 | Gao |
| 2016/0324403 | A1 | 11/2016 | Yeoh et al. |

FOREIGN PATENT DOCUMENTS

| | | | |
|---|---|---|---|
| JP | 2008-514344 | A | 5/2008 |
| JP | 2010-534862 | A | 11/2010 |
| JP | 2011-106936 | A | 6/2011 |
| JP | 2011-154196 | A | 8/2011 |

OTHER PUBLICATIONS

T. Ando et al. (epub Jan. 2014), "Filming Biomolecular Processes by High-Speed Atomic Force Microscopy," Chemical Reviews, 114(6):3120-3188.
QYJ Smithwick et al. (Mar. 2004), "A nonlinear state-space model of a resonating single fiber scanner for tracking control: Theory and experiment," Journal of Dynamic Systems, Measurement and Control, Transactions of the ASME, 126(1):88-101.
QY Smithwick (Aug. 2002), "Modeling and control of the single fiber scanning endoscope," Ph.D. Thesis, University of Washington, 375 pages.
PF Pai and AH Nayfeh (1990; retrieved Sep. 2017), "Non-linear non-planar oscillations of a cantilever beam under lateral base excitations," International Journal of Non-Linear Mechanics, 25(5):455-474.
MRM Crespo da Silva and CC Glynn (Jan. 1978), "Nonlinear flexural-flexural-torsional dynamics of inextensional beam. I. Equations of motion," Journal of Structural Mechanics, 6(4):437-448.
MRM Crespo da Silva and CC Glynn (Jan. 1978), "Nonlinear flexural-flexural-torsional dynamics of inextensional beam. II. Forced motions," Journal of Structural Mechanics, 6(4):449-461.
QYJ Smithwick et al. (Jan. 2010), "A hybrid nonlinear adaptive tracking controller for a resonating fiber microscanner," Journal of Dynamic Systems, Measurement and Control, Transactions of the ASME, 132(1):1-13.
QYJ Smithwick et al. (Dec. 2006), "An error space controller for a resonating fiber scanner: Simulation and Implementation," Journal of Dynamic Systems, Measurement and Control, Transactions of the ASME, 128(4):899-913.
MJ Kundrat (Mar. 2010), "High performance open loop control for fiber scanner imaging and display systems," Ph.D. Thesis, University of Washington, 131 pages.
MJ Kundrat (Dec. 2004), "A nonlinear numerical model of a base excited cantilever beam," Master's Thesis, University of Washington, 75 pages.
S. Devasia et al. (Jul. 1996), "Nonlinear inversion-based output tracking," IEEE Transactions on Automatic Control, 41(7):930-942.
M. Norrlöf and S. Gunnarsson (Aug. 2002), "Experimental comparison of some classical iterative learning control algorithms," IEEE Transactions on Robotics and Automation, 18(4):636-641.
S. Gunnarsson and M. Norrlöf (Dec. 2001), "On the design of ILC algorithms using optimization," Automatica, 37(12):2011-2016.
NK Gupta (Nov. 1980), "Frequency-shaped cost functionals—Extension of linear-quadratic-Gaussian design methods," Journal of Guidance, Control, and Dynamics, 3(6):529-535.
R. Brinkerhoff and S. Devasia (Mar.-Apr. 2000), "Output tracking for actuator deficient/redundant systems: Multiple piezoactuator example," Journal of Guidance, Control, and Dynamics 23(2):370-373.
C. Yang et al. (Jul. 2014), "Target-to-Background Enhancement in Multispectral Endoscopy with Real-time Background Autofluorescence Mitigation for Quantitative Molecular Imaging," Journal of Biomedical Optics, 19(7):076014.
TD Soper et al. (Mar. 2010), "In vivo validation of a hybrid tracking system for navigation of an ultrathin bronchoscope within peripheral airways," IEEE Transactions on Biomedical Engineering, 57(3):736-745.
TD Soper et al. (Jun. 2012), "Surface Mosaics of the Bladder Reconstructed from Endoscopic Video for Automated Surveillance," IEEE Transactions on Biomedical Engineering, 59(6)1670-1680.
MH Woldetensae et al. (2013; retrieved Sep. 2017), "Fluorescence image-guided photodynamic therapy of cancer cells using a scanning fiber endoscope," Proceedings of SPIE, Optical Fibers and Sensors for Medical Diagnostics and Treatment Applications XIII, 8576:85760L.
Z. Wang and AC Bovik (2006; retrieved Sep. 2017), "Modern image quality assessment," Synthesis Lectures on Image, Video, and Multimedia Processing, 156 pages.
BT Schowengerdt et al. (2009; retrieved Sep. 2017), "37.1: Invited Paper; 1-mm Diameter, Full-color Scanning Fiber Pico Projector," SID Symposium Digest of Technical Papers. 40(1):522-525.
M. Freeman et al. (May 2009), "Scanned Laser Pico-Projectors: Seeing the Big Picture (with a Small Device)," Optics and Photonics News, 20(5)28-34.
Bionumbers (retrieved Sep. 2017) [Search for "blink"], available online at: http://bionumbers.hms.harvard.edu/search.aspx?log=y&task=searchbytrmorg&trm=blink.
Wikipedia.org (retrieved Sep. 2017) "Blinking," available online at: http://en.wikipedia.org/wiki/Blink.
Scholarpedia.org (retrieved Sep. 2017), "Human saccadic eye movements," available online at: http://www.scholarpedia.org/article/Human_saccadic_eye_movements.
RC Bryant et al. (2004; retrieved Sep. 2017), "Low-cost wearable low-vision aid using a handmade retinal light-scanning microdisplay," Journal of the Society for Information Display, 12(4):397-404.
Japanese Office Action dated Jul. 24, 2017, for Japanese Application No. 2016-542944, filed Dec. 24, 2014, 8 pages.
International Search Report and Written Opinion dated Apr. 29, 2015, for International Application No. PCT/US2014/072372, filed Dec. 24, 2014, 12 pages.

(56) References Cited

OTHER PUBLICATIONS

Extended European Search Report dated Aug. 23, 2017, for European Application No. 14875155.5, filed Dec. 24, 2014, 7 pages.
CM Lee et al. (Jun. 2010), "Scanning Fiber Endoscopy with Highly Flexible, 1 mm Catheterscopes for Wide-Field, Full-Color Imaging," Journal of Biophotonics, 3(5-6)385-407.
MW Hyer (Apr. 1979), "Whirling of a Base-Excited Cantilever Beam," Journal of the Acoustical Society of America, 65(4):931-939.
EC Haight and WW King (Sep. 1972), "Stability of Nonlinear Oscillations of an Elastic Rod," Journal of the Acoustical Society of America, 52(3):899-911.
MJ Kundrat et al. (Apr. 2011), "High Performance Open Loop Control of Scanning with a Small Cylindrical Cantilever Beam," Journal of Sound and Vibration, 330(8)1762-1771.
SO Moheimani and YK Yong (Jul. 2008), "Simultaneous Sensing and Actuation with a Piezoelectric Tube Scanner," Review of Scientific Instruments, 79(7):073702.
YK Yong et al. (Mar. 2010), "Atomic Force Microscopy with a 12-Electrode Piezoelectric Tube Scanner," Review of Scientific Instruments, 81(3):033701.
JJ Dosch et al. (Jan. 1992), "A Self-Sensing Piezoelectric Actuator for Collocated Control," Journal of Intelligent Material Systems and Structures, 3(1):166-185.
S. Kuiper and G.. Schitter (Sep. 2010), "Active Damping of a Piezoelectric Tube Scanner Using Self-Sensing Piezo Actuation," Mechatronics, 20(6):656-665.
MJ Kundrat et al. (Sep. 2011), "Method to Achieve High Frame Rates in a Scanning Fiber Endoscope," Journal of Medical Devices, 5(3):034501.
KJ Astrom and B. Wittenmark (2008; retrieved Sep. 2017), Adaptive Control, Dover Publications: Mineola, NY, pp. 41-56.
QYJ Smithwick et al. (2003; retrieved Sep. 2017), "54.3: Modeling and Control of the Resonant Fiber Scanner for Laser Scanning Display or Acquisition," SID Symposium Digest of Technical Papers, 34(1):1455-1457.
GM Clayton and S. Devasia (2005; retrieved Sep. 2017), "Image-based compensation of dynamic effects in scanning tunneling microscopes," Nanotechnology, 16(6):809-818.
GM Clayton and S. Devasia (Aug. 2007), "Iterative image-based modeling and control for higher scanning probe microscope performance," Review of Scientific Instruments, vol. 78(8):083704.
YD Zhang et al. (Mar. 2009), "Image-Based Hysteresis Modeling And Compensation For An AFM Piezo-Scanner," Asian Journal of Control, 11(2):166-174.
AJ Fleming et al. (Nov. 2008), "Sensor Fusion for Improved Control of Piezoelectric Tube Scanners," IEEE Transactions On Control Systems Technology, 16(6):1265-1276.
M. Bazghaleh et al. (Aug. 2013), "A novel digital charge-based displacement estimator for sensorless control of a grounded-load piezoelectric tube actuator," Sensors & Actuators: A. Physical, 198:91-98.
AJ Fleming and SOR Moheimani (Jul. 2005), "A grounded-load charge amplifier for reducing hysteresis in piezoelectric tube scanners," Review of Scientific Instruments, 76(7):073707.
CV Newcomb and I. Flinn (Jan. 1982), "Improving the linearity of piezoelectric ceramic actuators," Electronics Letters, 18(11):442-444.
M. Bazghaleh et al. (May 2013), "A new hybrid method for sensorless control of piezoelectric actuators," Sensors and Actuators, A: Physical, 194:25-30.
GE Simmers et al. (Dec. 2004), "Improved piezoelectric self-sensing actuation," Journal of Intelligent Material Systems and Structures, 15(12):941-953.
A. Badel et al. (Mar. 2008), "Self-sensing high speed controller for piezoelectric actuator," Journal of Intelligent Material Systems and Structures, 19(3):395-405.
CJ Chen (Jan. 1992), "Electromechanical deflections of piezoelectric tubes with quartered electrodes," Applied Physics Letters, 60(1):132-134.
M. Leung et al. (Aug. 2009), "Tip deflection calculations of small-diameter thin-walled piezoelectric tubes," Ceramics International, 35(6):2409-2414.
WF Smith and BW Axelrod (Apr. 2000), "Measurements of the double piezoelectric effect," Review of Scientific Instruments, 71(4):1772-1775.
L. Jones et al. (1994; retrieved Sep. 2017), "Self-sensing control as applied to a PZT stack actuator used as a micropositioner," Smart Materials and Structures, 3(2):147-156.
AJ Fleming and SOR Moheimani (Jan. 2006), "Sensorless vibration suppression and scan compensation for piezoelectric tube nanopositioners," IEEE Transactions On Control Systems Technology, 14(1):33-44.
ME Taylor (Jan. 1993), "Dynamics of piezoelectric tube scanners for scanning probe microscopy," Review of Scientific Instruments, 64(1):154-158.
Y. Ma et al. (Jun. 2009), "Static and dynamic analysis of a four-tube piezoelectric actuator," Review of Scientific Instruments, 80(6):065101.
AK Jha and DJ Inman (Jan. 2002), "Piezoelectric actuator and sensor models for an inflated toroidal shell," Mechanical Systems and Signal Processing, 16(1):97-122.
ZL Lai et al. (Aug. 2013), "A novel similarity-based hysteresis empirical model for piezoceramic actuators," Sensors and Actuators, A: Physical, 197:150-165.
Y. Pasco and A. Berry (Jan. 2006), "Consideration of piezoceramic actuator nonlinearity in the active isolation of deterministic vibration," Journal of Sound and Vibration, 289(3):481-508.
D. Croft et al. (Mar. 2001), "Creep, hysteresis, and vibration compensation for piezoactuators: Atomic force microscopy application," Journal of Dynamic Systems Measurement and Control-Transactions of the ASME, 123(1):35-43.
R. Shahnazi et al. (Aug. 2010), "Adaptive fuzzy output feedback control for a class of uncertain nonlinear systems with unknown backlash-like hysteresis," Communications in Nonlinear Science and Numerical Simulation, 15(8):2206-2221.
RL Dong et al. (May 2008), "A neural networks based model for rate-dependent hysteresis for piezoceramic actuators," Sensors and Actuators, A: Physical, 143(2):370-376.
IA Mahmood and SOR Moheimani (Jun. 2009), "Making a commercial atomic force microscope more accurate and faster using positive position feedback control," Review of Scientific Instruments, 80(6):063705.
E. Guliyev et al. (Jun. 2012), "Quasi-monolithic integration of silicon-mems with piezoelectric actuators for high-speed non-contact atomic force microscopy," Measurement Science and Technology, 23(7):074012.
AJ Fleming and KK Leang (Nov. 2008), "Charge drives for scanning probe microscope positioning stages," Ultramicroscopy, 108(12):1551-1557.
M. Bazghaleh et al. (Apr. 2014), "Implementation and analysis of an innovative digital charge amplifier for hysteresis reduction in piezoelectric stack actuators," Review of Scientific Instruments, 85(4):045005.
Y. Wang et al. (2009; retrieved Sep. 2017), "Survey on iterative learning control, repetitive control, and run-to-run control," Journal of Process Control, 19(10)1589-1600.
DA Bristow et al. (Jun. 2006), "A survey of iterative learning control," IEEE Control Systems, 26(3):96-114.
PH Meckl (1988; retrieved Sep. 2017), "Control of Vibration in Mechanical Systems Using Shaped Reference Inputs," Technical Report No. 1018, Massachusetts Institute of Technology Cambridge Artificial Intelligence Lab, 230 pages.
GM Clayton et al. (Nov. 2009), "A review of feedforward control approaches in nanopositioning for high-speed SPM," Journal of Dynamic Systems, Measurement and Control, Transactions of the ASME, 131(6):061101.
J. Ghosh and B. Paden (Jun. 2000), "Pseudo-inverse based iterative learning control for plants with unmodeled dynamics," Proceedings of the American Control Conference, 1:472-476.
J. Ghosh and B. Paden (Mar. 2001), "Iterative learning control for nonlinear nonminimum phase plants," ASME Journal of Dynamic Systems, Measurement and Control, 123:21-30.

(56) References Cited

OTHER PUBLICATIONS

X. Wang and D. Chen (Oct. 2002), "Robust inversion-based learning control for nonminimum phase system," Proceedings of the IEEE International Conference on Systems, Man, and Cybernetics, 3:489-494.
S. Tien et al. (Nov. 2005), "Iterative control of dynamics-coupling-caused errors in piezoscanners during high-speed AFM operation," IEEE Transactions on Control Systems Technology, 13(6):921-931.
BT Schowengerdt et al. (2008; retrieved Sep. 2017), "Miniature wide-throw-angle scanning fiber projection display," SID International Symposium—Digest of Technical Papers, 39(3):2102-2105.
European Office Action dated Jul. 20, 2018, for European Application No. 14875155.5, filed Dec. 24, 2014, 3 pages.
Japanese Office Action and Translation dated Feb. 25, 2019 for Japanese Application No. 2018-030639, filed Dec. 24, 2014, 4 pages.
European Office Action dated Mar. 4, 2019 for European Application No. 14875155.5, filed Dec. 24, 2014, 4 pages.
Huang et al., "A wearable yarn-based piezo-resistive sensor," Sensors and Actuators A, vol. 141, 2008, pp. 396-403.

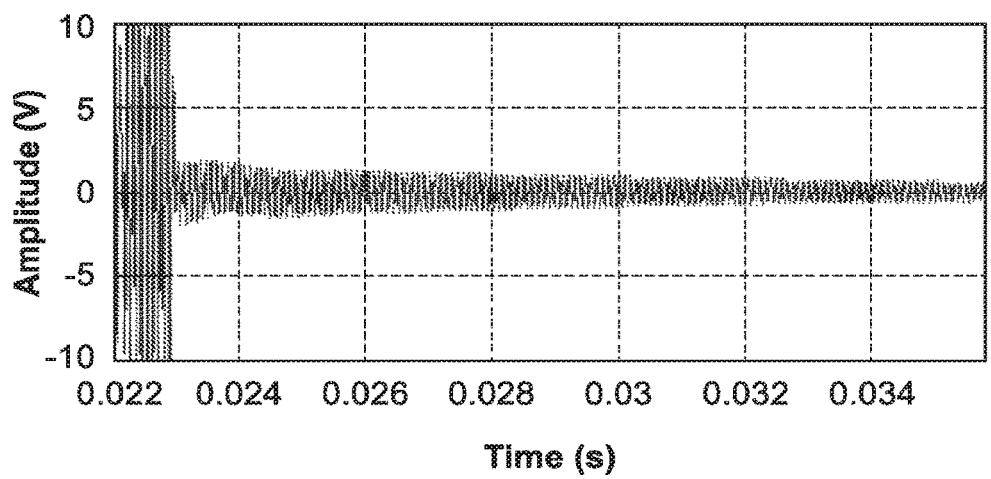
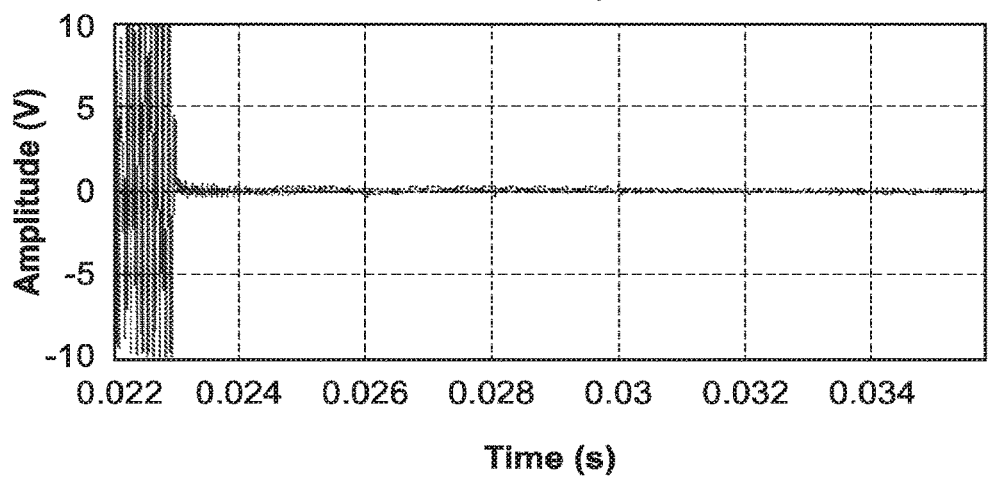
FIG. 19D

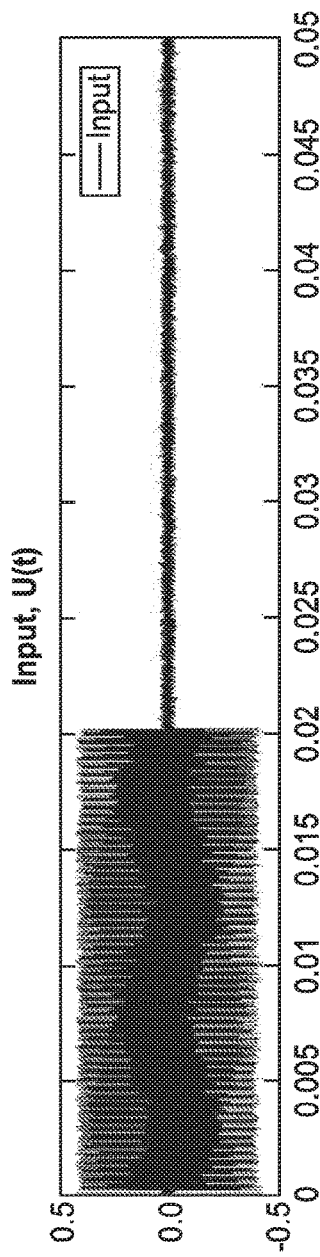
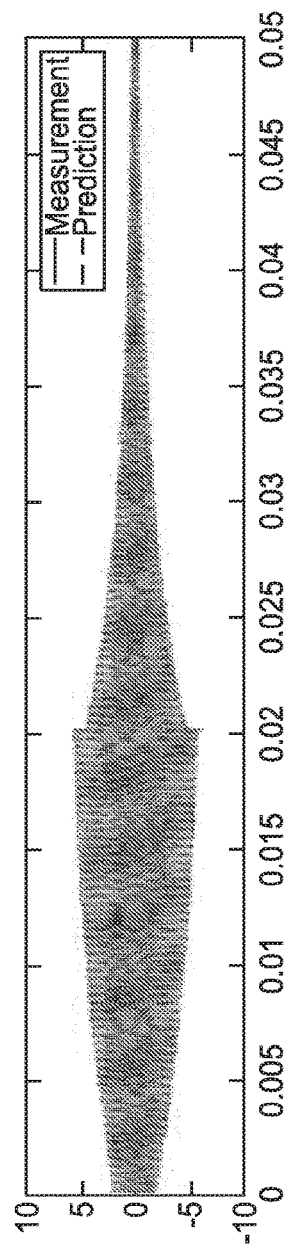
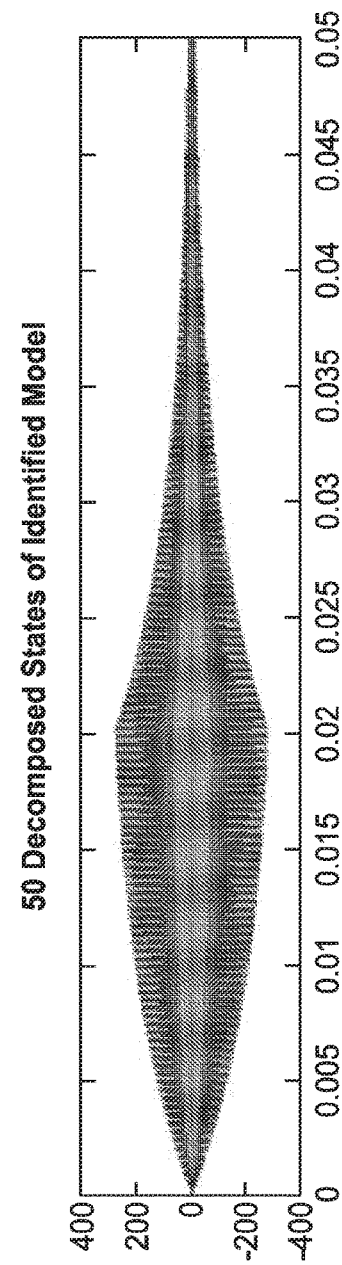

ADAPTIVE CONTROL OF A FIBER SCANNER WITH PIEZOELECTRIC SENSING

CROSS-REFERENCE

This application is a continuation of U.S. application Ser. No. 15/107,894, filed Jun. 23, 2016, which is the U.S. National Stage entry under 35 U.S.C § 371 of international application PCT/US2014/072372, filed Dec. 24, 2014, which claims the benefit of U.S. Provisional Application Nos. 61/921,151, filed Dec. 27, 2013 and 61/988,110, filed May 2, 2014, which applications are incorporated herein by reference.

STATEMENT AS TO FEDERALLY SPONSORED RESEARCH

This invention was made with the support of the United States government under CA094303-R33 awarded by the National Institutes of Health. The government has certain rights in the invention.

BACKGROUND

The present invention relates generally to optical scanning. Although specific reference is made to optical scanning in the context of an endoscope, the embodiments as disclosed herein will find applications in many fields such as optical displays, optical projectors, and imaging devices.

Prior methods and apparatus for scanning and displaying images can be less than ideal in at least some respects. Prior display devices such as image projectors and displays can be somewhat larger than would be ideal. Although scanning devices have been proposed, the prior scanning devices may have less than ideal image quality and can be somewhat larger than would be ideal.

Scanning devices can be used with minimally invasive medical procedures for various diagnostic and therapeutic applications so as to minimize tissue trauma, patient risk, and recovery time. During such procedures, the practitioner can visually inspect tissues within the patient's body using an endoscope. Conventional endoscopes may utilize a bundle of optical fibers to transmit light captured from an imaging plane to a detector outside the body. In some instances, the relatively large diameter of conventional endoscopes may preclude use in narrow passages and/or small spaces within the body. One significant improvement has been to decrease the diameter by reducing the number of optical fibers within the imaging bundle, for example with a scanning fiber endoscope.

Scanning optical fibers have been proposed in other fields in addition to endoscopy. However, the deficiencies of prior scanning optical fibers and can limit the utility and benefits of the prior scanning optical fiber devices, for example as used for imaging. Although prior scanning optical fiber imaging devices can decrease size, the prior scanning optical fiber scanners can be less than ideal. In some instances, the duty cycle and repeatability of prior scanning fiber devices may be less than ideal, which can be related to decreased image quality, increased power consumption and lower frame rates, for example. Additionally, the prior scanning fiber devices may be sensitive to changes in environmental conditions, such as temperature, and can be somewhat less robust than would be ideal. Also, as the fiber and actuator age, the resonant and deflection properties can change. Although the scanning fiber device can be recalibrated, the prior recalibration methods and apparatus can be somewhat less than ideal. Although position sensing optical detectors can be used to calibrate the fiber position of scanning fiber endoscopes, such calibration can somewhat cumbersome to use, and may not be well suited for use with at least some applications.

In light of the above, improved optical scanning devices are needed. Ideally such improved devices would be compact, capable of high resolution scanning and large display areas, provide quality images and measurements, capable of operating in many environments, and be well suited for use in many applications.

SUMMARY

Embodiments of the present invention provide improved scanning optical fiber methods and apparatus. The embodiments disclosed herein can provide improved optical fiber scanners with reduced size and cost, higher accuracy and precision of scanning control, and enhanced flexibility of use. The optical fiber scanners described herein can utilize a piezoelectric actuator to drive a cantilevered optical fiber so as to scan the fiber in accordance with a desired scanning pattern. In many embodiments, the scanning apparatus comprises one or more of adaptive control instructions embodied on a tangible medium, or improved sense circuitry to measure the scanning apparatus, and combinations thereof. In some embodiments, self-sensing circuitry comprises the piezoelectric actuator in order to measure displacement of the actuator and determine displacement of the fiber. The sense circuitry has the advantage of allowing the processor of the scanner to determine appropriate scanning parameters in order to improve control of the scanning fiber, and the sense circuitry can be used to calibrate the scanner. In many embodiments, the sense circuitry allows the scanner to be used with many applications where the resonance properties of the scanning apparatus change over time, such as applications where the temperature can change. In many embodiments, the scanning apparatus comprises a control configuration capable of providing high frame rates with decreased duty cycles, such as an adaptive frame sequential feedforward control configuration, or pixel by pixel feedback control configuration.

In many embodiments, the scanning apparatus is configured to determine the position of the scanning optical fiber without the use of external sensors, thereby reducing the size, cost, and complexity of such scanning systems. In many embodiments, the self-sensing data can be measured during actuation of the optical fiber, which can increase the duty cycle and frame rates of the optical fiber scanner. The self-sensing data can be used in control loops in order to provide adaptive control of the system, such that changes in system parameters can be tracked and compensated for in order to maintain control over the optical fiber and to inhibit variation related to manufacturing variance or operating conditions. In many embodiments, the calibration circuitry allows the optical fiber scanner apparatus to be used in one or more of many environmental conditions with decreased loss of image quality.

In a first aspect, a scanning apparatus includes an optical fiber and a piezoelectric actuator coupled to the optical fiber to deflect a distal end of the optical fiber in a scanning pattern. The apparatus can include drive circuitry coupled to the piezoelectric actuator and a processor coupled to the drive circuitry and sense circuitry to drive the piezoelectric actuator in response to displacement of the piezoelectric actuator. The sense circuitry can be electrically coupled to the piezoelectric actuator and the drive circuitry to determine the displacement of the piezoelectric actuator. The scanning apparatus can comprise the sense circuitry. The drive circuitry can be configured to generate piezoelectric drive signals, and the sense circuitry can be configured to obtain piezoelectric displacement signals. The sense circuitry can be configured to isolate the piezoelectric displacement signals from piezoelectric drive signals when the drive circuitry drives the piezoelectric actuator with the piezoelectric drive signals. At least one of the sense circuitry or drive circuitry can include bipolar circuitry.

The piezoelectric actuator can be configured in one or more of many ways. In many embodiments, the piezoelectric actuator comprises one or more of the following: a piezoelectric tube, a piezoelectric stack actuator, or a piezoelectric stack actuator with a flexure. Various types of signals can be applied to the piezoelectric actuator to drive the actuator and optical fiber. Similarly, the types of signals measured by the sense circuitry can also be varied. For example, the piezoelectric drive signals can include one or more of piezoelectric voltage drive signals or piezoelectric charge drive signals, and the piezoelectric displacement signals comprise one or more of piezoelectric voltage displacement signals or piezoelectric charge displacement signals.

The components can be coupled to each other in one or more of many arrangements. In many embodiments, the piezoelectric actuator can include a first input, such as an electrode, corresponding to a first axis of movement along a first physical dimension and a second input corresponding to a second axis of movement along a second physical dimension. The drive circuitry may comprise first drive circuitry coupled to the first input and second drive circuitry coupled to the second input. The sense circuitry may comprise first sense circuitry coupled to the first input and second sense circuitry coupled to the second input.

The sense circuitry may comprise a combination of circuit elements to determine displacement of the piezoelectric actuator. In many embodiments, the sense circuitry comprises a bridge circuit having a balance leg and an actuator leg in parallel with the balance leg. The actuator leg comprises the piezoelectric actuator, and the balance leg comprises one or more components having one or more electrical properties, such as a capacitance, similar to the piezoelectric actuator in order to balance the piezoelectric actuator. The drive circuitry can be connected to the balance leg and the actuator leg in order to drive the balance leg in parallel with the actuator leg. The balance leg may comprise a first plurality of resistors and a first capacitor coupled between the first plurality of resistors. The actuator leg may comprise a second plurality of resistors and a second capacitor coupled between the second plurality of resistors. The balance leg and the actuator leg can be configured to isolate a piezoelectric displacement signal from a piezoelectric drive signal.

In many embodiments, the first capacitor comprises a first plurality of capacitors and the second capacitor comprises a second plurality of capacitors. The first plurality of resistors may comprise a first plurality of pairs of adjacent resistors and the second plurality of resistors can include a second plurality of pairs of adjacent resistors. The first plurality of capacitors can be connected between the first plurality of pairs of adjacent resistors and the second plurality of capacitors can be connected between the second plurality of pairs of adjacent resistors. The first plurality of capacitors may comprise a balance capacitor connected in series between the first plurality of pairs of adjacent resistors, and the second plurality of capacitors may comprise the piezoelectric actuator connected in series between the second plurality of pairs of adjacent resistors, in order to in order to isolate the piezoelectric displacement signal from the piezoelectric drive signal.

In many embodiments, one or more components of the sense circuitry correspond to one or more components of the scanning apparatus. In many embodiments, the sense circuitry comprises one or more components corresponding to one or more of a capacitance or a resistance of a wire electrically coupling the sense circuitry to the piezoelectric actuator. The sense circuitry may comprise a bridge circuit having a balance leg and an actuator leg. The balance leg may comprise one or more of a first capacitor having a first charge (Qw2) corresponding to a wire, a first plurality of resistors each having a resistance (Rw) corresponding to the wire, or a balance capacitor having a balance charge (Qb). The actuator leg can include one or more of a second capacitor having a second charge (Qw1) corresponding to a wire, a second plurality of resistors each having a resistance (Rw) corresponding to a wire, or a piezoelectric capacitor having a piezoelectric charge (Qp) opposite the balance charge.

In many embodiments a processor comprises instructions to determine parameters of the scanning apparatus and to control operation of the scanning apparatus. In many embodiments, the processor comprises instructions to determine first and second eigendirections of the piezoelectric actuator in response to isolated displacement signals of the piezoelectric actuator driven along first and second physical axes. In many embodiments, the processor comprises instructions to control displacement of the distal end of the optical fiber with one or more of the following: an adaptive control loop, an adaptive feedforward control loop, a frame sequential feedback control loop, or a pixel sequential feedback control loop. The processor can include instructions to control displacement of the distal end of the optical fiber with the adaptive (feedforward) control loop, and to identify one or more control parameters with signals from the sense circuitry. Furthermore, the processor can include instructions to update the one or more control parameters of the adaptive (feedforward) control loop for each of a plurality of sequential image frames. The one or more control parameters of the adaptive (feedforward) control loop can include one or more of a first eigendirection, a second eigendirection, a first damped resonance frequency, a second damped resonance frequency, a first phase-at-braking or a second phase-at-braking, in response to a signal from the sense circuitry.

Alternatively or in combination, the processor may comprise instructions to control displacement of the distal end of the optical fiber with the pixel sequential feedback control loop and to identify one or more control parameters with signals from the sense circuitry. The processor may comprise instructions to update the one or more control parameters of the pixel sequential feedback control loop for each pixel of a sequential image frame. The processor may comprise instructions to direct the distal end of the optical fiber to a sequence of pixel locations and to measure displacement of the actuator at the pixel locations and determine an error at each of the pixel locations and adjust a drive signal of the drive circuitry in real time in order to correct the error at said each of the plurality of pixel locations.

The processor may comprise instructions embodying one or more modeling approaches in order to improve the accuracy and precision of scanning control. In many embodiments, the processor comprises instructions to control displacement of the distal end of the optical fiber with a model comprising one or more of a state space electromechanical model or a vibration modal model. In many embodiments, the model comprises the state space electromechanical model, and one or more parameters of the state space electromechanical correspond to one or more of a stiffness of the piezoelectric actuator, a mass of the piezoelectric actuator, a damping of the piezoelectric actuator, a stiffness of the optical fiber, a mass of the optical fiber, or a damping of the optical fiber. Alternatively or in combination, the model may comprise the vibration modal model and one or more parameters of the general vibration mode model corresponding to one or more vibration modes of the piezoelectric actuator and/or optical fiber.

One or more of many techniques can be used to identify and determine optimization parameters of the control inputs for directing the scanning of the optical fiber. The processor may comprise instructions to identify the control parameters using one or more of a batch least squares regression or a modal matrix transformation. Alternatively or in combination, the processor may comprise instructions to determine a scan trajectory for the optical fiber such that the scanning pattern fills a field of view of an image and reduces frequency content of unwanted vibration modes of the optical fiber having frequencies away from frequencies of a selected vibration mode of the optical fiber. In many embodiments, the processor comprises instructions to determine a scan trajectory for the optical fiber such that the scanning pattern fills substantially a field of view of an image and reduces frequency content of unwanted vibration modes of the optical fiber having frequencies away from frequencies of a selected vibration mode of the optical fiber.

In many embodiments, the processor comprises instructions to progressively adjust a drive signal based on a real-time feedback control signal. The drive signal can be adjusted on a slower time scale than the real-time feedback control signal, the slower time scale determined based at least in part on system repeatability among sweeps of the actuator.

A duty cycle of the scanning apparatus can be within a range between any two of the following: 70%, 75%, 80%, 85%, 90%, 95%, 99%, 99.9%, 99.99%, or 99.999%.

In many embodiments, the optical fiber is represented by a plurality of mechanical components each characterized by one or more of a mass, stiffness, or damping, and the piezoelectric actuator can be represented by a plurality of mechanical components each characterized by one or more of a mass, stiffness, or damping. A sensed voltage obtained by the sense circuitry may correspond to an energy output of the mechanical components of the optical fiber and/or piezoelectric actuator.

Other objects and features of the present invention will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 19D illustrates an exemplary scanner displacement profile, in accordance with embodiments;

FIGS. 20A through 20C illustrate exemplary input data and measured output data, in accordance with embodiments;

DETAILED DESCRIPTION

Figure 1:
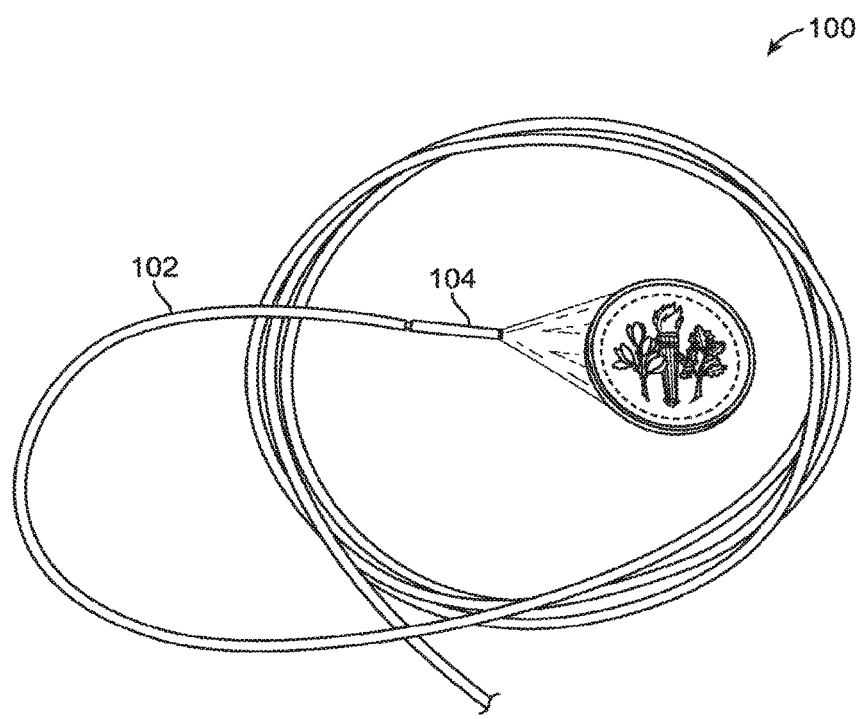
FIG. 1 shows an ultrathin scanning fiber endoscope (SFE), in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

As used herein A and/or B encompasses one or more of A or B, and combinations thereof such as A and B.

The scanning fiber apparatus can be used for one or more of imaging or treatment of a material such as tissue with light energy.

The embodiments disclosed herein can be combined in one or more of many ways to provide improved optical fiber scanners. An optical fiber scanner can include a cantilevered optical fiber (also referred to herein as a "fiber optic") driven by a piezoelectric actuator so as to scan light onto a target surface in a predetermined pattern. Such optical fiber scanners can be used for a variety of applications, including image acquisition as well as image display. In some embodiments, the scanners described herein can be coupled to self-sensing circuitry so as to enable the piezoelectric actuator to serve both as an actuator and as a sensor for the scanning optical fiber. The self-sensed positional data obtained by the piezoelectric actuator can be used in a variety of adaptive control schemes (e.g., adaptive feedforward control schemes) that can be used to adjust the scanner control inputs to compensate for variable operating conditions (e.g., changes in temperature). Advantageously, the approaches described herein provide self-sensed positional data for the piezoelectric actuator and/or optical fiber independently of additional sensor components (e.g., position sensing detectors) that may otherwise increase the cost and size of the optical fiber scanner. Furthermore, the techniques for adaptive (feedforward) control provided herein enable the optical fiber scanner to be used in diverse operating conditions, thus enabling improved accuracy and flexibility of the scanner for imaging applications.

Although embodiments herein are described in the context of image acquisition and imaging systems, this is not intended to be limiting, and it shall be understood that the disclosed embodiments can be used for any suitable application utilizing scanning optical fibers, such as fiber-scanned displays for compact video displays and projectors (e.g., head-mounted displays, eye projection modalities). For example, in some embodiments, the techniques described herein are applied for use in a fiber scanned display/projector operated at about 111 frames per second (fps), about 100% duty cycle, and at 2× interleave with minimal distortion.

As used herein like characters identify like elements.

Scanning Optical Fiber Systems

FIG. 1 shows an ultrathin scanning fiber endoscope (SFE) 100, in accordance with embodiments. The SFE 100 can be inserted into a patient's body via a natural opening or surgical port to enable a medical practitioner to visually inspect internal tissues. The SFE 100 includes a long, flexible shaft 102 and a distal tip 104 housing a scanning optical fiber assembly. The SFE can have dimensions suitable for insertion into small diameter passages and/or spaces within the body. For example, the outer diameter of the SFE can be smaller than the outer diameter of a conventional endoscope, such as less than or equal to approximately 2 mm, 1.5 mm, 1.2 mm, or 1 mm.

Figure 2:
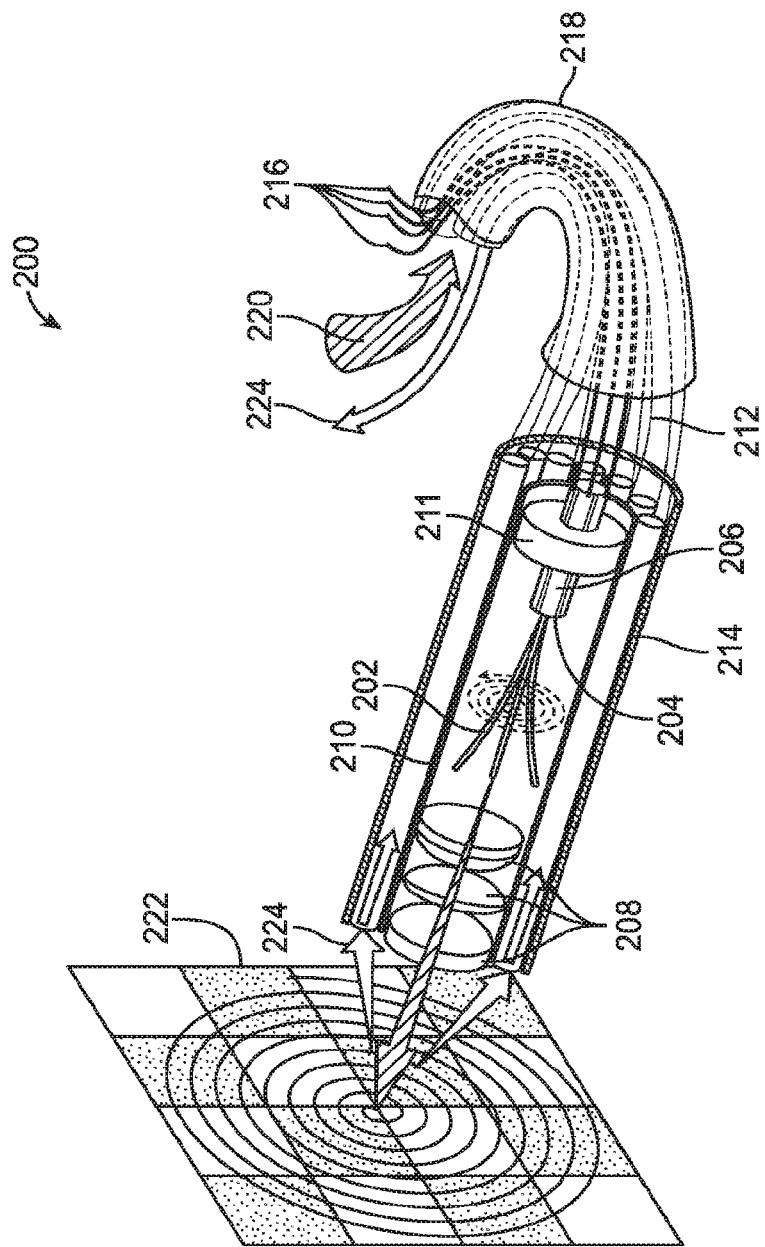
FIG. 2 shows a scanning optical fiber assembly in the distal tip of a SFE, in accordance with embodiments.

FIG. 2 shows a scanning optical fiber assembly 200 in the distal tip of a SFE, in accordance with embodiments. The scanning assembly 200 can include a cantilevered scanning optical fiber 202, a piezoelectric actuator 204, a plurality of electrical inputs (e.g., electrodes 206) of the actuator 204, and one or more lenses 208, all contained within a first housing 210. A mounting collar 211 can be disposed circumferentially around the piezoelectric actuator 204 so as to support the piezoelectric actuator 204 within the first housing 210. A plurality of light collection optical fibers 212 can be positioned around the first housing 210 and within a second housing 214. The scanning optical fiber 202, light collection optical fibers 212, and a plurality of electrode wires 216 can extend through a flexible shaft 218 coupled to the distal tip of the SFE.

Various types of piezoelectric devices can be used for the piezoelectric actuator 204, such as a piezoelectric tube, a piezoelectric stack actuator, a piezoelectric stack actuator with one or more flexures (e.g., to amplify actuation), or combinations thereof. In some embodiments, the piezoelectric actuator 204 can be configured as a hollow four-quadrant piezoelectric tube actuator, with the scanning optical fiber 202 running through the tube. Optionally, the scanning optical fiber 202 can be coupled to the distal portion of the piezoelectric actuator 204 be a fiber adhesive attachment (not shown). Light provided by a light source external to the patient's body, such as laser illumination 220, can be directed through the scanning optical fiber 202 and exit its distal end so as to illuminate a portion of a target surface (e.g., illumination plane 222) adjacent the scanning assembly 200. The lenses 208 can be used to collimate or focus the light leaving the optical fiber 202 before it reaches the target surface. In some embodiments, the lenses 208 can also bend the collimated or focused light further away from the central axis of the scanning assembly 200, thereby increasing the field of view of the SFE. For example, the field of view of an SFE can be greater than or equal to approximately 80°, 90°, 100°, 110°, or 120°.

The piezoelectric actuator 204 can drive the scanning optical fiber 202 near one of the fiber's mechanical resonance frequencies so as to deflect the distal end of the optical fiber in a scanning pattern, thereby scanning the exiting light onto the target surface in a corresponding pattern. The scanning pattern can be any suitable two-dimensional pattern, such as an expanding spiral pattern or a shrinking spiral pattern. In some embodiments, the motion of the resonating optical fiber 202 can be controlled by two amplitude modulating sinusoidal drive signals applied alternatively to the piezoelectric actuator 204, with each drive signal corresponding to an axis of movement of the scanning optical fiber 202. The drive signals can be generated by an external controller coupled to the electrode wires 216 and applied to each quadrant of the piezoelectric actuator 204 via by one of the quartered electrodes 206. Each orthogonal pair of the quartered electrodes 206 can correspond to an axis of the scanning optical fiber 202. The motion incurred in the piezoelectric tube actuator 204 by the drive signals can result in the optical fiber 202 behaving like a base-excited cantilever beam. The resulting motion of the optical fiber 202 can be that of an expanding spiral, moving from the center outward. Optionally, once the optical fiber 202 has reached the outermost ring of the spiral pattern, a braking signal can be applied to the piezoelectric actuator 204 opposite the direction of motion of the fiber 202 so as to rapidly force the fiber 202 back to the center of the spiral pattern, thereby preparing for the next outward spiral scan. The braking signal can be applied at a frequency and phase selected to minimize residual vibrations that may produce image distortion. For example, a braking signal can be applied to vibrate the optical fiber 202 with an excitation frequency approximately equal to the resonant frequency with a root displacement in the opposite direction of the motion of the fiber tip. Alternatively, the optical fiber 202 can be driven without using any braking signals, thereby enabling continuous or approximately continuous imaging. For example, the optical fiber 202 can be driven in alternating outward and inward scan patterns (e.g., outward (expanding) and inward (shrinking) spiral patterns) such that imaging occurs during both the outward and inward trajectories of the fiber 202. In some embodiments, the duty cycle of the assembly 200, which may correspond to the percentage of each period in which the fiber is being actively driven in a scanning pattern, can be within the range between any two of the following: 70%, 75%, 80%, 85%, 90%, 95%, or 99.9%, 99.99%, or 99.999%.

The reflected light 224 returning from the target surface can be collected by the light collection optical fibers 212. Any suitable number of light collection optical fibers 212 can be used, such as 6, 8, 10, 12, or 14 optical fibers. The light collection optical fibers 212 can transmit the reflected light 224 to a light detector (e.g., a charge-coupled device (CCD) or complementary metal oxide semiconductor (CMOS) device). Signals from the light detector can be conveyed to one or more processing modules external to the body for processing and/or storage in order to generate real-time images of the target surface.

Figure 3A:
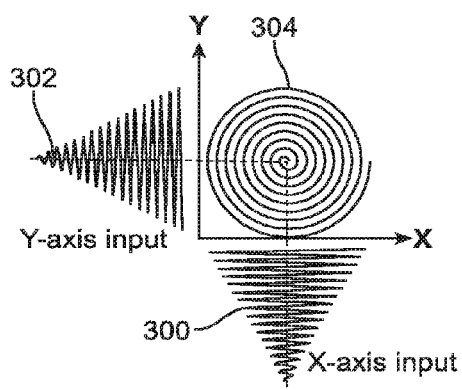
FIGS. 3A through 3D show driving of a scanning optical fiber, in accordance with embodiments.
Figure 3B:
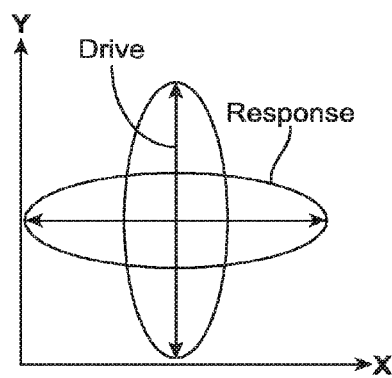
Figure 3C:
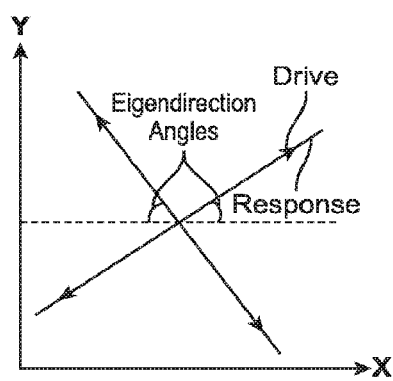

FIGS. 3A through 3D illustrate driving of a scanning optical fiber, in accordance with embodiments. FIG. 3A illustrates drive signals 300, 302 that can be respectively applied to each pair of orthogonal electrodes of a quartered piezoelectric tube actuator to generate an expanding spiral scan pattern 304. For example, one pair can be driven with a ramping sine signal and the other pair can be driven with a ramping cosine signal. The drive signals can be applied to simultaneously scan the optical fiber along first and second axes (e.g., x-axis and y-axis). Each axis can be an axis of movement of the piezoelectric actuator and/or optical fiber along a physical dimension. FIG. 3B illustrates a whirling response of a scanning optical fiber produced by driving along x- and y-axes. In some embodiments, the two axes of the optical fiber may be cross-coupled, in that exciting one pair of electrodes of the piezoelectric tube may produce displacement along both axes of the optical fiber manifested as a whirling response. The whirling response may result in distortion of the optical fiber scan trajectory and the resultant image. FIG. 3C illustrates a straight line response of a scanning optical fiber produced by driving along eigendirections. Eigendirections can refer to driving directions for the optical fiber along which a straight line response is observed (e.g., little or no whirling). The eigendirections can be two uncoupled orthogonal axes ("virtual axes") that typically do not coincide with the axes of the electrode pairs ("real axes"). The eigendirections can depend on random imperfections and/or fiber ovularity, and may vary with each manufactured scanning optical fiber. In order to drive the optical fiber along an eigendirection, both pairs of piezoelectric tube electrodes may be activated, leading to the concept of "virtual electrodes":

$$VE_1(t)=\text{signal}_1(t)[\sin\theta_1 \hat{X}+\cos\theta_1 \hat{Y}] \quad \text{(Eq. 1)}$$

$$VE_2(t)=\text{signal}_2(t)[\sin\theta_2 \hat{X}+\cos\theta_2 \hat{Y}] \quad \text{(Eq. 2)}$$

Figure 3D:
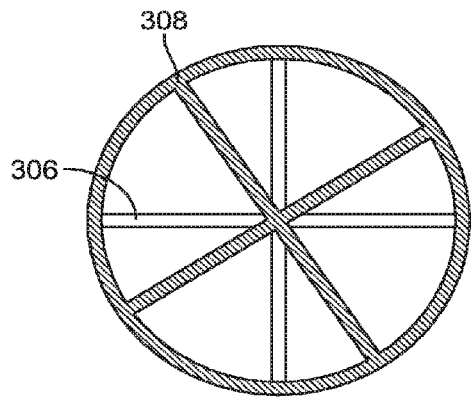

$\hat{X}$ and $\hat{Y}$ are the two real piezoelectric tube electrode pair signals. The virtual electrodes $VE_1$ and $VE_2$ can be combinations of both the latter, and can be governed by rotation angles $\theta_1$ and $\theta_2$ which define the two eigendirections. Since the eigendirections are uncoupled, driving along an eigendirection can produce a response along that eigendirection, e.g., a straight line response. FIG. 3D illustrates real axes 306 and virtual axes 308 of a scanning optical fiber. The virtual axes 308 may be mapped onto the real axes 306 by a rotation. Any description herein relating to driving of a scanning optical fiber can be applied to driving of the optical fiber along one or more virtual axes, one or more real axes, or suitable combinations thereof.

Piezoelectric Self-sensing

To achieve high image quality with a scanning optical fiber, it may be desirable to identify certain fiber scan parameters that are important for accurate fiber driving (e.g., according to the scanning profiles described herein). Exemplary fiber scan parameters that may be identified to improve image quality including: the eigendirections of the fiber, the first mode resonant frequencies of the fiber, the first mode damped natural frequencies of the fiber, and the braking phases for braking the fiber. However, in some embodiments, some or all of these parameters may change over time. For example, activities associated with the introduction of a scanning fiber endoscope into an in vivo environment (e.g., contact with body fluids, saline flushing) may cause changes in the operating temperature of the fiber, and consequently the mechanical properties of the scanner.

Figure 4:
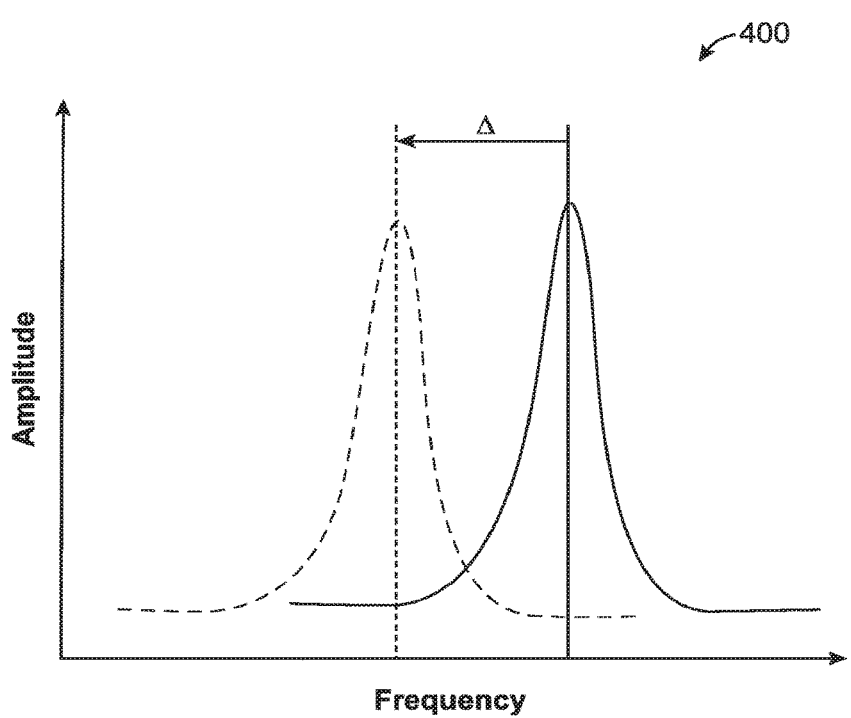
FIG. 4 shows a graph depicting a change in the resonant frequency of a scanning optical fiber.

FIG. 4 shows a graph 400 depicting a change in the resonant frequency of a scanning optical fiber. In some embodiments, the characteristics of a scanning optical fiber can be influenced by the operating conditions to which the optical fiber assembly is exposed. For example, the resonant frequency of the fiber can be shifted by conditions such as temperature changes, material properties, fiber-actuator coupling, or fatigue. The accurate knowledge of the resonant frequency can be critical for determining drive control parameters, as the driving frequency of the scan may typically be set to a slightly lower frequency than the optical fiber's resonant frequency. Knowledge of the resonant frequency can also be important for determining the braking signal to be used. Consequently, unexpected changes in the characteristics of the optical fiber due to variable operating conditions (e.g., variable temperature) can result in image distortion and/or loss of image quality.

Piezoelectric materials such as the piezoelectric actuators described deform when an electric field is applied and generate charge when deformed, thereby enabling them to be used both as sensors and as actuators. Accordingly, the piezoelectric actuators described herein can be used both as actuators for driving a scanning optical fiber and as sensors for detecting the resultant displacement of the piezoelectric actuator and/or optical fiber. The displacement data can be used to determine a position of the optical fiber, such as a position of the distal end of the optical fiber. Any description herein referring to a position or displacement of the optical fiber can be applied to a position or displacement of the distal end of the optical fiber.

The displacement data obtained by the piezoelectric actuator can be used as feedback to dynamically adjust the scanner control during operation so as to improve driving accuracy. Additionally, the displacement data can be used to determine various system parameters relevant to maintaining the driving accuracy of the optical fiber, as well as detect or track any changes in these parameters caused, for instance, by variable operating conditions. This approach, referred to herein as "self-sensing," can be used to provide adaptive control of the optical fiber scanner without requiring the use of additional components (e.g., external optical sensors such as position sensing detectors) to determine the position of the optical fiber tip. Self-sensing can be particularly advantageous for small scale scanning optical fiber systems (e.g., systems having a housing diameter less than or equal to 2 mm, 1.5 mm, 1.2 mm, or 1 mm), since external position sensing devices may be substantially larger than the scanning optical fiber system itself. Furthermore, the self-sensing methods described herein can eliminate the need for manual recalibration or the addition of scanner components for monitoring and/or controlling the operating environment of the scanning assembly (e.g., temperature sensors, heating coil), thereby reducing the size, cost, power consumption, and complexity of such devices while enabling them to be used in diverse operating conditions.

Figure 5:
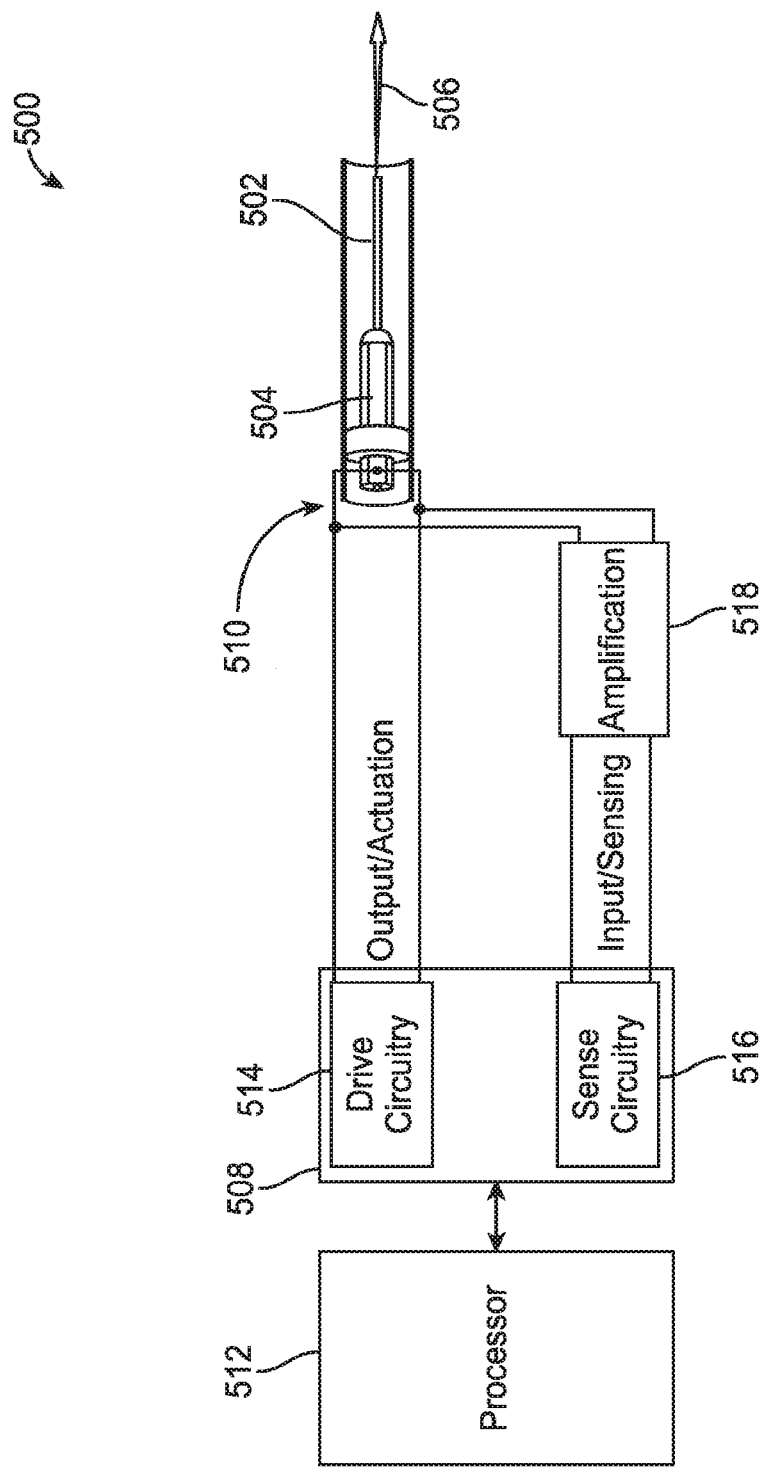
FIG. 5 shows a self-sensing scanning optical fiber system, in accordance with embodiments.

FIG. 5 shows a self-sensing scanning optical fiber system 500, in accordance with embodiments. The system 500 can include a scanning optical fiber 502 driven by a piezoelectric actuator 504 (e.g., a piezoelectric tube) to scan light (e.g., laser spot 506) onto a target surface, as previously described herein. The piezoelectric actuator 504 can be coupled to interface circuitry 508 via electrode wires 510. The interface circuitry 508 can be coupled to a processor 512 (e.g., of a computing system such as a personal computer).

The interface circuitry 508 can include any suitable combination of active or passive circuit elements. The interface circuitry 508 can include drive circuitry 514 configured to generate and output piezoelectric drive signals for actuating the optical fiber 502 via the piezoelectric actuator 504. In some embodiments, the drive circuitry 514 can include two drive circuits, each coupled to an orthogonal electrode pair of the piezoelectric actuator 504 so as to provide drive signals for the actuator 504 along an axis of the optical fiber 502. The piezoelectric drive signals described herein can include one or more of piezoelectric voltage drive signals, piezoelectric charge drive signals, or piezoelectric current drive signals. The drive signals can be generated based on control information provided by the processor 512.

The interface circuitry can also include sense circuitry 516 (also known as "self-sensing circuitry") for detecting piezoelectric displacement signals generated by the displacement and/or deformation of the piezoelectric actuator 504. The sense circuitry 516 can include two sense circuits, each coupled to an orthogonal electrode pair of the piezoelectric actuator 504 so as to obtain displacement signals for the actuator 504 along an axis of the optical fiber 502. "Displacement signal" may be used herein to refer to signals indicative of the displacement and/or displacement rate of a piezoelectric element. The piezoelectric displacement signals described herein can include one or more of piezoelectric voltage displacement signals, piezoelectric charge displacement signals, or piezoelectric current displacement signals.

In some embodiments, the sense circuitry and drive circuitry can share some circuit elements. Alternatively, the sense circuitry and drive circuitry can be separate circuits. Optionally, amplification circuitry 518 can be provided in order to amplify the signal received by the sense circuitry 516 from the piezoelectric actuator 504. The displacement signals received by the sense circuitry 516 can be transmitted to the processor 512 and processed to determine the displacement of the piezoelectric actuator 504 and the corresponding displacement of the optical fiber 502. The displacement data can be used as feedback for controlling of the driving of the optical fiber 502. Furthermore, the displacement data can also be used to determine various parameters of the system 500, which can subsequently be used for adaptive (feedforward) control of the system 500, as discussed below.

In some embodiments, the drive signals and the displacement signals described herein can be transmitted over the same electric channels such that both signals are detected by the sense circuitry 516. For example, the drive circuitry and the sense circuitry can both be coupled to the electrodes of the piezoelectric actuator 504. Consequently, suitable methods can be implemented to enable the sense circuitry 516 to differentiate between the displacement signals and the drive signals, and thereby determine the displacement of the optical fiber 502. In one approach, the actuation and sensing of the piezoelectric actuator 504 may occur at different times (e.g., sequentially), such that the drive signals and displacement signals are detected by the sense circuitry 516 separately. For example, the piezoelectric actuator 504 can be driven by alternating drive signals and brake signals (both generated by the drive circuitry 514) so as to repeatedly scan the optical fiber 502 along a scan pattern, as previously described.

The displacement signals can be measured by the sense circuitry 516 at any time during the driving cycle of the actuator 504 and optical fiber 502. For example, the displacement signal produced by the actuator 504 due to residual vibrations of the actuator 504 and/or fiber 502 can be measured by the sense circuitry 516 can be measured during the time interval following the application of the drive signal and before the application of the brake signal (e.g., the settling phase). Alternatively, the displacement signal can be obtained from residual vibrations following the application of the braking signal and prior to the application of the drive signal. In some embodiments, the displacement signal can be measured during the initial portion of the drive signal used to create the scan pattern from the initial transient response of the optical fiber 502 and/or actuator 504. Furthermore, the drive circuitry 514 can drive the optical fiber 502 with a drive signal having some white noise, thus producing multiple response frequencies in displacement signal of the actuator 504 and/or optical fiber 502.

The obtained displacement signals can be processed by the processor 512 in order to determine various parameters of the system 500. Exemplary parameters that can be determined using this approach include: the two rotation angles $\theta_1$, $\theta_2$ defining the two eigendirections of the system 500; the two damped first natural frequencies (resonant frequencies) $f_1$, $f_2$ of the fiber 502 corresponding to the two eigendirections; the two phases-at-braking $\varphi_1$, $\varphi_2$ of the braking signal for the scanning fiber 502 for the two damped first natural frequencies; the phase-of-braking for second or higher resonant frequencies; or other braking parameters (e.g., number of cycles, amplitude, arbitrary braking patterns, etc.). For example, the eigendirections can be determined by driving the fiber 502 and actuator 504 along the first and/or second axes, and using the obtained displacement signals to determine the directions at which straight-line (or near straight-line) responses are obtained. The damped natural frequencies can be obtained by analyzing the frequency spectrum of the residual oscillations of the fiber 502 and/or actuator 504. Typically, the residual motion after forcing is removed will be a decaying oscillation at the damped first natural frequency. The frequency can be determined using relatively few cycles of decaying fiber motion, such as less than five cycles. The phase-at-braking can be determined by analyzing the frequency spectrum of the residual motion to determine the amount of energy about each frequency component, and searching for the braking phase(s) that removes the most energy from the vibrating system. In some embodiments, the frequency analyses described herein can be performed continuously, such that the actuation of the fiber 502 does not need to be stopped.

In an alternative approach, the sense circuitry 516 can include circuit elements adapted to isolate the displacement signals from the drive signals, such as the bridge circuits described below. Accordingly, the actuation and sensing of the piezoelectric actuator 504 can occur simultaneously (or approximately simultaneously), such that the sense circuitry 516 can measure the displacement signals when the drive circuitry 514 drives the actuator 504 with the drive signals. Advantageously, this approach can be used during continuous scanning of the optical fiber 502 without the use of braking signals, thus enabling higher image frame rates for image acquisition and/or display.

Figure 6:
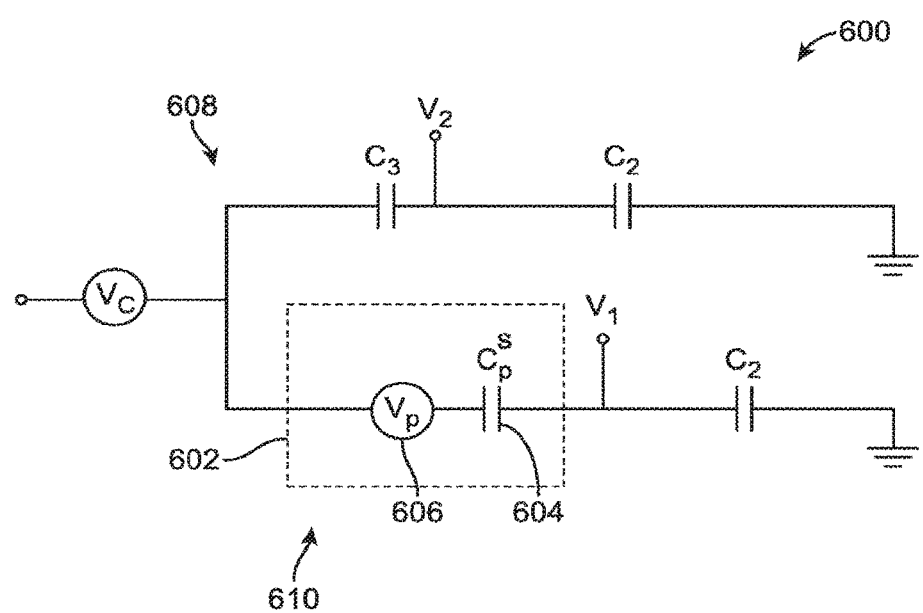
FIG. 6 shows a self-sensing capacitive bridge circuit suitable for incorporation in the systems and devices described herein, in accordance with embodiments.

FIG. 6 shows a self-sensing capacitive bridge circuit 600 suitable for incorporation in the systems and devices described herein, in accordance with embodiments. The bridge circuit 600 can be a monopolar circuit implemented as part of self-sensing circuitry designed to isolate piezoelectric displacement signals from piezoelectric drive signals for a piezoelectric material 602. The piezoelectric material 602 can be modeled in the circuit 600 as a capacitor 604 with an internal voltage source 606. The internal generated voltage can be proportional to the strain on the piezoelectric material 602, which in turn is related to the position of the piezoelectric material 602. The capacitance of the piezoelectric material 602 can be balanced out with the bridge circuit 600 (e.g., using a plurality of capacitors), thus enabling the strain to be measured while the piezoelectric material 602 is being actuated. For instance, the bridge circuit 600 can include first and second parallel legs 608, 610, with the first leg 608 having two capacitors in series, and the second leg 610 having one capacitor in series with the piezoelectric material 602.

Figure 7:
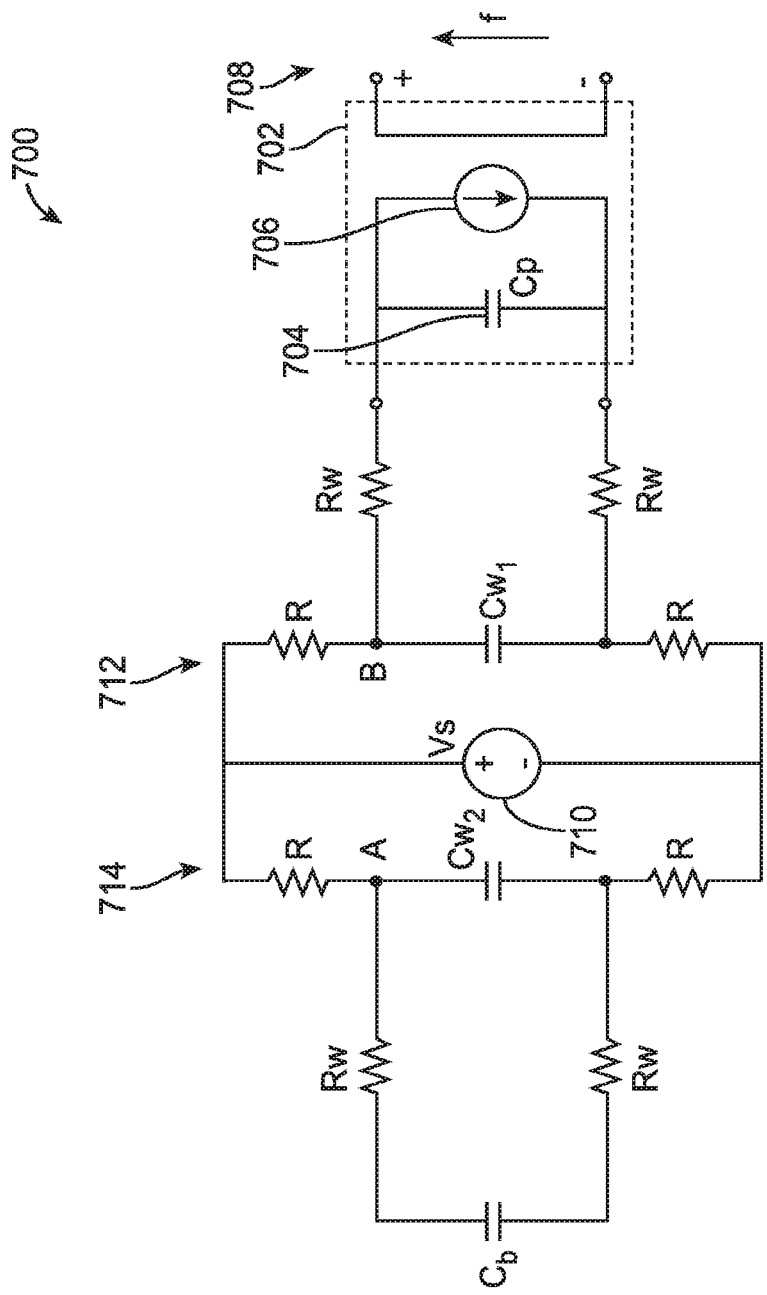
FIG. 7 shows a self-sensing bridge capacitive circuit, in accordance with embodiments.

FIG. 7 illustrates a self-sensing bridge capacitive circuit 700, in accordance with embodiments. The bridge circuit 700 can be used as part of self-sensing circuitry to isolate displacement signals from drive signals for a piezoelectric actuator 702, as described above. The bridge circuit 700 can be coupled to a pair of orthogonal electrodes of the piezoelectric actuator 702, such that the drive and displacement signals measured by the bridge circuit 700 correspond to a first axis of the piezoelectric actuator 702 and optical fiber. The drive and displacement signals for the second axis can be measured by a second bridge circuit similar to the bridge circuit 700. Although the bridge circuit 700 is depicted herein as a bipolar circuit, the circuit 700 can also be configured as a monopolar circuit, depending on the electrical configuration of the underlying scanning optical fiber system.

In the bridge circuit 700, the piezoelectric actuator 702 can be modeled as a capacitor 704 ($C_p$) and current source 706. The force associated with the deformation and/or displacement of the piezoelectric actuator 702 can be modeled as a current 708 ($f$). The voltage source 710 ($V_s$) can produce the differential voltage for the piezoelectric drive signal. The bridge circuit 700 can include a first leg 712 ("actuator leg") and a second leg 714 ("balance leg") in parallel with each other. One or more elements of the first and second legs 712, 714 can be mirrored, so that the first and second legs 712, 714 are at least partially symmetrical. The first leg 712 can include any suitable combination of resistors and capacitors, at least some of which are directly coupled to the piezoelectric actuator 702. For example, the first leg 712 can include one or more capacitors (e.g., $C_{w1}$) coupled between a plurality of resistors (e.g., resistor pairs R, $R_w$). The piezoelectric actuator 702 can be coupled in series between the plurality of resistors. Additionally, the first leg 712 can include at least some resistors and/or capacitors corresponding to the resistance and/or capacitance, respectively, of one or more electrode wires coupled to the piezoelectric actuator 702. For example, the first leg 712 can include two wire resistors ($R_w$) and one wire capacitor ($C_{w1}$) corresponding to the resistance and capacitance of the electrode wires, respectively. The wire resistors can be associated with a wire resistance, and the wire capacitor can be associated with a wire capacitance and wire charge. This approach can be advantageous in embodiments where the electrode wires are relatively long, such as approximately equal to or greater than 2 m in length.

The second leg 714 can include any suitable combination of resistors and/or capacitors. For example, the second leg 714 can include one or more capacitors (e.g., $C_b$, $C_{w2}$) coupled between a plurality of resistors (e.g., resistor pairs R, $R_w$). The second leg 714 can include a balance capacitor ($C_b$) coupled in series between the plurality of resistors. The balance capacitor can be associated with a balance capacitance and balance charge. Similar to the first leg 712, the second leg 714 can include at least some resistors and/or capacitors corresponding to the resistance and/or capacitance, respectively, of one or more electrode wires coupled to the piezoelectric actuator 702, such as two wire resistors ($R_w$) and one wire capacitor ($C_{w2}$). The wire resistors can be associated with a wire resistance, and the wire capacitor can be associated with a wire capacitance and wire charge.

The output of the bridge circuit 700 can be measured by the differential between the voltage at node A ($V_A$) and the voltage at node B ($V_B$). The resultant voltage output ($V_{out}$) can correspond to displacement signal generated in the piezoelectric actuator 702 by its displacement and/or deformation. In some embodiments, the bridge circuit 700 can be modified using techniques known to a person of ordinary skill in the art so that the output of the bridge circuit 700 corresponds to a displacement charge signal or a displacement current signal.

Although reference is made to use of self-sensing bridge circuits for sensing displacement signals during actuation of the piezoelectric actuator, this is not intended to be limiting, as the bridge circuits described herein can be used for any application involving the sensing of piezoelectric displacement signals. For example, a self-sensing bridge circuit can also be used to measure piezoelectric displacement signals in embodiments where the actuation and sensing of the piezoelectric actuator occur at different times.

Adaptive Control

Adaptive control schemes for scanning optical fiber systems can be implemented in order to dynamically detect and compensate for changes in fiber characteristics, such as changes caused by variable environmental conditions as described above. In some embodiments, the control schemes described herein can utilize feedforward and/or feedback control. A feedforward controller may be more economical than other types of controllers, e.g., in terms of hardware timing requirements and computing speed. Additionally, since the system perturbations described herein typically result from temperature fluctuations and human operator movements, and thus may not be very rapid (e.g., approximately tenths of a second), a true feedback controller with compensation on the order of microseconds may be unnecessary.

In some embodiments, a feedforward controller can utilize one or more mathematical models to determine the appropriate input drive signals for an optical fiber scanner. A model can provide a representation of various components of the self-sensing scanning optical fiber systems described herein, such as the self-sensing circuit, piezoelectric actuator, and/or scanning optical fiber. For example, the model can be used to describe the behavior of the scanning optical fiber (e.g., the position of the fiber) in response to a control input (e.g., the drive signal) applied to the piezoelectric actuator. Conversely, given a desired trajectory for the optical fiber, the model can be used to estimate a suitable control input for producing the trajectory. "Trajectory" may be used herein to refer to the positioning of the distal end of the optical fiber. A model can be used to describe the behavior of the system along a single axis or along two axes. In some embodiments, two single-axis models can be combined so as to represent the full behavior of the system along both axes, accounting for electrical cross-coupling of the piezoelectric actuator. Exemplary types of models suitable for use with the approaches described herein include state space electromechanical models and vibration modal models. The characteristic parameters of the model can be determined using any suitable technique, such as system identification and/or parameter estimation based on data obtained via the self-sensing circuitry described herein.

State Space Electromechanical Model

A state space electromechanical model can be used to represent one or more portions of the scanning optical fiber systems described herein. The physical plant of interest for the model can be an electromechanical system including self-sensing circuitry (e.g., bridge circuit 700), a piezoelectric tube, and/or a scanning optical fiber. Using a state space model, the capacitive bridge circuit and the electrical portion of the piezoelectric tube can be modeled by five electrical energy elements with five charge states $Q_{1-5}$. The mechanical scanner can be modeled as a double mass-spring-damper system. The model can be applied to represent behavior of the mechanical scanner along a single axis (e.g., single-axis vibrations). Accordingly, the two masses can be modeled by two velocity states $v_{1-2}$ and two position states $p_{1-2}$. Consequently, a $9^{th}$ order state space model can be obtained:

$$\dot{x} = Ax + Bu$$

$$y = Cx + Du$$

with a 9×1 state vector, $x = [Q_1 Q_2 Q_3 Q_4 Q_5 v_1 v_2 p_1 p_2]^T$. The input u can be the drive voltage applied to the capacitive bridge circuit. The output y can be the piezoelectric self-sensing signal. The specific state of interest can be the optical fiber position $p_2$.

FIGS. 8A through 8D show an exemplary derivation of a state space electromechanical model for a scanning optical fiber system, in accordance with embodiments. Some of the nomenclature used in the derivation is provided in Table 1 below:

TABLE 1

Nomenclature

| Symbol | Definition |
| --- | --- |
| V | voltage |
| i | current |
| R | resistance |
| L | inductance |
| C | capacitance |
| Q | charge |
| v | velocity |
| f | force |
| m | mass |
| k | stiffness |
| c | damping coefficient |
| x | displacement |
| $k_p$ | piezoelectric constant |
| $c_p$ | piezoelectric capacitance |

Figure 8A:
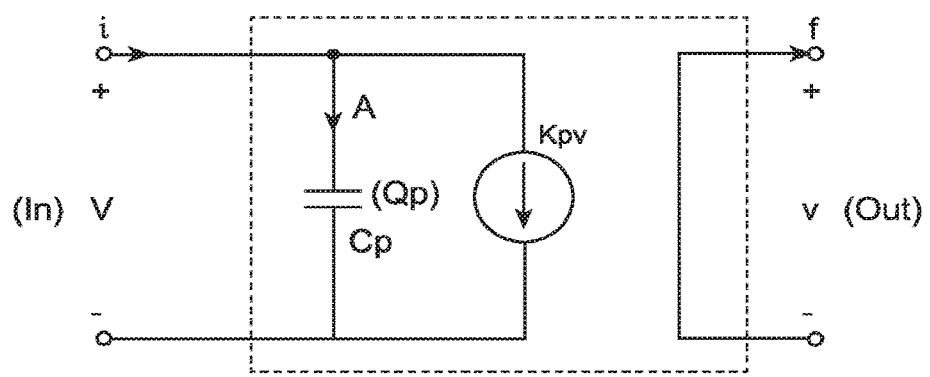
FIGS. 8A through 8D show an exemplary derivation of a state space electromechanical model for a scanning optical fiber system, in accordance with embodiments.

FIG. 8A illustrates a voltage model 800 of a piezoelectric transducer. The model 800 can be used to represent the piezoelectric actuators described herein. In the model 800, the piezoelectric transducer can be represented as a capacitor having capacitance $C_p$ and charge $Q_p$ and a current source characterized by $k_p v$. In alternative embodiments, the piezoelectric transducer can be represented using an equivalent series voltage source rather than a current source. A force f can be applied to the piezoelectric transducer to generate a velocity v. A person of ordinary skill in the art can apply the principle of conservation of energy and Kirchoff's current law at node A of the model 800 to obtain the relationship $$f = k_p \frac{Q_p}{C_p},$$

which describes how the force f is related to the state $Q_p$ (the piezoelectric charge).

Figure 8B:
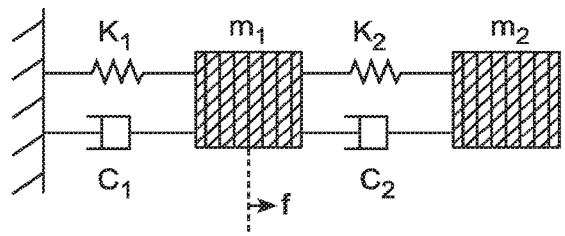

FIG. 8B illustrates circuit equivalents 802 that can be used to represent mechanical elements in the electromechanical model. As would be known to a person of ordinary skill in the art, a resistor element can correspond to a damper element, an inductor element can correspond to a spring element, and a capacitor element can correspond to a mass element. Similarly, the mechanical parameters associated with the mechanical elements can be represented by analogous electrical parameters associated with the corresponding electrical elements, as depicted in FIG. 8B.

Figure 8C:
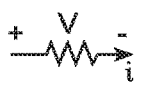

FIG. 8C illustrates a mechanical model 804 of the piezoelectric actuator and scanning optical fiber (collectively referred to herein as the "mechanical scanner"). The mechanical scanner can be modeled as a double mass-spring-damper system. The elements $m_1$, $k_1$, $c_1$ correspond to the parameters of the piezoelectric actuator, while the elements $m_2$, $k_2$, $c_2$ correspond to the parameters of the optical fiber. A force f can be applied to the mass $m_1$ of piezoelectric actuator to produce a displacement of the mechanical scanner.

Figure 8D:
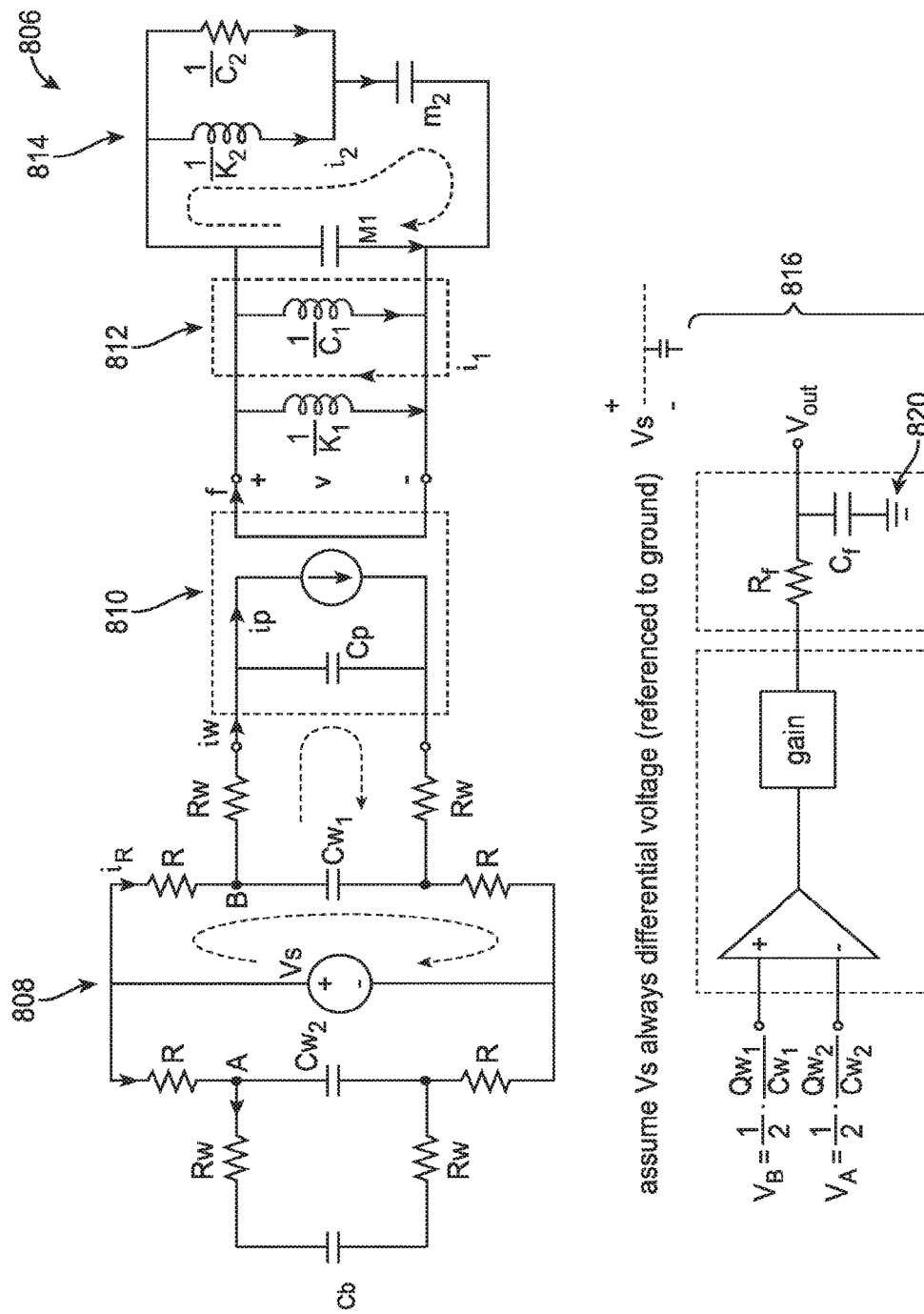

FIG. 8D illustrates the full model 806 of the electromechanical system. Notably, the model 806 can include not only the bridge circuitry 808 and the electrical portions of the piezoelectric actuator 810, but also the mechanical portions of piezoelectric actuator 812 and the scanning optical fiber 814. The model 806 can be an electrical model, such that the mechanical components are represented by the electrical equivalents described above. The bridge circuit 808 can be any embodiment of the self-sensing bridge circuits previously described herein (e.g., circuit 700). The model 806 can also include an instrumentation amplifier 816, which can include a differential amplifier 818 and low-pass filter 820. The non-inverting and inverting inputs of the differential amplifier 818 can be coupled to nodes A and B of the bridge circuit 808, respectively, so that the output voltage ($V_{out}$) corresponds to the differential between the voltage at node A ($V_A$) and the voltage at node B ($V_B$). The output voltage can correspond to an energy output of the mechanical portions of the optical fiber 814 and/or piezoelectric actuator 812 (e.g., energy associated with the deformation and/or displacement of the optical fiber and actuator).

As would be appreciated by one of ordinary skill in the art, Kirchoff's voltage law and Kirchoff's current law can be applied to the model 806 to obtain the following relationships:

$$V_s = 2R\left(\frac{dQ_{w1}}{dt} + \frac{dQ_p}{dt} + k_p\frac{Q_1}{m_1}\right) + \frac{Q_{w1}}{C_{w1}} \quad \text{(Eq. 3)}$$

$$\frac{Q_{w1}}{C_{w1}} = 2R_w\left(\frac{dQ_p}{dt} + k_p\frac{Q_1}{m_1}\right) + \frac{Q_p}{C_p} \quad \text{(Eq. 4)}$$

$$\frac{1}{k_1}\frac{di_1}{dt} = \frac{Q_1}{m_1} \quad \text{(Eq. 5)}$$

$$\frac{Q_1}{m_1} = \frac{1}{k_2}\frac{di_2}{dt} + \frac{Q_2}{m_2} \quad \text{(Eq. 6)}$$

$$\frac{dQ_2}{dt} = i_2 + \left(\frac{1}{k_2}\frac{di_2}{dt}\right)C_2 \quad \text{(Eq. 7)}$$

$$k_p\frac{Q_p}{C_p} = i_1 + \frac{Q_1}{m_1}C_1 + \frac{dQ_1}{dt} + \frac{dQ_2}{dt} \quad \text{(Eq. 8)}$$

$$V_s = 2R\left(\frac{dQ_{w2}}{dt} + \frac{dQ_b}{dt}\right) + \frac{Q_{w2}}{C_{w2}} \quad \text{(Eq. 9)}$$

$$\frac{Q_{w2}}{C_{w2}} = 2R_w\left(\frac{dQ_b}{dt}\right) + \frac{Q_b}{C_b} \quad \text{(Eq. 10)}$$

$$\frac{dQ_f}{dt} = \frac{1}{2}\frac{\text{gain}}{R_f}\frac{Q_{w1}}{C_{w1}} - \frac{1}{2}\frac{\text{gain}}{R_f}\frac{Q_{w2}}{C_{w2}} - \frac{1}{R_f}\frac{Q_f}{C_f} \quad \text{(Eq. 11)}$$

$$V_{out} = \frac{Q_f}{C_f} \quad \text{(Eq. 12)}$$

Equations 3-11 can be used to form a $9^{th}$ order state space model with input $V_s$. The 9 states of the model are ($Q_{w1}$, $Q_{w2}$, $Q_p$, $Q_b$, $i_1$, $i_2$, $Q_1$, $Q_2$, $Q_f$. Equation 12 is an equation for the output $V_{out}$. The characteristic parameters of the state space electromechanical model can correspond to physical properties of the scanning optical fiber system, such as stiffness, mass, and/or damping of the piezoelectric actuator and/or scanning optical fiber. The parameters can also include capacitances and/or resistances of various components of the scanning system, such as those of the bridge circuit, electrode wires, or piezoelectric actuator. In some embodiments, the model parameters can include $C_p$, $m_1$, $k_1$, $c_1$, $m_2$, $k_2$, $c_2$, $C_{w1}$, or $C_{w2}$.

Figure 9:
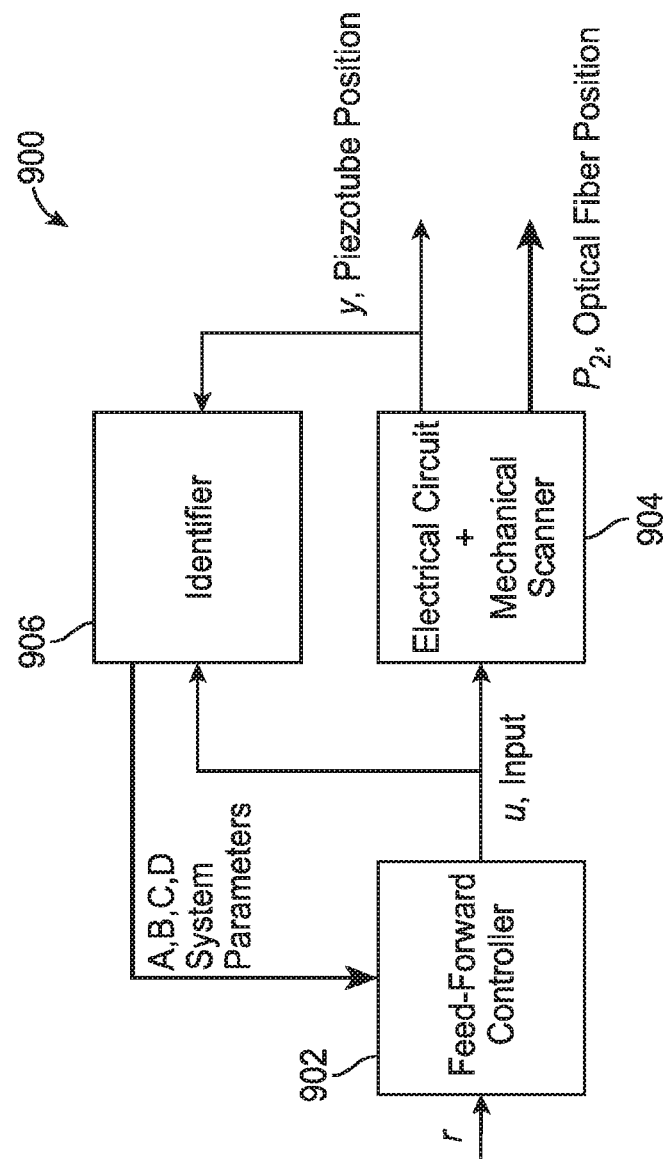
FIG. 9 shows an adaptive (feedforward) control scheme, in accordance with embodiments.

FIG. 9 shows an adaptive feedforward control scheme 900, in accordance with embodiments. The control scheme 900 can be implemented to control any of the systems described herein. In the control scheme 900, a feedforward controller 902 can receive a desired trajectory r for a scanning optical fiber. Based on the trajectory r, the feedforward controller 902 can determine an input u to be applied to the electrical circuit and mechanical scanner ("self-sensing scanner") 804. The input u can be a drive voltage signal applied to a self-sensing capacitive bridge circuit, as previously described herein. The self-sensing scanner 904 can be driven by the input u to displace the piezoelectric actuator ("piezotube") to a piezotube position y and the scanning optical fiber to an optical fiber position $p_2$. The self-sensing circuitry of the self-sensing scanner 904 can sense the piezoelectric displacement signal indicative of the piezotube position y (the "output"). The input u and piezotube position y can be transmitted to an identifier 906. At predetermined intervals, the identifier 906 can use a batch of input u and output y data to estimate a new state space model of the physical plant (the scanning optical fiber system). For example, the state space model can include any of the state space electromechanical models described herein. The estimation of the new model can involve determining one or more system parameters of the model. The new model having the identified parameters can be provided to the feedforward controller 902. The feedforward controller 902 can thus determine the input u used to obtain the desired trajectory r based on the new model.

The identifier 906 can use any suitable method to determine the system parameters of the state space model. In some embodiments, the scanning optical fiber system can be a linear system or a linear-in-parameters system, thus enabling the use of linear system identification techniques.

For example, a batch least squares method can be used to identify the system parameters. The system output can be represented in regressor form $$y(t) = \varphi^T(t)\theta^0$$

where y(t) is the observed output, $\varphi$ is a vector of measurable regressors, and $\theta$ the parameters to be identified (with $\theta^0$ representing the true parameters). By decreasing (e.g., minimizing) the loss function $$V(\theta, t) = \frac{1}{2}\sum_{i=0}^{t}[y(i) - \varphi^T(i)\theta]^2$$

the best parameter estimate $\hat{\theta}$ over the whole batch of data can be given by $$\hat{\theta}=(\varphi^T\varphi)^{-1}\varphi^T Y$$

where Y is a vector of the observed output over the measurement duration and $(\varphi^T\varphi)$ needs to be nonsingular.

To obtain a particular state $p_2$ (e.g., the position of the optical fiber), the identifier can convert between the state space model and the regressor model. To achieve this, the discrete-time state space model can be transformed into the canonical modal form with transformation matrix T. The modal form can then be converted into a discrete time transfer function, which in turn can be used to populate the regressor equation. After the new parameters are identified and substituted back into the transfer function, a new modal matrix can be formed and the inverse transform $T^T$ can be used to recover the new state space model.

The input-output data sets used for the system identification techniques described herein can be obtained at any time, such as prior to the operation of the scanning optical fiber system (e.g., during a test run or calibration run), as well as during the normal operation of the system. Various types of signals can be used for the input drive signals, such as sinusoidal signals, Gaussian white noise, noisy sinusoidal signals (e.g., sinusoidal signal with 10% amplitude Gaussian white noise), or suitable combinations thereof.

Once the system state space model has been identified, it can be used by the feedforward controller 902 to calculate the correct feedforward input to drive the optical fiber state along the desired trajectory, as discussed above. For example, the feedforward controller can use the identified model to calculate the transfer function from control input u to optical fiber state $p_2$. Optionally, the transfer function can be conditioned, so as to improve the tracking of the optical fiber along the desired trajectory. In a non-limiting example, the controller can then calculate the inverse transfer function, and then calculate the feedforward control input u based on the desired trajectory r using the inverse transfer function. Other non-limiting examples to find appropriate feedforward control input include transforming the transfer function into another space (such as state space, frequency space, etc) and then calculating a reduced-order inverse.

Vibration Modal Model

In alternative embodiments, the scanning optical fiber systems described herein can be represented using a vibration modal model. Similar to the state space models previously described herein, the vibration modal model can be used to determine the relationship between a desired trajectory for the scanning optical fiber and the feedforward control input drive signal used to produce this trajectory. Unlike the state space models, the vibration modal model can be determined without providing an electromechanical model of the scanning optical fiber system.

Figure 10:
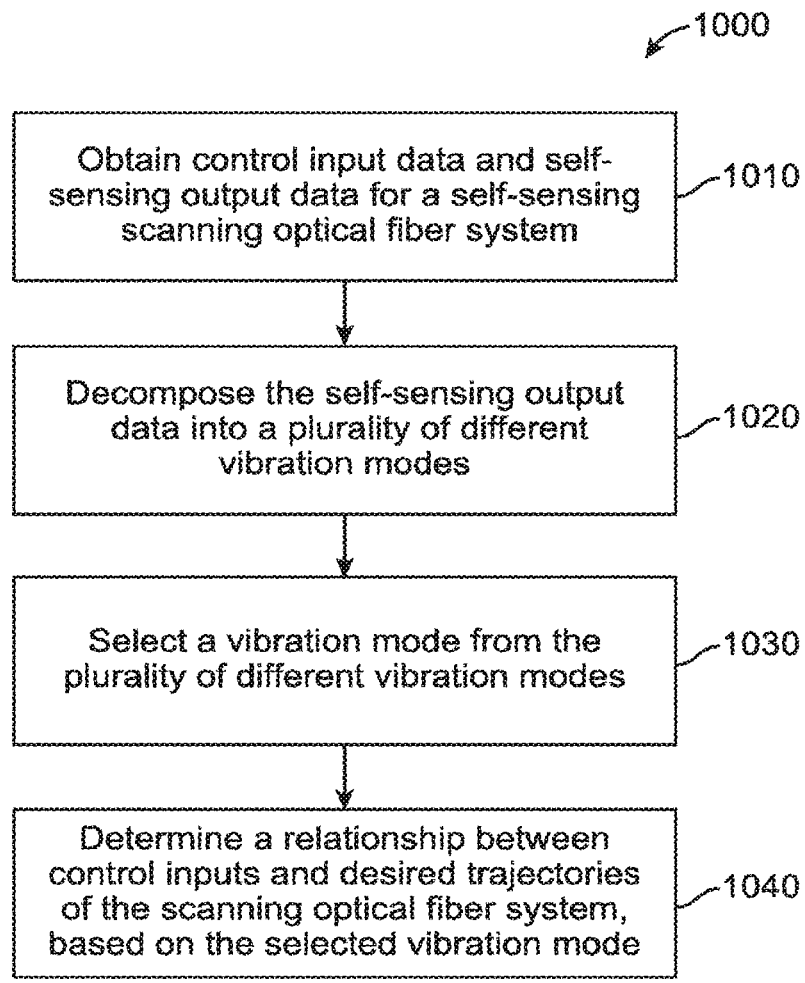
FIG. 10 shows a method for determining a vibration modal model for adaptive (feedforward) control, in accordance with embodiments.

FIG. 10 shows a method 1000 for determining a vibration modal model for adaptive feedforward control, in accordance with embodiments. The method 1000 can be practiced by any suitable component of the systems and devices described herein (e.g., a processor, feedforward controller, and/or identifier).

In step 1010, control input data and self-sensing output data are obtained for a self-sensing scanning optical fiber system. The self-sensing scanning optical fiber system can be any embodiment of the systems described herein. The control inputs to the self-sensing system can be piezoelectric driving signals and the self-sensing output can be piezoelectric displacement signals measured by self-sensing circuitry, as discussed above. The input and output data can be obtained prior to or during normal operation of the optical fiber scanner.

Figure 11:
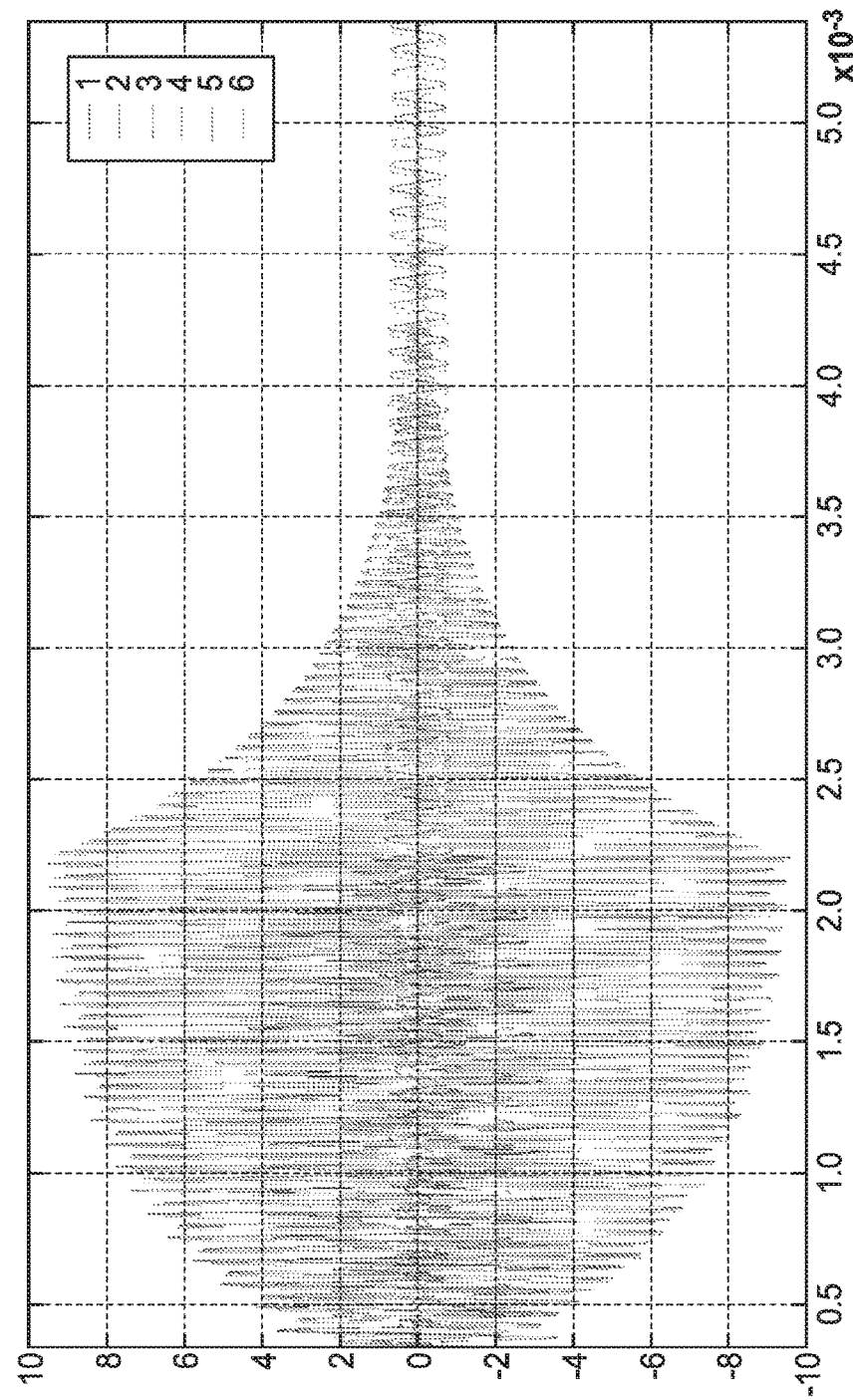
FIG. 11 shows a graph depicting exemplary decomposition of a piezoelectric displacement signal into six different vibration modes, in accordance with embodiments.
Figures 12A, 12B:
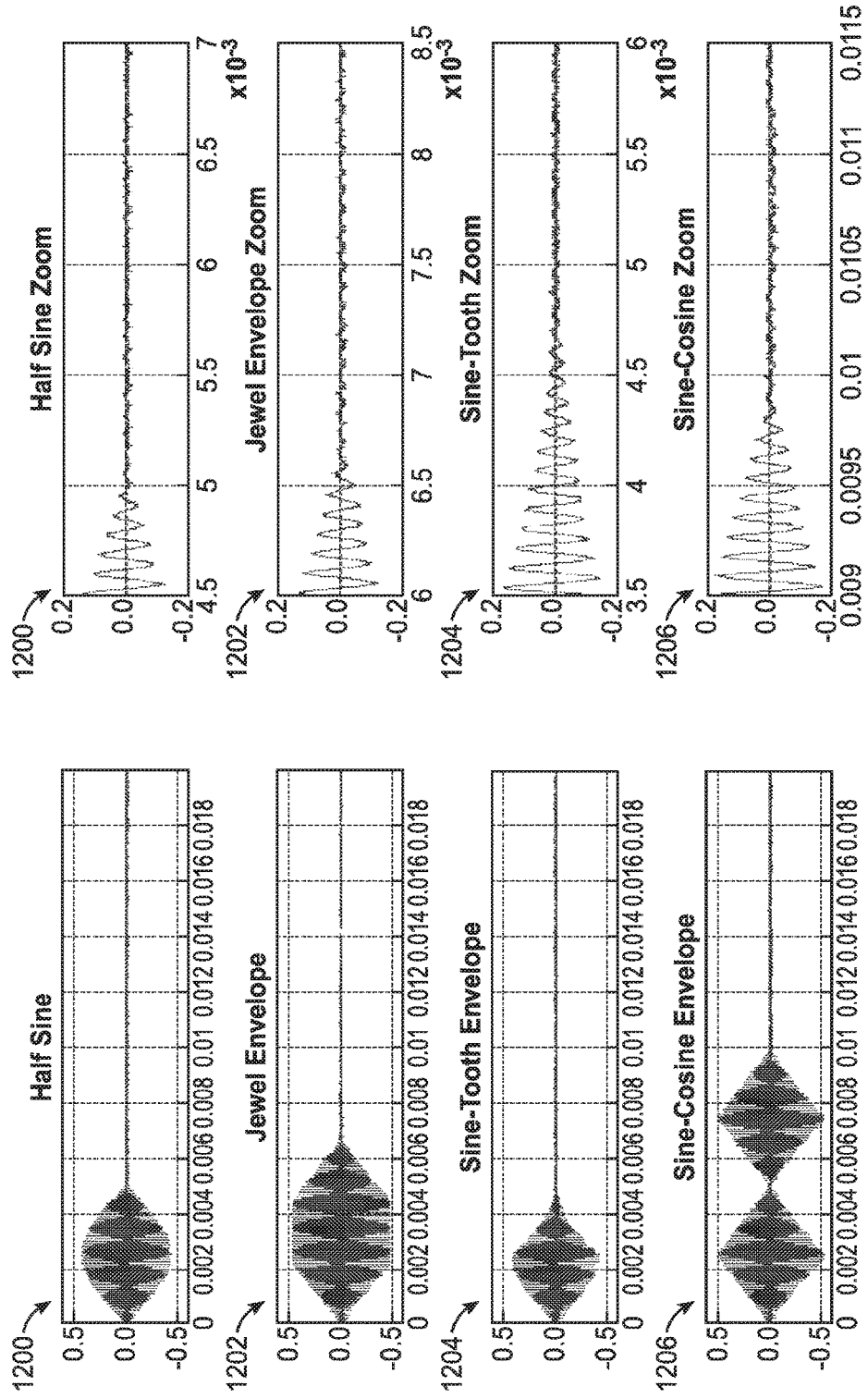
FIGS. 12A through 12D show exemplary trajectories of a scanning optical fiber generated based on a vibration modal model, in accordance with embodiments.
Figures 12C, 12D:
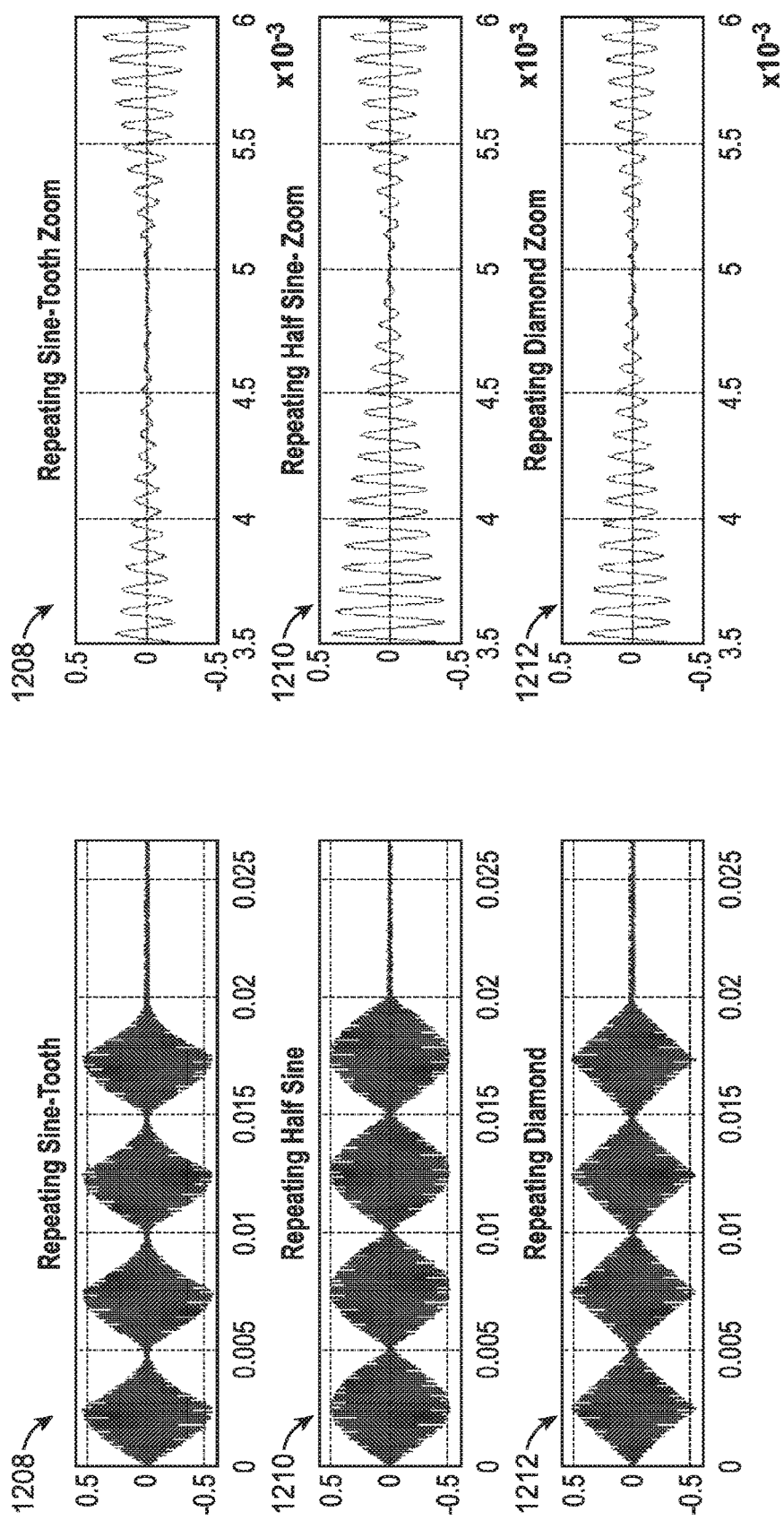

In step 1020, the self-sensing output is decomposed into a plurality of different vibration modes. FIG. 11 shows a graph 1100 depicting exemplary decomposition of a piezoelectric displacement signal into six different states or traces (but 2 harmonic vibration modes present; i.e., 2 traces for each vibration mode), in accordance with embodiments. Any suitable technique can be used to perform the decomposition. For example, a least squares fit to an autoregressive-moving-average regression with exogenous inputs (ARMAX) model can be performed. A matrix transform can then be used to obtain a modal matrix containing the plurality of different vibration modes for the displacement signal.

In step 1030, a vibration mode is selected from the plurality of different vibration modes. Any suitable approach can be used to select the vibration mode. For example, the mode can be selected based on the shape of the mode and the desired function. In some embodiments, a first mode may be characterized by a relatively large optical fiber deflection, and a second mode may be characterized by a relatively small fiber deflection. The first mode may be selected since the laser spot emanates from the tip of the optical fiber, as well as based on other optics considerations.

In step 1040, a relationship between the control inputs and desired trajectories of the scanning optical fiber system is determined, based on the selected vibration mode. For example, the steps 1020 and 1030 can be used to obtain an input-to-mode transfer function. The input-to-mode transfer function can be inverted in order to obtain the mode-to-input transfer function. Based on the mode-to-input transfer function, the desired trajectory-to-control input transfer function can be determined.

The vibration modal model can be applied in an adaptive control scheme similar to the control scheme 900 previously described herein. For instance, an identifier (e.g., identifier 906) can be used to determine a vibration modal model for a self-sensing scanner (e.g., electrical circuit and mechanical scanner 904) based on control inputs and self-sensing outputs (e.g., the piezotube position), such as using the method 1000. The vibration modal model can include a desired trajectory-to-control input transfer function. An adaptive controller (e.g., feedforward controller 902) can use the determined transfer function to generate inputs for directing the self-sensing scanner along a desired trajectory. The identifier can periodically generate a new vibration modal model from batch input and output data, thereby enabling the feedforward control scheme to be adaptively updated to compensate for changing fiber characteristics and/or environmental conditions.

FIGS. 12A through 12D show exemplary trajectories of a scanning optical fiber generated based on a vibration modal model, in accordance with embodiments. The trajectories include a half sine envelope 1200, jewel envelope 1202, sine-tooth envelope 1204, sine-cosine envelope 1206, repeating sine-tooth envelope 1208, repeating half sine envelope 1210, and repeating diamond envelope 1212. The trajectories exhibit good tracking of the optical fiber position with the targeted trajectory envelope, as well as low residual vibrations (see, e.g., zoom views in FIGS. 12B and 12D).

Alternative Modal Modeling

In some embodiments, an alternative modeling approach based on modal analysis is used. In some embodiments, instead of representing the piezoelectric-tube and optical fiber cantilever structure as two point masses, various other modeling approaches are used.

For instance, one alternative approach is to analytically calculate the dynamic response based on continuum mechanics. The Euler-Bernoulli dynamics beam equation can be used for analysis of the optical fiber cantilever:

$$\rho A \frac{\partial^2 v}{\partial t^2} + \frac{\partial^2}{\partial x^2}\left(EI \frac{\partial^2 v}{\partial t^2}\right) = 0$$

where $\rho A$ is the mass-per-unit length, E the elastic modulus, I the area moment of inertia, v the transverse displacement, x the distance along the axis of the optical fiber, and t time. In some embodiments where the piezoelectric-tube portion of the scanner is not considered, EI is set be a constant along the length of the cantilever.

The solution of the Euler-Bernoulli equations gives an infinite number of natural frequencies:

$$\omega_n = \frac{c_q (\beta_n l)^2}{l^2},$$

$$c_q = \sqrt{\frac{EI}{\rho A}}, \text{COSH}(\beta_n l)\text{COS}(\beta_n l) = -1, n = 1, 2, 3, \ldots$$

and corresponding mode shapes of the optical fiber cantilever given by:

$$\varphi_n(x) = c \text{ COS}(\beta_n x) + d \text{ SIN}(\beta_n x) + e \text{ COS } H(\beta_n x) + f \text{ SIN } H(\beta_n x)$$

where c, d, e, f depend on the boundary conditions. In some embodiments, these linear mode shapes are then used as the assumed mode shape.

In an alternative embodiment, the mechanical structure is discretized (e.g. using finite element methods), and then numerical analysis of its dynamics is performed. For example, a finite-differencing method can be performed based on the following governing equations of a nonlinear cantilever beam:

$$\rho A \ddot{u} + c_x \dot{u} + EI_x u'''' = -EI_x[u'(u'u'' + v'v'')']'$$

$$\rho A \ddot{v} + c_y \dot{v} + EI_y v'''' = -EI_y[v'(u'u'' + v'v'')']'$$

where the dots represent temporal derivatives, the primes represent spatial derivatives, and u and v are the two orthogonal transverse displacements. Finite differencing puts the above governing equations into the following form:

$$M\ddot{x} + C\dot{x} + Kx = -f(x,\dot{x},t)$$

where M is the mass matrix, C the damping matrix, K the stiffness matrix, x the displacement vector and f a nonlinear function. The linear form of the above equation is:

$$M\ddot{x} + C\dot{x} + Kx = F$$

where F is the forcing function. To form the damping matrix C, a simplified Raleigh damping model can be used, where the damping matrix is proportional to the stiffness matrix, $C = \gamma K$. In embodiments where M is positive definite and K is positive semi-definite, the solution can be described in terms of the natural frequencies $\omega_n$ and mode shapes $\varphi_n$ found by solving the eigenvalue problem:

$$[\omega_n^2 M + j\omega_n C + K]\varphi_n = 0, n = 1, 2, 3, \ldots$$

Further, if C is proportional to K (i.e. Raleigh damping, which is a subset of the modal damping model), then the matrices M, C, K can all be diagonalized by the mode shape matrix $\varphi$ (which is identical to the mode shape matrix in the undamped case):

$$\varphi^T[M\ddot{x} + C\dot{x} + Kx]\varphi = \varphi^T[F]\varphi$$

This will transform the equation $M\ddot{x} + C\dot{x} + Kx = F$ into $\tilde{M}\ddot{p} + \tilde{C}\dot{p} + \tilde{K}p = \tilde{F}$. Since $\tilde{M}, \tilde{C}, \tilde{K}$ are diagonal, a solution is n-uncoupled differential equations describing the displacement $p_n$ of the n-vibration modes. The transformed forcing input $\tilde{F}$ is the equivalent contribution of the forcing input F to each orthogonal vibration mode.

Figure 14A:
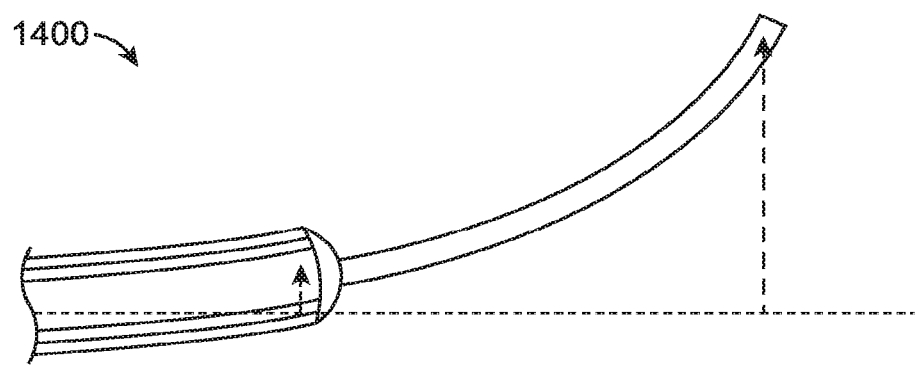
FIGS. 14A and 14B illustrate extended mode shapes for displacement of an optical fiber and piezoelectric actuator, in accordance with embodiments.
Figure 14B:
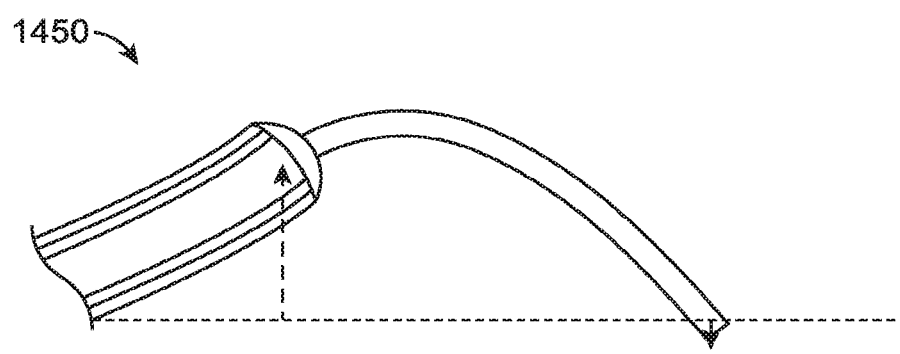

In some embodiments, the modal damping assumption leads to mode shapes where each point along the structure moves in tandem and crosses the zero-axis at the same time. FIGS. 14A and 14B, described in further detail below, show the first two modes expected of the piezoelectric tube and fiber optic structure, in accordance with embodiments. Some significant results can be determined from knowing the mode shapes and assuming their orthogonal dynamics. Firstly, since the piezoelectric tube and the fiber optic move in tandem, by sensing the displacement of the piezoelectric tube, the position and phase of the fiber-optic tip can be inferred. The laser beam (or other light source) for imaging/display can be steered from the optical fiber tip. Secondly, in some embodiments, methods in experimental modal analysis can be applied, where the transfer function from excitation to response at different structural points are used to identify the parameters of the uncoupled differential equations described herein. System identification can be used to accurately determine and/or control the dynamics of the first (or possibly other) vibration mode, which is being controlled.

Although the above analysis was primarily concerned with the dynamics of the mechanical scanner, the dynamics of the sensing circuit can also be considered in some embodiments. Optionally, since the sensing circuit is comprised of capacitors and resistors, it can be assumed to not have any resonant dynamics. As such, the sensing circuit can have a passive filtering effect on the actuation and sensing signals. Suitable methods can be used to identify such filtering effects.

System Identification

The present disclosure contemplates various approaches to system identification for determining parameters of the models described herein. Examples of such approaches include but are not limited to grey-box identification and Batch Least Squares (BLS) identification (e.g., BLS on an ARMAX model, brute-force BLS). In some embodiments, BLS identification reduces operation complexity and computing time compared to other methods.

In some embodiments, a high-order BLS with model order reduction is used. To accurately match the experimental input-output data, a high order simple autoregressive exogenous (ARX) model can be used and BLS can be used on the data. Even in the presence of correlated noise, a good match to the experimental data can be obtained (i.e. a model that accurately predicts the output), as illustrated in FIG. 20B (described in further detail below). For instance, consider an input-output model where e(t) is Gaussian White Noise (GWN) but the effective disturbance is colored by an unknown filter with dynamics $$\frac{1}{D(q)}:$$

$$A(q)y(t) = B(q)u(t) + \frac{1}{D(q)}e(t).$$

In the model, q is the left-time-shift operator, y(t) is the output signal, u(t) is the input signal, and A, B represent operators on the respective signals. Rearranging results in:

$$[A(q)D(q)]y(t)=[B(q)D(q)]u(t)+e(t)$$

$$\tilde{A}(q)y(t)=\tilde{B}(q)u(t)+e(t).$$

Now the equation is in the ARX form with GWN disturbance, but the order of $\tilde{A}$ and $\tilde{B}$ has increased.

FIGS. 20A through 20C show the input and output used for system identification and the simulated trajectories of the identified system model, in accordance with embodiments. FIG. 20A shows the input data. FIG. 20B shows the measured output data versus the predicted output of the identified high-order model. FIG. 20C shows the 50 simulated states of the high-order identified model, in which the state trajectories all look similar. The mechanical scanner responds to the resonant excitation with ramping-amplitude oscillations, which then take time to decay. Matching a model to this data captures the 'finning' effect due to bridge circuit imbalance, and the mechanical properties of the resonant scanner.

After obtaining a model with an excellent match to the experimental data, the next step is to extract useful features from the sprawling model. BLS-ARX identification gives coefficients of the numerator $\tilde{B}(q)$ and denominator $\tilde{A}(q)$ of the model transfer function. In some embodiments, if this transfer function is put into the canonical state space form, all the 50 states are coupled and it is not clear to reduce the system model, as shown in FIG. 20C.

Figure 21:
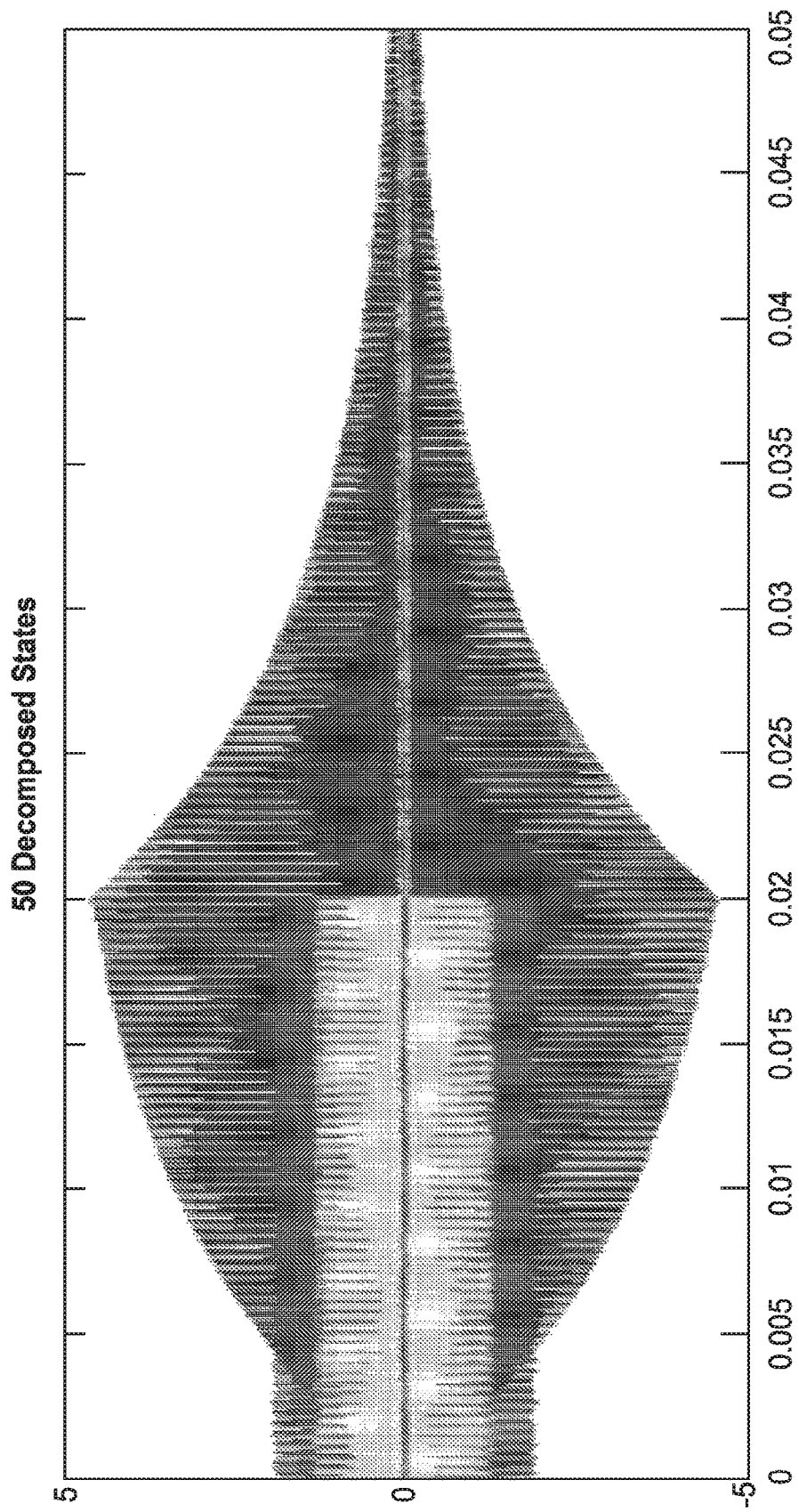
FIG. 21 illustrates exemplary transformed identified model states, in accordance with embodiments.

If instead the modal canonical state-space realization is used, the results are blocks of decoupled states, as shown in FIG. 21. FIG. 21 illustrates transformed identified model states, in accordance with embodiments. The pair of dark-colored states in FIG. 21 is highly suggestive of a resonant mechanical system that continues to vibrate after being excited close to its resonant frequency. Inspection of the eigenvalues of the block-diagonal entry of the A-matrix corresponding to the above-mentioned pair of states finds that the equivalent natural frequency is 13.322 kHz. The nominal first mode natural frequency for the actual mechanical scanner was 13.3 kHz. The equivalent natural frequencies of the eigenvalues of other block-diagonal A-matrix entries are much further distanced, the closest being at 22.671 kHz, which is actually close to the nominal second mode natural frequency of the mechanical scanner at 22.520 kHz. The above matching natural frequency estimates suggest that actual system information can be extracted from the high-order model.

Figure 22A:
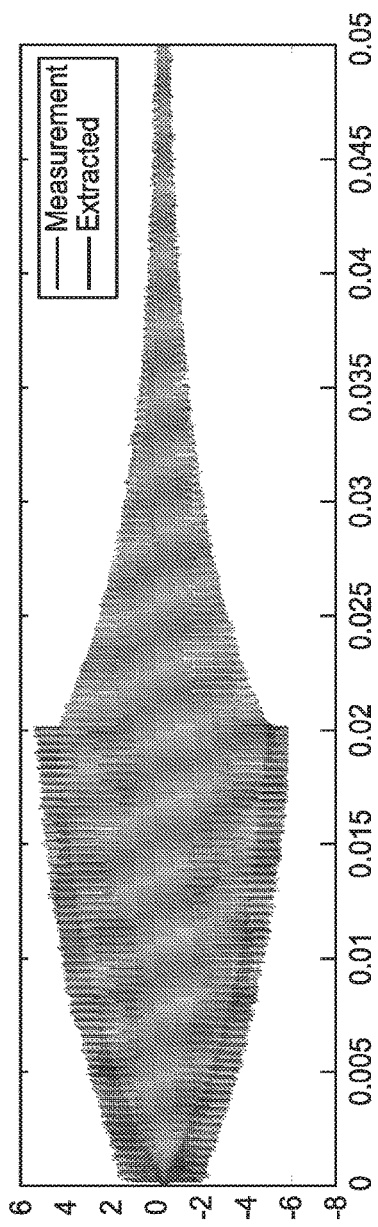
FIGS. 22A and 22B illustrate an exemplary extracted resonant subsystem contribution to the overall measured output signal and the residue after the extracted resonant subsystem is removed, in accordance with embodiments.
Figure 22B:
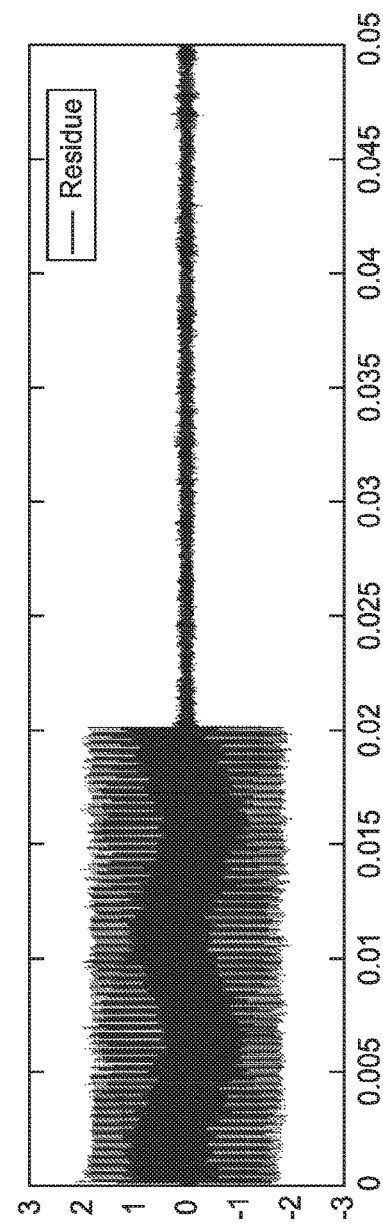

In some embodiments, the resonant subsystem corresponding to the first mode mechanical vibrations is isolated using the natural frequency analysis described above. The contribution of the 2-state subsystem to the output signal is shown in FIGS. 22A and 22B. FIG. 22A illustrates the extracted resonant subsystem contribution to the overall measured output signal and FIG. 22B illustrates the residue after the extracted resonant subsystem is removed, in accordance with embodiments. Subtracting out the contribution of the extracted resonant subsystem, the residue signal can be interpreted as the contribution of noise and feedthrough of the drive signal due to bridge-circuit imbalance.

Figure 23:
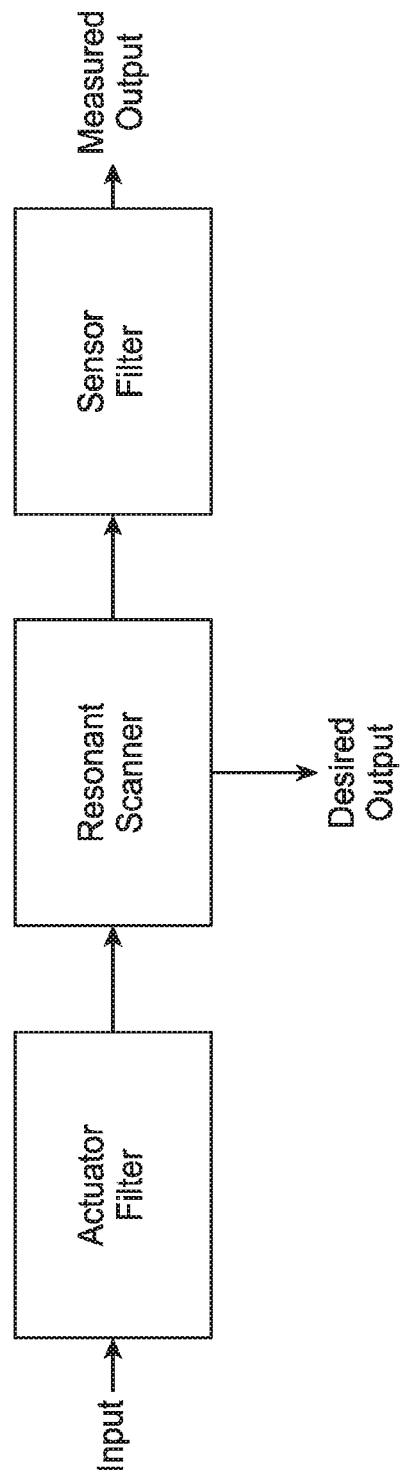
FIG. 23 illustrates an exemplary system identification flowchart, in accordance with embodiments.

It should be noted that though some embodiments have identified a transfer function for the resonant mode being under control, this is an end-to-end (input-to-measured-output) transfer function, which includes the actuator and sensor filtering effects. FIG. 23 illustrates a general end-to-end model that provides a more complete depiction, in accordance with embodiments. In the embodiment of FIG. 23, the effects of actuator and sensor dynamics are put in the general form of filters. The desired output can be related to the internal state of the resonant scanner. In some embodiments where an explicit 9th order electromechanical model is available, the deflections of the optical fiber can be directly isolated within the identified model. In other embodiments, the true optical fiber displacement can be isolated from the end-to-end transfer function. Assuming a true mechanical resonant system, the equation governing oscillations has no zeros:

$$\ddot{x}+2\zeta\omega_n\dot{x}+\omega_n^2 x=F$$

In contrast, the identified resonant subsystem herein may have zeros, which alter the phase of the output signal. This phase alteration can be interpreted as being the contribution of the actuation and sensor filters. By using different probing signals, the effects of the actuator and sensor filters can be isolated. However, in other embodiments, the actuator and sensor filtering effects can be ignored while still achieving good tracking.

Controller Optimization

Various techniques can be used to optimize the control inputs (e.g., piezoelectric drive signals) for driving the scanning optical fiber systems described herein. Some or all of the techniques described herein can be implemented by a suitable processor and/or controller of a scanning optical fiber system. In some embodiments, these approaches can be used in conjunction with the adaptive control methods discussed above so as to provide enhanced control over the scanning optical fiber and improve the quality of imaging results.

For example, parameter space tuning can be used to optimize the control inputs used to drive the piezoelectric actuator to produce a desired trajectory for the scanning optical fiber. The control inputs can be produced by a parameterized controller using one or more of the adaptive feedforward approaches previously described herein. The feedforward transfer function of a parameterized controller can be relatively simple. The controller can be further tuned by searching the parameter space of the controller, using methods known to a person of ordinary skill in the art. The cost to be minimized by the parameter space search can be residual vibration of the piezoelectric actuator and/or optical fiber.

As another example, input shaping can be used to optimize the control inputs so as to produce a fiber scan trajectory having a good fill of the field of view while having reduced frequency content at unwanted vibration mode. Input shaping can be accomplished, for instance, by controlling the envelope design of the drive signal (e.g., sine envelope, sine-tooth envelope, diamond envelope, jewel envelope, etc.). The envelope design can be selected to ensure that the scan pattern covers the desired portion of the field of view, while maintaining the dwell times used to produce satisfactory image quality. Furthermore, the input shape can influence the frequency content of the drive signal. For instance, the envelope design can be selected so as to inhibit or reduce frequency content associated with unwanted vibration modes (e.g., modes other than the selected mode for a vibration modal model). The envelope design-based techniques described herein can advantageously provide control over the control input shape without distorting the resultant fiber trajectory or extending the time during of the drive signal.

In a further example, feedback loops can be used to improve or optimize the control inputs for the piezoelectric actuator. The drive signals can be adjusted, for instance, based on real-time feedback theory. For example, the drive signal can be applied to the actuator to direct the distal end of the optical fiber to a sequence of pixel locations, and self-sensing circuitry can be used to measure the displacement of the actuator and/or optical fiber at each of the pixel locations. The displacement can be used as feedback so as to determine the error at each of the pixel locations and adjust the drive signal in real time so as to correct the error. As previously described, such self-sensing circuitry can advantageously provide positional information without requiring the use of additional position sensing components such as position sensing detectors, thus reducing the size and cost of the optical fiber scanner.

The feedback control can be applied in any suitable manner. For instance, the feedback can be applied for each image frame of a plurality of sequential image frames generated by the optical fiber scanner, referred to herein as "frame sequential feedback." An image frame can correspond to a driving cycle of the scanner. Alternatively, the feedback can be applied for each pixel or batches of pixels of a sequential image frame, referred to herein as "pixel sequential feedback." In some embodiments, the optical fiber scanning systems described herein may be characterized by relatively high system repeatability between each drive cycle or "sweep" of the actuator. Accordingly, the drive signal can be adjusted based on feedback control signals (e.g., displacement data) obtained in real-time, but at a slower time scale than the feedback control signal. Such approaches can also be referred to herein as "iterative learning control" (ILC).

Iterative Learning Control (ILC)

In some embodiments, the controllers described herein utilize learning-type control in order to continuously adapt. In its most general form, learning-type control is a control strategy where the controller makes use of previous information to adjust its control signal. Learning-type control can comprise ILC, repetitive control (RC), and run-to-run (R2R). Compared to adaptive control, learning-type control is more focused on systems where the reference and/or disturbances are repeating in nature. ILC is concerned with the tracking of a repeating trajectory within a finite period, under the assumption that the initial conditions of the system are reset at each period. RC involves tracking or rejecting periodic signals in continuous operation. R2R is defined for processes where only sparse feedback data is available and the system attempts to achieve an output by varying a set of parameters.

ILC is concerned with systems of the form $$y_k(t)=P(q)u_k(t)+d(t)$$

where $u_k(t)$ is the input, $y_k$ the output, $P(q)$ a proper rational function defining the plant, $d(t)$ is the repeating disturbance, and is the iteration number. In ILC, the repeating disturbance $d(t)$ is rejected using a learning algorithm that updates the input. Defining the tracking error:

$$e_k(t)=r(t)-y_k \qquad (t)$$

where $r(t)$ is the desired reference trajectory, a general form of the ILC algorithm is:

$$u_{k+1}(t)=Q(q)[u_k(t)+L(q)e_k(t)]$$

$Q(q)$ is usually called the Q-filter and $L(q)$ is usually called the learning function. Note that the time shift of $e_k(t)$ is absorbed into the $L(q)$ term in order to generalize the equation.

One characteristic of the ILC is that the error will converge (in a noiseless system) to zero under very generous conditions:

$$e_k(t) \to 0, k \to \infty$$

if $\|Q(z)[1-L(z)P(z)]\|<1$, and $Q(z)=1$

These are sufficient but not necessary conditions. In addition, this convergence may not be monotonic, i.e. the convergence may involve large transients. If input or measurement noise is present, the error will converge to a ball around zero-error, with the size of the ball being a continuous function of the noise magnitude.

In some embodiments, $Q(z)$ is 1 in order to converge to perfect tracking. Accordingly, a suitable learning function $L(q)$ can be selected. Setting $Q(z)=1$ is common, but other functions can be selected to trade off tracking performance with robustness. Good robustness can still be achieved with $Q(z)=1$.

The learning function $L(q)$ can be a simple proportional gain, PID or related, a robust or optimal formulation, or an inverse of the expected system dynamics. In some embodiments, all the above approaches when correctly designed will converge very well (though at varying rates). In some embodiments, simple PD schemes are the safest, but a good guess of the system inverse can make the ILC converge very quickly to the desired trajectory.

In some embodiments, an ILC implementation uses:

$$Q(\omega)=1$$

$$L(\omega)=\rho(\omega)P^+(\omega)$$

where the functions are described in the frequency domain (transformed via discrete Fourier transform), $P^+(\omega)$ is a pseudo-inverse of the estimated system transfer function $\hat{P}(\omega)$, and $\rho(\omega)$ is a gain function that ensures convergence to the desired tracking.

In some embodiments, the pseudo-inverse is used:

$$P^+(\omega)=[\alpha+P(\omega)^*P(\omega)]^{-1}P(\omega)^*$$

Figure 24:
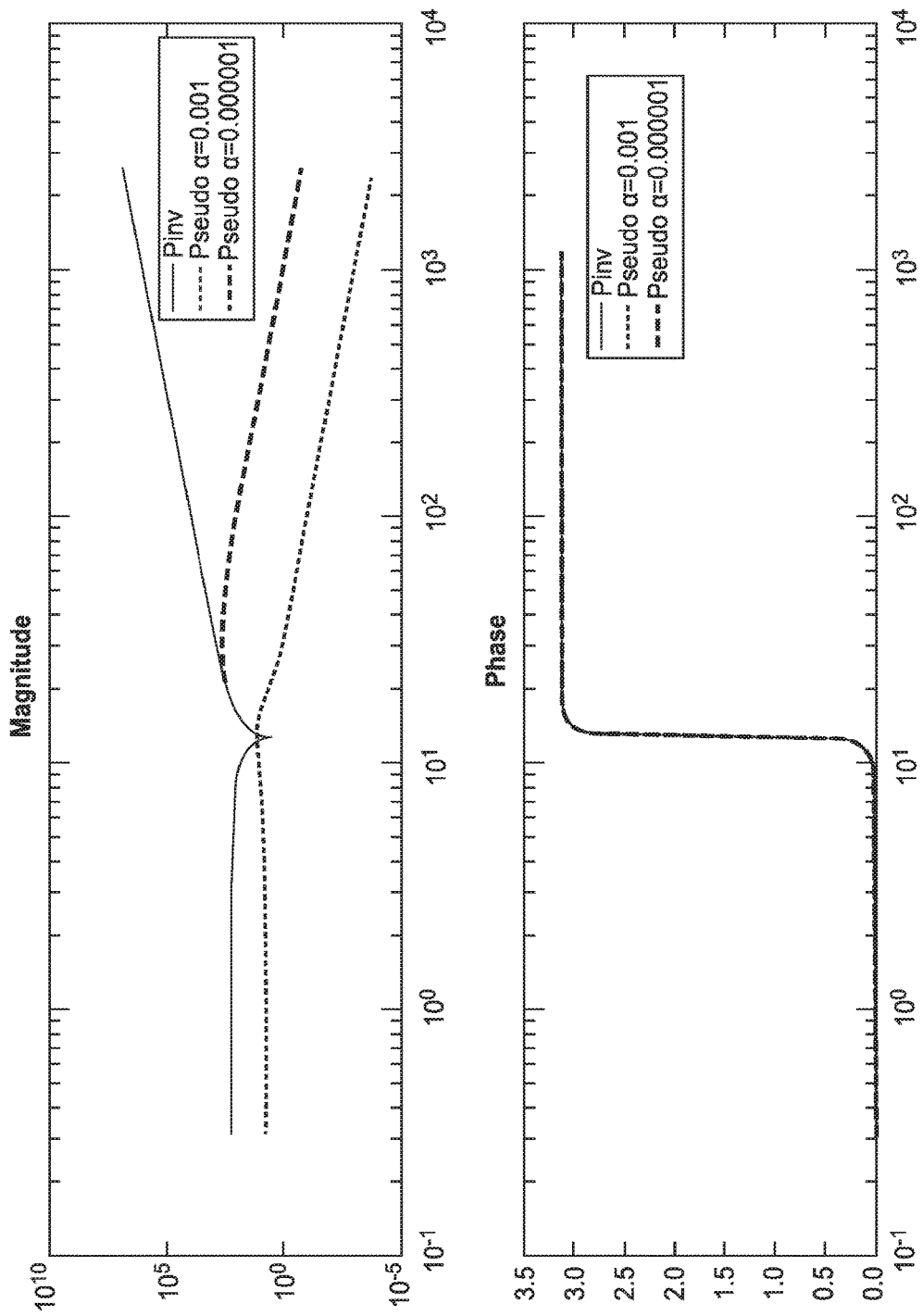
FIG. 24 illustrates an exemplary magnitude and phase of the transfer function using exact inverse, in accordance with embodiments.

$\alpha$ is a parameter that can be tuned. FIG. 24 illustrates the magnitude and phase of the pseudo-inverse transfer function, in accordance with embodiments. In FIG. 24, the magnitude and phase using exact inverse, pseudo-inverse with $\alpha=0.001$, and pseudo-inverse with $\alpha=0.000001$ is shown. Note that there is no phase difference compared to the exact inverse $P^{-1}(\omega)$. Also note that as $\alpha$ decreases, the pseudo-inverse converges to the exact inverse, but there is still a magnitude roll-off at higher frequencies.

The conditions for convergence can be restated as:

$$\|(Q(\omega)[1-L(\omega)P(\omega)]\|<1.$$

Substituting in $L(\omega)=\rho(\omega)P^+(\omega)$ results in:

$$\|1-\rho(\omega)P^+(\omega)P(\omega)\|<1.$$

Ignoring $\rho(\omega)$ for now (let $\rho(\omega)=1$), if $P^+(\omega)=P^{-1}(\omega)$ at certain $\omega$'s then this equation is "very well" satisfied at those frequencies, i.e., convergence to zero tracking error is fast at those $\omega$'s.

When $P^+(\omega)$ rolls off at high frequencies, $\rho(\omega)P^+(\omega)P(\omega) \to 0$, and the equation approaches being not-satisfied. This can be interpreted as learning much more slowly at higher frequencies, where random disturbances that are not wanted to "learn" are rejected.

This pseudo-inverse can also be interpreted as the result of minimizing a frequency-dependent cost function:

$$J(u) = \int_{-\infty}^{\infty} \{u^*(j\omega)R(j\omega)u(j\omega) + [y(j\omega) - r(j\omega)]^*Q(j\omega)[y(j\omega) - r(j\omega)]\}d\omega$$

where the minimizing solution has the familiar form:

$$u_{opt}(j\omega) = [R(j\omega) + P^*(j\omega)Q(j\omega)P(j\omega)]^{-1}P^*(j\omega)Q(j\omega)r(j\omega)$$

comparable to the equation $$P^+(\omega) = [\alpha + P(\omega)^*P(\omega)]^{-1}P(\omega)^*$$

if R=α and Q=1.

In some embodiments, the form of the learning algorithm is:

$$u_{k+1}(t) = u_k(t) + \rho(\omega)P^+(\omega)e_k(t)$$

Here, the concepts of the pseudo-inverse and the iteration-gain function are combined. As mentioned before, if $P^+(\omega)$ is exactly the inverse of the true system, then convergence is achieved in one iteration. However, if $P^+(\omega)$ is not exactly the inverse (modeling error), the controller can become unstable.

Some embodiments take into account modeling errors as follows. If $P_0(\omega)$ is the true system and $\hat{P}(\omega)$ is the estimated system, the modeling error is defined as:

$$\Delta_p(\omega) = \frac{P_0(\omega)}{\hat{P}(\omega)} = \frac{P_0(\omega)e^{j\theta_0(\omega)}}{\hat{P}(\omega)e^{j\hat{\theta}(\omega)}} = \Delta_a(\omega)e^{j\Delta_\theta(\omega)}$$

$\Delta_a(\omega)$ is then the magnitude modeling error, and $\Delta_\theta(\omega)$ is the phase modeling error. The iterations are guaranteed to converge if:
1. The magnitude of the phase variation is less than π/2: $|\Delta_\theta(\omega)| < \pi/2$, at frequency ω.
2. The iteration coefficient ρ(ω) is chosen as:

$$0 < \rho(\omega) < \frac{2\cos(\Delta_\theta(\omega))}{\Delta_a(\omega)}$$

Furthermore, in the presence of measurement noise, the iterations are still guaranteed to converge if ρ(ω) is low enough and the number of iterations large enough.

Figure 25:
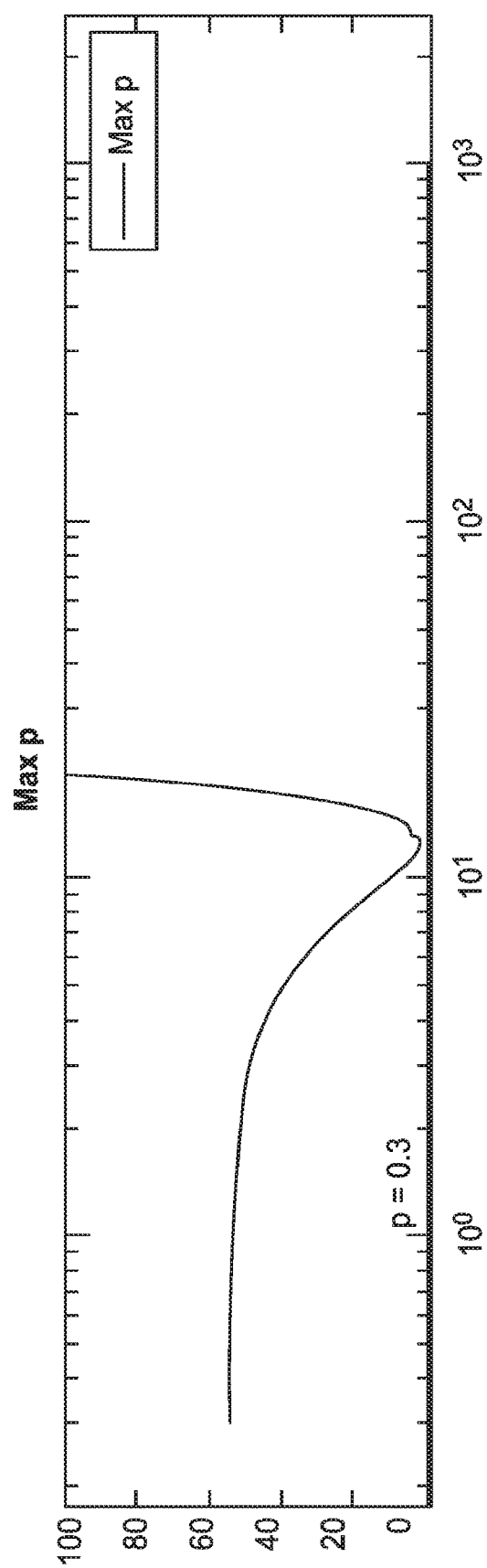
FIG. 25 illustrates an exemplary maximum allowable $\rho(\omega)$ in the iterative learning control, in accordance with embodiments.

FIG. 25 illustrates a plot of the maximum allowable ρ(ω), in accordance with embodiments. The embodiment of FIG. 25 is obtained when performing a simulation where the true and estimated model of a harmonic oscillator system has 10% natural frequency and damping factor error, based on the previous equation. The horizontal line is ρ(ω)=0.3. As such, ρ(ω) can be used to ensure convergence in the presence of modeling error. The values of ρ(ω) can be chosen to trade off between robustness and aggressive convergence rates. ρ(ω) can also be a function of frequency to tailor the convergence rates at different ω.

In some embodiments, ILC implementations are optimized when measurement of the achieved trajectory is accurate. The fiber tip deflection may not be directly observed, but it can be isolated from the system model. Since it can be assumed that the subsystem corresponding to the first vibration mode is time-varying, using a regular observer for the fiber tip state is not feasible in some embodiments. One approach is to perform a complementary observation of the fiber tip: since it is assumed that the other portions of the model (electrical circuit) are time-invariant, the other states can be predicted from the input-output data and their contributions subtracted from the f signal. The remaining "complement" can give a reading of the fiber deflection.

Self-calibrating Scanning Fiber System

As previously described, the adaptive techniques or adaptive feedforward techniques provided herein can be used to provide automatic self-calibration of optical fiber scanners. For example, the self-sensing circuitry disclosed herein can be used in combination with piezoelectric actuators to detect changes in various scanner parameters and modify the driving inputs used to drive the scanning of the optical fiber, based on the updated parameters. Such self-sensing circuitry can be designed to measure the optical fiber displacement (e.g., via piezoelectric self-sensing signals) when the fiber is being driven by the piezoelectric actuator, when the fiber is not being driven (e.g., during settling), or suitable combinations thereof.

Figure 13A:
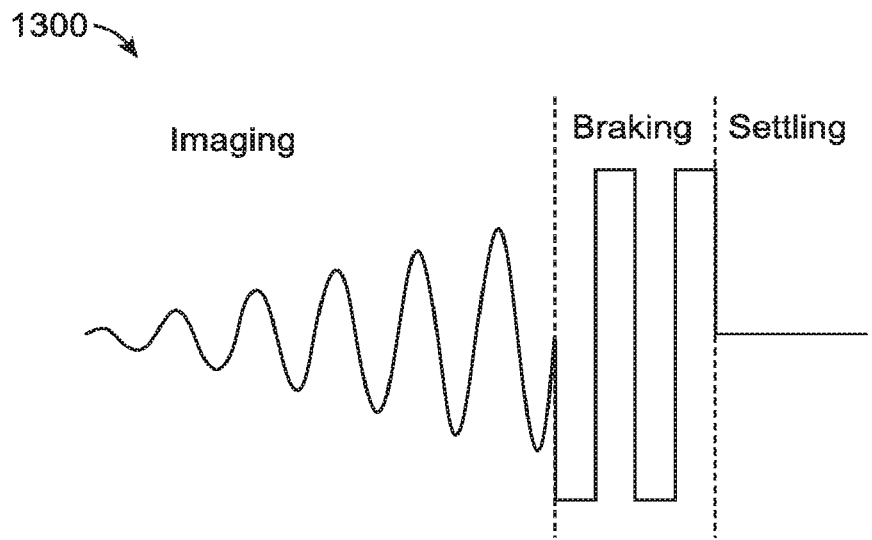
FIG. 13A illustrates a piezoelectric drive signal for driving a scanning optical fiber, in accordance with embodiments.
Figure 13B:
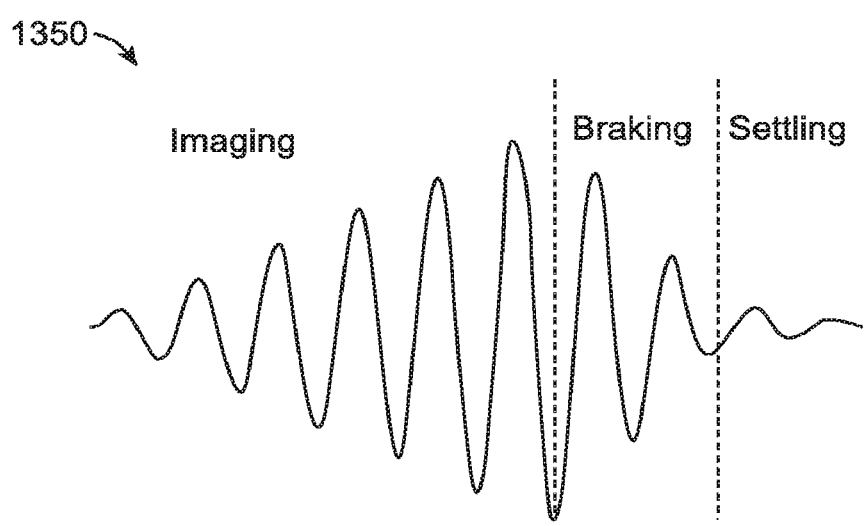
FIG. 13B illustrates an exemplary scanner response produced in a response to a driving signal, in accordance with embodiments.

FIG. 13A illustrates a piezoelectric drive signal 1300 for driving a scanning optical fiber, in accordance with embodiments. The piezoelectric drive signal 1300 can be applied to the optical fiber along each eigendirection. The piezoelectric drive signal 1300 can include an imaging phase, a braking phase, and a settling phase. The imaging phase can include a ramping sinusoidal signal that, when applied along both virtual axes, produces a spiral scan pattern, as described above. The braking signal can include large amplitude square waves applied to the optical fiber to rapidly bring it to rest. The settling phase can involve allowing residual vibrations of the fiber to decay without the application of any driving signal. Following the settling phase, the sequence can be repeated to capture a new image frame. Collectively, the three phases—imaging, braking, and settling—can be referred to as a "scanning profile." FIG. 13B illustrates an exemplary scanner response 1350 produced in response to a driving signal, in accordance with embodiments. For instance, the scanner response 1350 may be produced in response to the driving signal 1300. The scanner response 1350 includes imaging, braking, and settling phases corresponding to the imaging, braking, and settling phases of the drive signal 1300.

For example, during the imaging phase, a ramping sine and a ramping cosine can be applied to each eigendirection:

$$\begin{bmatrix} F_1(t) \\ F_2(t) \end{bmatrix} = \begin{bmatrix} A_1 t\sin(\omega t) \\ A_2 t\cos(\omega t) \end{bmatrix} \quad \text{(Eq. 13)}$$

where $A_1$ and $A_2$ are the excitation amplitudes and the excitation frequency ω is selected to be:

$$\omega = \frac{\omega_{r,1} + \omega_{r,2}}{2} \quad \text{(Eq. 14)}$$

with $\omega_r$ being the resonant frequency of the 1$^{st}$ vibration mode given by:

$$\omega_r = \omega_0\sqrt{1 - 2\zeta^2} \quad \text{(Eq. 15)}$$

ω can be selected such that it is closest to the 1$^{st}$ mode resonant peaks along both eigendirections in order to generate large scanner deflection and hence a high field of view (FOV). In some embodiments, for optimal operation of the imaging phase, the frequencies $\omega_{r,1}$ and $\omega_{r,2}$ (subscripts 1 and 2 refer to the first and second eigendirections, respectively) can be determined so that an increased (e.g., maximum) FOV is achieved.

During the braking phase, large amplitude square waves (braking drive) can be applied to each eigendirection to rapidly collapse the scan. The braking drive can be at the $1^{st}$ damped natural frequency:

$$\omega_d = \omega_0 \sqrt{1-\zeta^2} \quad \text{(Eq. 16)}$$

The phase can lag the scanner displacement by precisely $$\phi_{Brake,Rel} = \frac{-\pi}{2} \text{rad.}$$

For instance, at a reference time t=0, $x(0)=x_{max}>0$ and $\dot{x}(t)=0$. Applying a braking drive with phase lag $$\frac{\pi}{2} \text{rad,}$$

the following relationship can be obtained:

$$\ddot{x} + 2\zeta\omega_0\dot{x} + \omega_0^2 x = \quad \text{(Eq. 18)}$$

$$\frac{F_{Brake}(t)}{m} = \begin{cases} \frac{A_{Brake}}{\omega_0^2}, & t = \left[(n-1)T, \frac{nT}{2}\right], \ n = 1, 2, 3 \ldots \\ \frac{-A_{Brake}}{\omega_0^2}, & t = \left[\frac{nT}{2}, nT\right], \ n = 1, 2, 3 \ldots \end{cases}$$

where $T = \frac{2\pi}{\omega_d}$.

Solving the Initial Value Problem gives:

$$x\left(\frac{nT}{2}\right) = -\left(e^{\frac{-\pi\zeta}{\sqrt{1-\zeta^2}}}\right)x\left(\frac{(n-1)T}{2}\right) + \left(1 + e^{\frac{-\pi\zeta}{\sqrt{1-\zeta^2}}}\right)A_{Brake}, \quad \text{(Eq. 18)}$$

$$n = 1, 2, 3, \ldots$$

$$\dot{x}\left(\frac{nT}{2}\right) = 0, n = 1, 2, 3 \ldots \quad \text{(Eq. 19)}$$

If $$A_{Brake} = \frac{\left(e^{\frac{-\pi\zeta}{\sqrt{1-\zeta^2}}}\right)x(0)}{1 + e^{\frac{-\pi\zeta}{\sqrt{1-\zeta^2}}}}, \text{ then } x\left(\frac{T}{2}\right) = 0 \text{ and } \dot{x}\left(\frac{T}{2}\right) = 0,$$

such that the scanner can be brought to rest in $$\frac{T}{2}.$$

This may involve me application of a very large voltage. Instead, if:

$$A_{Brake} \leq \frac{\left(e^{\frac{-\pi\zeta}{\sqrt{1-\zeta^2}}}\right)x\left(\frac{(n-1)T}{2}\right)}{1 + e^{\frac{-\pi\zeta}{\sqrt{1-\zeta^2}}}}, n = 1, 2, 3 \ldots \quad \text{(Eq. 20)}$$

then:

$$\left|x\left(\frac{nT}{2}\right)\right| \leq \left|x\left(\frac{(n-1)T}{2}\right)\right|, n = 1, 2, 3 \ldots \quad \text{(Eq. 21)}$$

That is, the amplitude of vibration decreases (more rapidly with larger $A_{Brake}$) until Eq. 20 does not hold. At that point, braking can be turned off or the amplitude may start to increase.

Braking can be applied at $$\phi_{Brake,Rel} = \frac{-\pi}{2} \text{rad}$$

or Eq. 17 may not hold. If the braking phase is incorrect $$\left(e.g., \phi_{Brake,Rel} = \frac{-3\pi}{2}\right), \text{ then}$$

$$\left|x\left(\frac{nT}{2}\right)\right| = \left|\left(e^{\frac{-\pi\zeta}{\sqrt{1-\zeta^2}}}\right)x\left(\frac{(n-1)T}{2}\right) + \left(1 + e^{\frac{-\pi\zeta}{\sqrt{1-\zeta^2}}}\right)A_{Brake}\right|,$$

$$n = 1, 2, 3 \ldots$$

that is, the braking drive can actually increase the amplitude of motion. Note that $$\phi_{Brake,Rel} = \frac{-\pi}{2}$$

is relative to the scanner displacement along an eigendirection. The scanner response can have an absolute phase $\phi_{Motion}$, which may depend on the excitation and mechanical properties of the scanner. Thus, the absolute braking phase is $\phi_{Brake} = \phi_{Brake,Rel} + \phi_{Motion}$, which may vary between eigendirections and from system to system.

The settling phase may be appropriate because the scanner may not be fully at rest upon completion of the braking phase. When braking is turned off after Eq. 20 no longer holds, the inequality in Eq. 21 does not guarantee that $x(t)=0$, though $|x(t)|$ may be small. Also, unmodeled dynamics, such as higher vibration modes, can be excited and may be allowed to decay. The more precisely braking is applied, the shorter the settling phase, can be, leading to increased video frame rate for the optical fiber scanner.

FIGS. 14A and 14B illustrate extended mode shapes 1400, 1450, respectively, for displacement of an optical fiber and piezoelectric actuator, in accordance with embodiments. The first extended mode shape 1400 may be the operating mode of the scanning optical fiber system. The strain (or displacement) of the piezoelectric tube may be directly proportional to the deflection of the optical fiber. Accordingly, the position of the optical fiber can be measured by sensing the strain of the piezoelectric tube. The approaches described herein may consider the deformation of the composite piezoelectric tube-and-optical fiber cantilever structure, using the attaching collar as a rigid reference. This strategy may provide a more complete analysis of system behavior compared to alternative approaches which focus on the optical fiber without considering the dynamics of the piezoelectric tube.

Figure 15A:
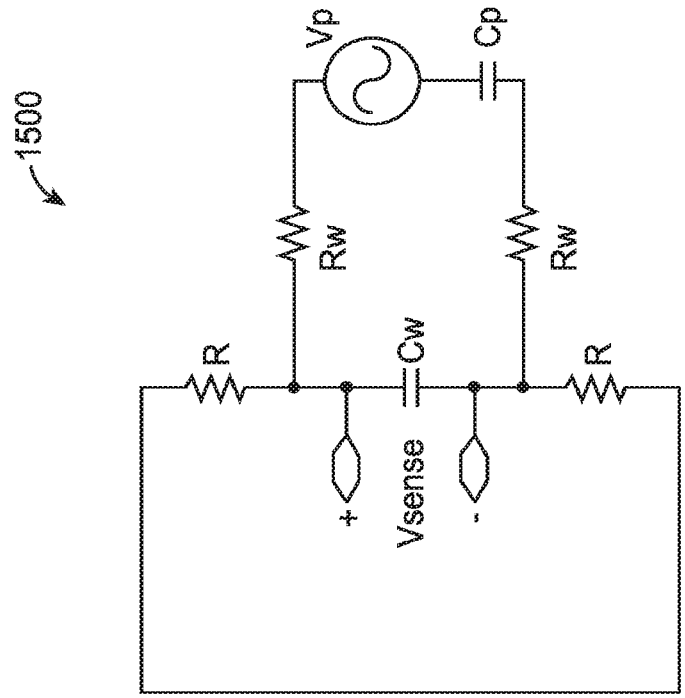
FIGS. 15A and 15B illustrate a lumped-element model of a piezoelectric self-sensing circuit, in accordance with embodiments.
Figure 15B:
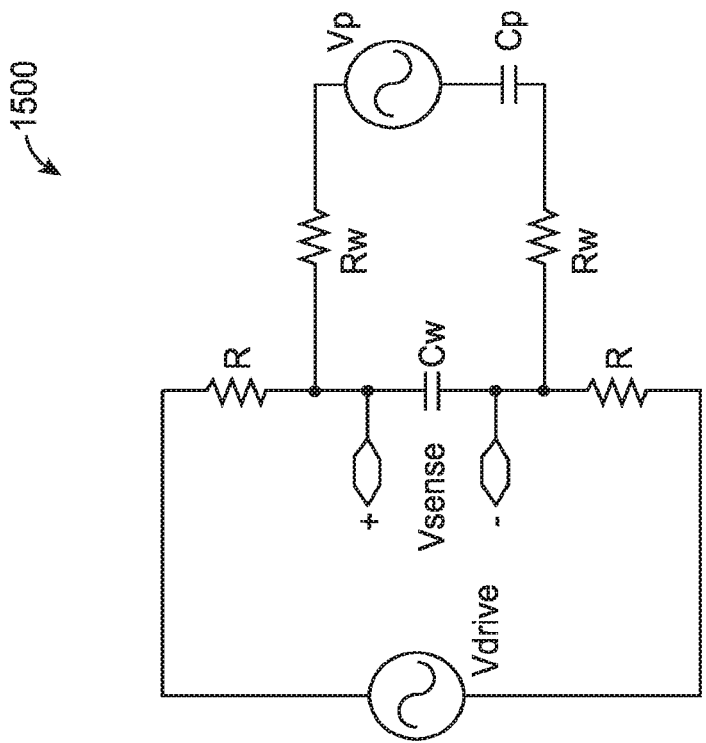

FIGS. 15A and 15B illustrate a lumped-element model of a piezoelectric self-sensing circuit 1500, in accordance with embodiments. The circuit 1500 can be used to measure piezoelectric displacement signals in embodiments where the actuation and sensing of the piezoelectric actuator occur at different times. The circuit 1500 can include a drive voltage source ($V_{drive}$). The piezoelectric tube can be modeled as a voltage source $V_P(t)$ in series with a capacitor $C_P$. The voltage $V_P(t)$ is the piezoelectrically-generated voltage that is proportional to the strain of the piezoelectric element.

When $V_{Drive}(t)$ is active as shown in FIG. 15A, (e.g., when the scanner is being actuated), the sensed voltage $V_{Sense}(t)$ can be given in the Laplace domain as:

$$V_{Sense}(s) = \frac{2R_W C_P s + 1}{4RR_W C_W C_P s^2 + 2[R_W C_P + R(C_W + C_P)]s + 1} V_{Drive}(s) + \frac{2RC_P s}{4RR_W C_W C_P s^2 + 2[R_W C_P + R(C_W + C_P)]s + 1} V_P(s) \quad \text{(Eq. 22)}$$

where $R_W$ is the wire resistance, $C_W$ the wire capacitance, R the resistors illustrated in FIGS. 15A and 15B, and s the Laplace variable. Since typically $|V_{Drive}| \gg |V_P|$, in Eq. 22, $V_{Sense} \cong V_{Drive}$, such that it may not be possible to directly measure $V_P$ when actuating.

However, when the drive is not active, as shown in FIG. 15B, $$V_{Sense}(s) = \frac{2RC_P s}{4RR_W C_W C_P s^2 + 2[R_W C_P + R(C_W + C_P)]s + 1} V_P(s), \quad \text{(Eq. 23)}$$

$$V_{Drive}(s) = 0$$

the piezoelectric-tube strain can be directly measured when not actuating. Note that in Eq. 23, the piezoelectric signal is band-passed through a filter with poles given by $4RR_W C_W C_P s^2 + 2[R_W C_P R(C_W + C_P)]s + 1 = 0$ and design variable R.

In embodiments where the optical fiber scanner is an underdamped resonant system, it may continue to oscillate even after forcing is removed. Hence, Eq. 23 means that a drive signal can be applied to the piezoelectric tube, and the residual oscillations then measured via piezoelectric sensing. This approach can be used to identify the relevant parameters for precision scanning optical fiber imaging, such as the eigendirections, the resonant and damped natural frequencies, and the braking phases.

The stress (which produces a torque) on a piezoelectric tube may be proportional to the incident electric field. By applying electrical drive signals to the piezoelectric tube, the force acting on the cantilevered fiber scanner can be controlled. To identify the eigendirections, the following diagnostic signal can be applied:

$$\begin{bmatrix} F_{1,Piezoelectric\text{-}tube}(t) \\ F_{2,Piezoelectric\text{-}tube}(t) \end{bmatrix} = \begin{bmatrix} \cos\alpha \sin(\omega_{nom} t) \\ -\sin\alpha \sin(\omega_{nom} t) \end{bmatrix} \quad \text{(Eq. 24)}$$

where $\omega_{norm}$ is a nominal guess of the resonant frequency and $\alpha$ a "test angle" that can be swept from 0 to $\pi$ rad. When $\alpha = f$ (the eigendirection angle), a line-response can be obtained. When forcing is turned off, at $t = T_{final}$, the initial conditions for the free decay can be determined in a manner known to one of skill in the art. The free oscillations can calculate to $$\begin{bmatrix} x_{1,decay}(t) \\ x_{2,decay}(t) \end{bmatrix} = \begin{bmatrix} A_1 e^{-\zeta_1 \omega_{0,1} t} \sin(\omega_{d,1} t + \varphi_1) \\ 0 \end{bmatrix} \quad \text{(Eq. 25)}$$

where the amplitude $A_1$ and phase $\varphi_1$ depend on the initial conditions. Eq. 25 describes a one-dimensional signal. For line geometry, the flattening criterion $$f = \frac{a - b}{a} \quad \text{(Eq. 26)}$$

where a is the semi-major axis length and b is the semi-minor axis length can be maximum-valued or approximately maximum-valued at 1, in some embodiments. By sweeping $\alpha$ from 0 to $\pi$ rad, maximum or approximately maximum flatness can be achieved when $\alpha \cong \theta$, in some embodiments. Accordingly, the eigendirection parameter $\theta$ can be identified.

Figure 16A:
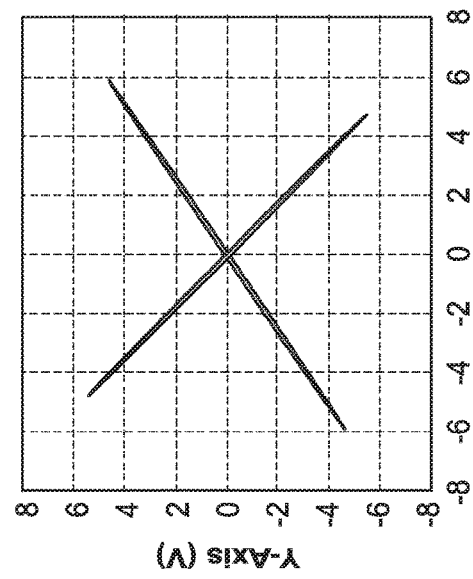
FIGS. 16A through 16C illustrate exemplary optical fiber responses, in accordance with embodiments.
Figure 16B:
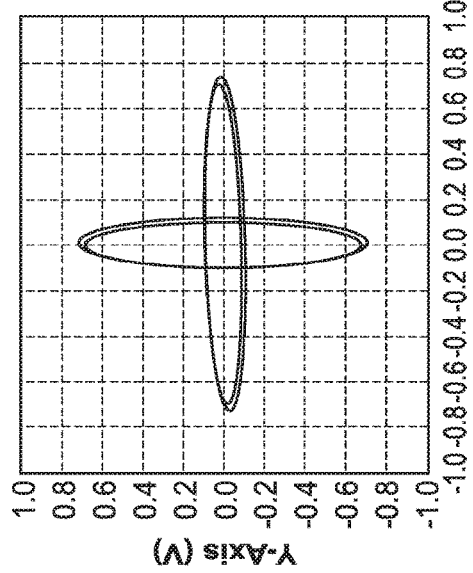
Figure 16C:
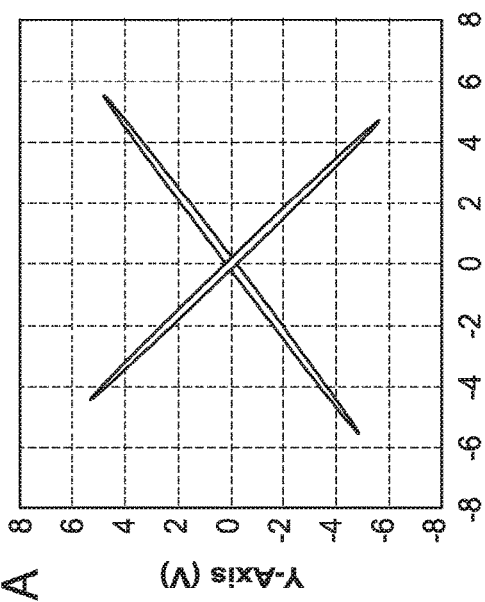

FIGS. 16A-16C illustrate exemplary optical fiber responses that can be obtained using the methods described herein, in accordance with embodiments. FIG. 16A shows whirling motion (low flatness) that may be observed when $\alpha \neq \theta$. FIG. 16B shows a result of the identification procedure described herein. When $\alpha \cong \theta$, maximal flatness may be achieved. FIG. 16C illustrates optical position sensor data verifying that whirling was eliminated when driving along the identified eigendirections.

Comparing Eq. 15 and Eq. 16, when effective damping $\zeta$ is small, $\omega_r \cong \omega_d$. For the scanning optical fiber system, measure $\omega_d$ can be accurately measured and the preceding assumption can be used for $\omega_r$. $\omega_d$ may be used for precise braking and distortionless images. If $\omega_r$ is inaccurate, a slightly smaller FOV may result, which may not be as detrimental to image quality.

Once the eigendirections are identified, the diagnostic signal $$\begin{bmatrix} F_{1,Piezoelectric\text{-}tube}(t) \\ F_{2,Piezoelectric\text{-}tube}(t) \end{bmatrix} = \begin{bmatrix} \cos\theta \sin(\omega_{nom} t) \\ -\sin\theta \sin(\omega_{nom} t) \end{bmatrix}$$

can be applied, and then the forcing turned off. This can produce free oscillations along the first eigendirection (Eigendirection 1) as described in Eq. 25. The Fourier transform of $x_{1,decay}(t)$ is:

$$X_{1,decay}(\omega) = \frac{B_1 \omega_{d,1} + C_1(\zeta_1 \omega_{0,1} + j\omega)}{\omega_{d,1}^2 + (\zeta_1 \omega_{0,1} + j\omega)^2} \quad \text{(Eq. 27)}$$

where j is the imaginary unit, $\omega$ the frequency variable of the Fourier transform and $B_1$ and $C_1$ are coefficients that depend on the initial conditions before free decay. The magnitude plot of Eq. 27 may have a peak at $\omega = \omega_{d,1}$. From the measured samples of $x_{1,decay}(t)$, the discrete Fast Fourier Transform (FFT) can be taken and $\omega_{d,1}$ can be identified from the peak in the FFT magnitude plot. This process can be repeated for the second eigendirection (Eigendirection 2).

Figure 17:
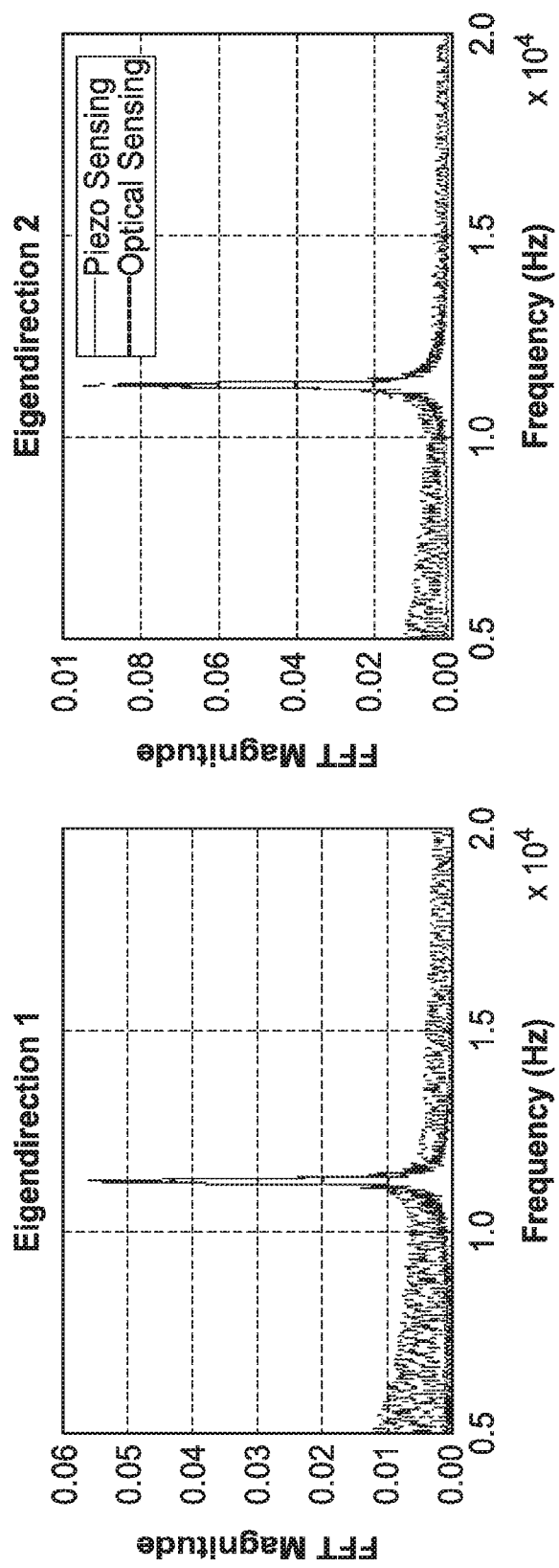
FIG. 17 illustrates Fast Fourier Transform (FFT) magnitude plots of exemplary data obtained with piezoelectric sensing, in accordance with embodiments.

FIG. 17 illustrates FFT magnitude plots of exemplary data obtained with piezoelectric sensing, in accordance with embodiments. The very prominent peaks in the FFT plots can allow for accurate identification of $\omega_d$. Additionally, data from an optical position sensor can be used to verify the identified frequencies.

As previously described herein, braking can be applied at a precise phase $\emptyset_{Brake}$ to bring the scanner as close to rest as possible. The exact value of $\emptyset_{Brake}$ can be determined empirically by sweeping a "test" phase $\beta$ between $$\frac{-\pi}{4} \text{ and } \frac{-3\pi}{4} \text{ rad.}$$

The displacement and velocity of the scanner may be reduced (e.g., minimized) when $\beta \cong \emptyset_{Brake}$.

When operating at the $1^{st}$ extended mode, due to discontinuous forcing, the $2^{nd}$ and higher extended modes may be slightly excited. Referring to FIG. 14B, the $2^{nd}$ extended mode may incorporate large relative deformations of the piezoelectric-tube compared to the $1^{st}$ extended mode (depicted in FIG. 14A). As such, it can be difficult to separate the amplitudes of the $1^{st}$ and $2^{nd}$ extended modes just by observing the piezoelectric tube displacement (using piezoelectric sensing), when the amplitude of the $1^{st}$ mode is small. To precisely identify $\emptyset_{Brake}$, it may be helpful to quantify small residual vibrations of the $1^{st}$ extended mode.

To separate the amplitudes of the $1^{st}$ and $2^{nd}$ extended modes, frequency analysis can be used. The damped natural frequency of the $2^{nd}$ extended mode may be much higher than that of the $1^{st}$ extended mode, thus they may have distinct peaks in the frequency spectrum. From Eq. 27, for free decay on Eigendirection 1, the height of the FFT magnitude peak at $\omega=\omega_{d,1}$, $|X_{1,decay}(\omega_{d,1})|$ can be proportional to $\sqrt{(B_1\omega_{d,1}+C_1\zeta_1\omega_{0,1})^2+(C_1\omega_{d,1})^2}$, where $B_1$ and $C_1$ are directly proportional to the initial displacement, $x_i$ and the initial velocity, $v_i$ at the onset of free decay:

$$B_1 = \frac{v_i + \zeta_1 \omega_{0,1} x_i}{\omega_{d,1}} \quad \text{(Eq. 28)}$$

$$C_1 = x_i \quad \text{(Eq. 29)}$$

This shows that $|X_{1,decay}(\omega_{d,1})|$ can be proportional to the initial displacement and velocity of the $1^{st}$ extended mode on Eigendirection 1, thus providing a method of measuring how much "at rest" the $1^{st}$ extended mode is.

The following procedure can be used to identify the braking phases. On Eigendirection 1, the scanning optical fiber system can be scanned with the nominal ramping sinusoid, then braking can be applied. During braking, a "test" phase $\beta$ can be swept between $$\frac{-\pi}{4} \text{ and } \frac{-3\pi}{4} \text{ rad}$$

for different trials. This can constitute the diagnostic signal. After braking in each trial, $|X_{1,decay}(\omega_{d,1})|$ can be measured. In some embodiments, the minimum or approximately minimum $|X_{1,decay}(\omega_{d,1})|$ can be used to indicate $\beta \cong \emptyset_{Brake,1}$. This can be repeated on Eigendirection 2 to identify $\emptyset_{Brake,2}$.

Figure 18A:
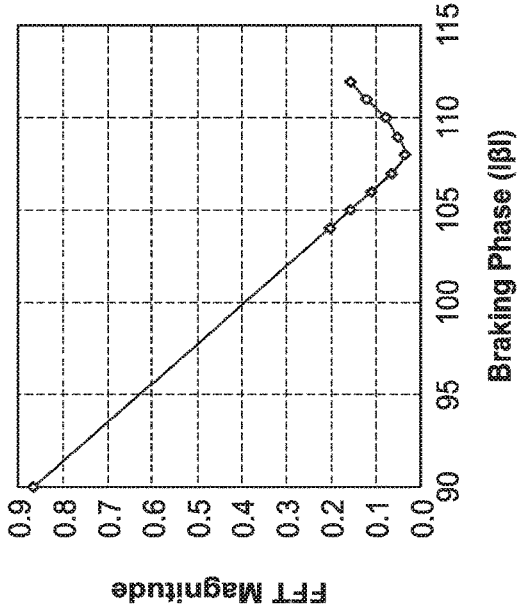
FIG. 18A illustrates an exemplary FFT magnitude plot for different identification trials, in accordance with embodiments.
Figure 18B:
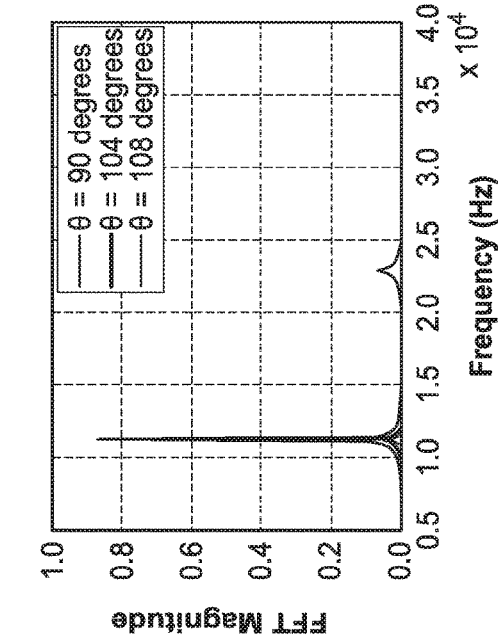
FIG. 18B illustrates exemplary identification of the optimal braking phase, in accordance with embodiments.
Figure 18C:
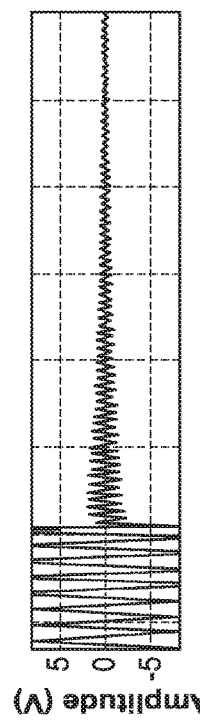
FIG. 18C illustrates an exemplary piezoelectric sensing signal after optimal braking, in accordance with embodiments.
Figure 18D:
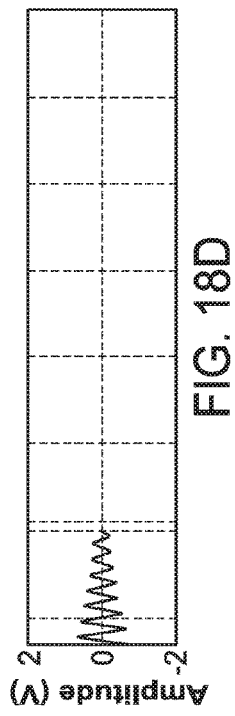
FIG. 18D illustrates exemplary optical position sensor data tracking the position of an optical fiber tip, in accordance with embodiments.

FIG. 18A shows an exemplary FFT magnitude plot for different identification trials, in accordance with embodiments. The height of the first peak changes for different braking phases, as predicted by Eq. 27-29. FIG. 18B illustrates exemplary identification of the optimal braking phase by tracking the height of the peak for different $\beta$ and finding the minimum or approximately minimum point, in accordance with embodiments. FIG. 18C illustrates an exemplary piezoelectric sensing signal after optimal braking, in accordance with embodiments. Piezoelectric sensing can be used to track the position of the piezoelectric tube. When braking is effective, lower frequency oscillations of the $1^{st}$ extended mode are absent, but higher frequency residual vibration of the $2^{nd}$ extended mode is detected. FIG. 18D illustrates exemplary optical position sensor data tracking the position of the optical fiber tip, in accordance with embodiments. Since the $1^{st}$ extended mode is practically at rest, the deflections of the fiber tip are negligible.

Since pertinent parameters of the scanning optical fiber system can be identified via piezoelectric sensing, as described herein, these parameters can therefore be tracked over changing operating conditions. The eigendirections and $1^{st}$ extended mode damped natural frequencies of an optical fiber scanner may drift very little over time. To identify new values for these parameters, the system can periodically repeat the procedures described above. In addition, estimates of the new parameter values can be used as a starting point, since parameter drifts tend to be continuous, thus reducing the number of identification iterations. Each identification iteration can take less than 50 milliseconds (e.g., at most 25 k data samples obtained at 500 k samples/s) and thus may not be noticeable or disruptive to the scanner operator (e.g., for endoscope applications).

The optical fiber scanner may be more sensitive to braking phase inaccuracies. To identify new braking phase, the procedures described above may be repeated, or, alternatively, the amount of change in the time-signal phase $\emptyset_{Motion}$ can be determined. Since $$\emptyset_{Brake} = \frac{-\pi}{2} + \emptyset_{Motion},$$

the change in $\emptyset_{Motion}$ is equal to the change in $\emptyset_{Brake}$. This approach may enable the braking phase to be updated more quickly.

Figure 19C:
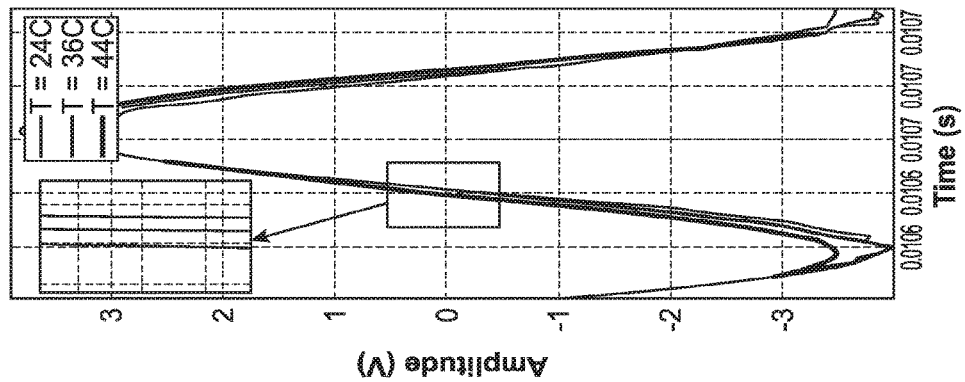
FIG. 19C illustrates an exemplary time signal, in accordance with embodiments.
Figure 19B:
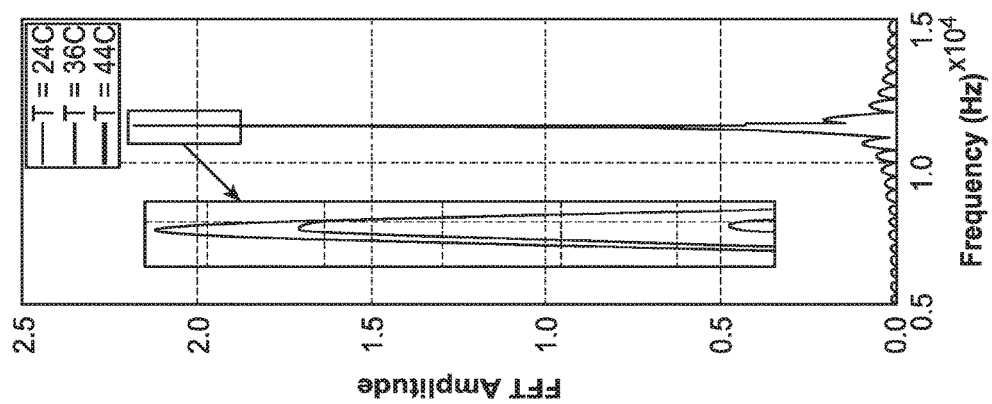
FIG. 19B illustrates exemplary tracked damped natural frequency peaks at different temperature, in accordance with embodiments.
Figure 19A:
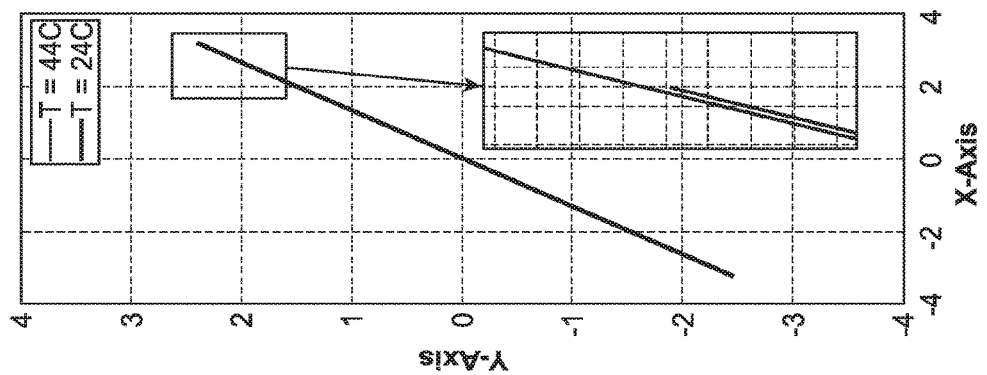
FIG. 19A illustrates exemplary identification of eigendirections at two different temperatures, in accordance with embodiments.

FIG. 19A shows exemplary identification of eigendirections at two different temperatures, revealing a 1.1° clockwise rotation at 44° C. relative to 24° C. FIG. 19B shows exemplary tracked damped natural frequency peaks at different temperatures, indicating a slight decreasing trend. FIG. 19C shows an exemplary time signal, with observed phase drift as temperature increases. FIG. 19D shows an exemplary scanner displacement profile at 44° C. before and after recalibration with the piezoelectric sensing approach provided herein. Before recalibration, the scanner may still be vigorously vibrating when the next image cycle begins, leading to distorted images. After recalibration, scan control and braking may be much more effective and the scanner may be brought to rest before the next image cycle, thus producing clear images with minimal or no distortions.

The designed identification procedures provided herein can have quantifiable measures to optimize the following:

increase (e.g., maximize) flatness to find the eigendirections, locate spectrum peaks (e.g., maximum or approximately maximum value) to identify damped natural frequencies, and decrease (e.g., minimize) spectrum height to find braking phases. Thus, the system can be computer-automated to repeat these identification steps periodically to recalibrate itself without human assistance and without an extrinsic calibration setup (e.g., a calibration chamber). For example, for endoscopes utilizing the scanning optical fiber systems described herein, since the piezoelectric sensor is inside the endoscope probe, the automated calibration can be a fully self-contained process that maintains high image quality, thus enhancing the convenience, flexibility, and applicability of the endoscope for lengthy medical procedures.

Example: Spiral-out and Spiral-in Imaging

This example describes an imaging procedure performed using a scanning optical fiber system. A scanning optical fiber was driven in an alternating outward and inward spiral scan pattern ("spiral-out" and "spiral-in"). The drive signals for controlling the trajectory of the optical fiber were generated based on a dynamic model in accordance with the embodiments provided herein. The model was identified automatically, with manual adjustments to the natural frequency and damping factor parameters. Rapid re-calculation and adjustment of the dynamic model performed manually using LABVIEW software during imaging allowed the spiral-out and spiral-in trajectories to track well enough such that data from both portions of the scan could be interleaved and used for imaging without image doubling.

Figure 26:
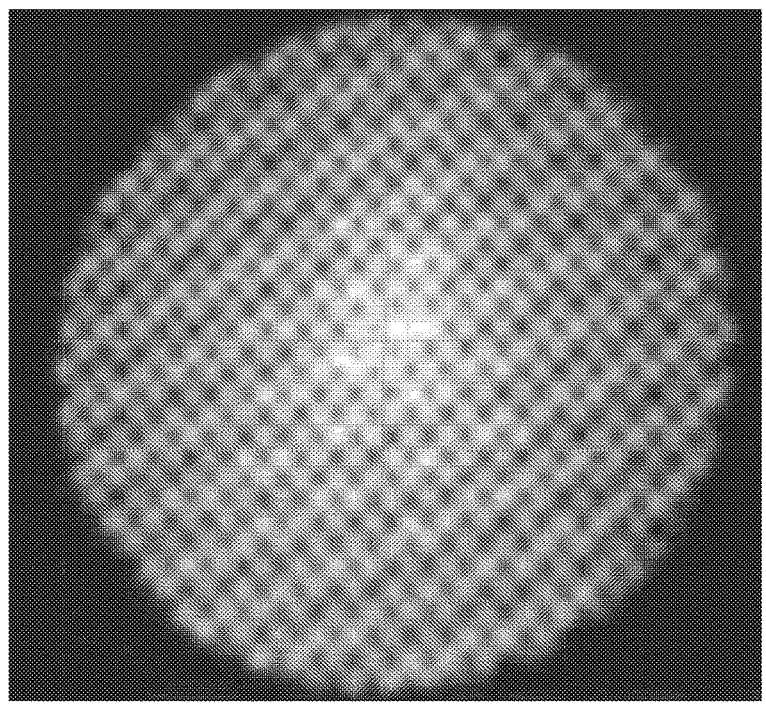
FIG. 26 illustrates exemplary image data obtained using spiral-out and spiral-in imaging, in accordance with embodiments.
Figures 27A, 27B:
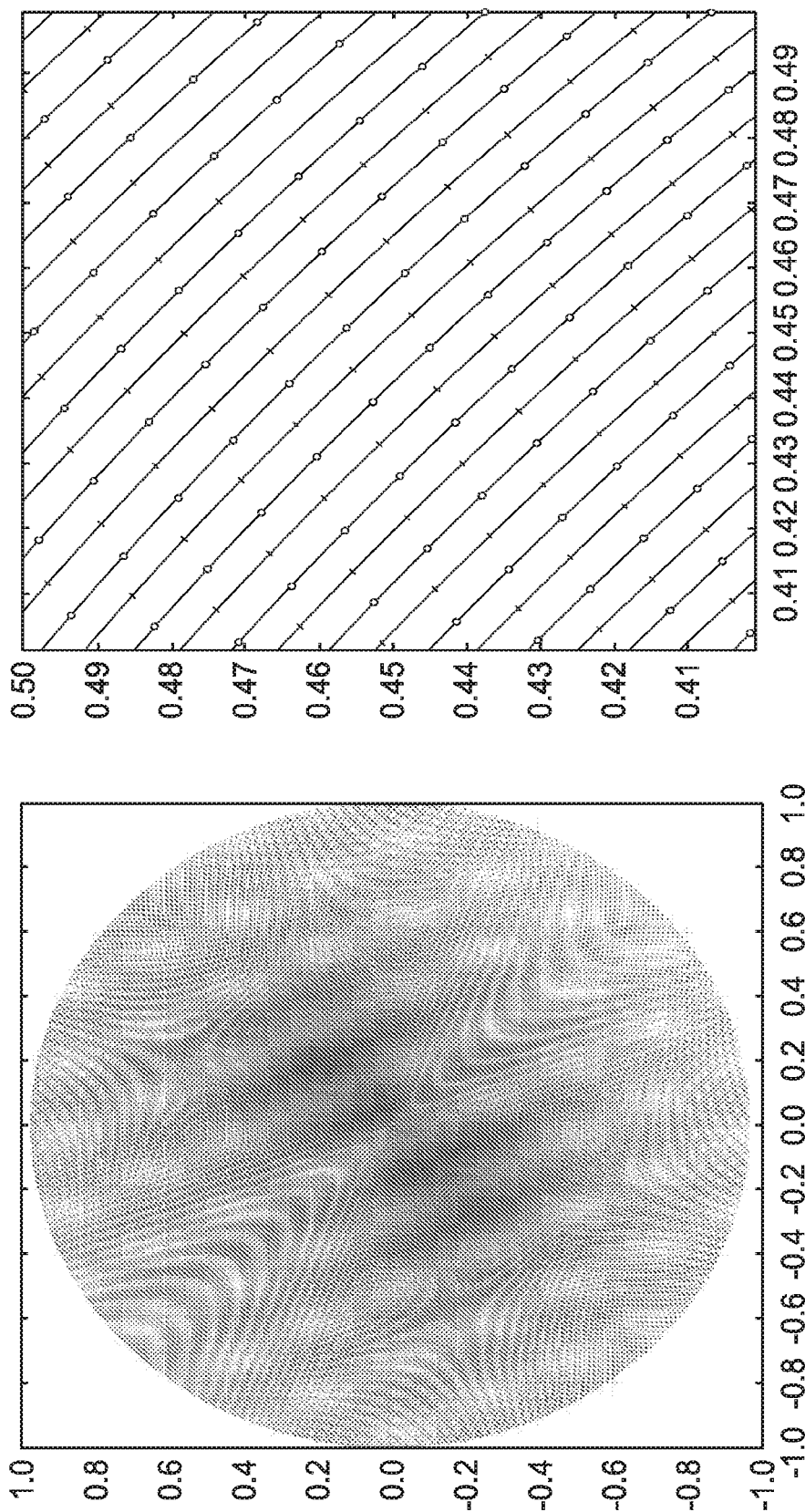
FIGS. 27A through 27C illustrates an exemplary pixel sampling distribution used for the spiral-out and spiral-in imaging, in accordance with embodiments.
Figure 27C:
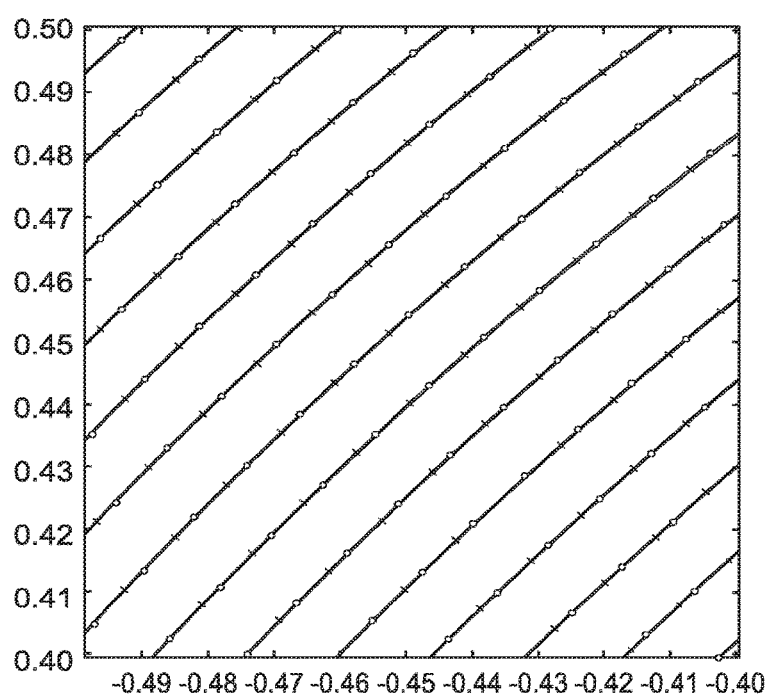

FIG. 26 illustrates exemplary image data of a fine-square checkerboard pattern obtained using spiral-out and spiral-in imaging. Horizontal and vertical lines are overlaid onto the image to demonstrate that the straight edges of the checkerboard were preserved. FIG. 27A through 27C illustrate an exemplary pixel sampling distribution used for spiral-out and spiral-in imaging (circles correspond to spiral-out, ticks corresponding to spiral-in). The density and area of the inward and outward scans were the same, although the arrangement was different.

These results demonstrate that modeling approaches can be used to control the fiber trajectory with sufficient accuracy to allow for interleaving of spiral-out and spiral-in image data, thereby avoiding the use of braking and settling phases during which scanning is not performed. Advantageously, in contrast to approaches that only utilize the spiral-out scan for imaging, the use of spiral-out and spiral-in imaging can increase scanning efficiency, frame rate, and image resolution, as well as achieve near 100% duty cycle operation of the scanning optical fiber system.

The various techniques described herein may be partially or fully implemented using code that is storable upon storage media and computer readable media, and executable by one or more processors of a computer system. The processor can comprise array logic such as programmable array logic (hereinafter PAL), configured to perform the techniques described herein. Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices, or any other medium which can be used to store the desired information and which can be accessed by the a system device. Based on the disclosure and teachings provided herein, a person of ordinary skill in the art will appreciate other ways and/or methods to implement the various embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A scanning apparatus, comprising:
   an optical fiber;
   a piezoelectric actuator coupled to the optical fiber to deflect a distal end of the optical fiber in a scanning pattern;
   sensing circuitry coupled to the piezoelectric actuator to measure a displacement of the piezoelectric actuator and output a displacement signal;
   drive circuitry coupled to the piezoelectric actuator to drive the piezoelectric actuator in response to a drive signal; and
   a processor coupled to the drive circuitry and the sensing circuitry, wherein the processor includes logic that when executed by the processor causes the scanning apparatus to perform operations including:
   obtaining the displacement signal with the processor;
   selecting a vibrational mode from a plurality of vibrational modes based on the displacement signal; and
   controlling, with the drive signal, a trajectory of the optical fiber based on the vibrational mode.

2. The scanning apparatus of claim 1, wherein the processor further includes logic that when executed by the processor causes the scanning apparatus to perform operations including:
   decomposing the displacement signal into the plurality of vibrational modes before selecting the vibrational mode.

3. The scanning apparatus of claim 2, wherein decomposing the displacement signal includes:
   applying a least squares fit to an autoregressive-moving-average (ARMA) model of the displacement signal; and
   obtaining a modal matrix from the ARMA model containing the plurality of vibrational modes.

4. The scanning apparatus of claim 1, wherein the vibrational mode is selected based on at least one of a shape of the vibrational mode, or a magnitude of deflection of the optical fiber.

5. A method of operating a scanning fiber device, comprising:
   obtaining a displacement signal from sensing circuitry with a processor coupled to the sensing circuitry, wherein the sensing circuitry is coupled to a piezoelectric actuator to measure a displacement of the piezoelectric actuator;
   decomposing the displacement signal into a plurality of vibrational modes with the processor;

selecting a vibrational mode from the plurality of vibrational modes; and controlling a trajectory of an optical fiber with drive circuitry coupled to the piezoelectric actuator, wherein the controlling is based on the vibrational mode, and wherein and the drive circuitry is coupled to the processor, and the piezoelectric actuator is coupled to the optical fiber.

6. The method of claim 5, wherein controlling the trajectory includes outputting a drive signal from drive circuitry to the piezoelectric actuator to vibrate the piezoelectric actuator.

7. The method of claim 5, wherein decomposing the displacement signal includes:

applying a least squares fit to an autoregressive-moving-average (ARMA) model of the displacement signal; and obtaining a modal matrix from the ARMA model containing the plurality of vibrational modes.

8. The method of claim 5, wherein the vibrational mode is selected based on at least one of a shape of the vibrational mode, or a magnitude of deflection of the optical fiber.

9. The method of claim 5, wherein the vibrational mode is adaptively selected during operation of the scanning fiber device.

10. The method of claim 9, wherein the vibrational mode is selected after a batch of data in the displacement signal is collected and stored in memory coupled to the processor.

* * * * *